(12) United States Patent
Morris et al.

(10) Patent No.: US 7,988,721 B2
(45) Date of Patent: Aug. 2, 2011

(54) AXIALLY-RADIALLY NESTED EXPANDABLE DEVICE

(75) Inventors: Andrew Morris, San Diego, CA (US); Eric Schmid, San Diego, CA (US); Jeffrey T. Sheriff, San Marcos, CA (US); Keith Esser, San Diego, CA (US)

(73) Assignee: Reva Medical, Inc., San Diego, CA (US)

( * ) Notice: Subject to any disclaimer, the term of this patent is extended or adjusted under 35 U.S.C. 154(b) by 206 days.

(21) Appl. No.: 11/950,351

(22) Filed: Dec. 4, 2007

(65) Prior Publication Data
US 2009/0143853 A1 Jun. 4, 2009

Related U.S. Application Data

(60) Provisional application No. 60/991,481, filed on Nov. 30, 2007.

(51) Int. Cl.
*A61F 2/06* (2006.01)
(52) U.S. Cl. .................................... 623/1.16
(58) Field of Classification Search .............. 623/1.1, 623/1.11, 1.15, 1.16, 1.17–1.34, 1.36, 1.37, 623/1.49
See application file for complete search history.

(56) References Cited

U.S. PATENT DOCUMENTS

| | | | |
|---|---|---|---|
| 2,361,506 A * | 10/1944 | Smith et al. .................. | 602/58 |
| 3,620,218 A | 11/1971 | Schmitt | |
| 4,261,390 A | 4/1981 | Belofsky | |
| 4,383,555 A | 5/1983 | Finley | |
| 4,553,545 A | 11/1985 | Maass et al. | |
| 4,576,532 A | 3/1986 | Hanson et al. | |
| 4,714,508 A | 12/1987 | Chivens et al. | |
| 4,733,665 A | 3/1988 | Palmaz | |
| 4,739,762 A | 4/1988 | Palmaz | |
| 4,740,207 A | 4/1988 | Kreamer | |
| 4,748,982 A | 6/1988 | Horzewski et al. | |
| 4,762,129 A | 8/1988 | Bonzel | |
| 4,776,337 A | 10/1988 | Palmaz | |
| 4,788,751 A * | 12/1988 | Shely et al. .................. | 24/16 PB |
| 4,817,600 A | 4/1989 | Herms et al. | |

(Continued)

FOREIGN PATENT DOCUMENTS

EP 0756853 2/1997

(Continued)

OTHER PUBLICATIONS

Asahara, T. "Local delivery of vascular endothelial growth factor accelerates reendothelialization and attenuates intimal hyperplasia in balloon-insured rate carotid artery," *Circulation* 91: 2793-2801, 1995.

(Continued)

*Primary Examiner* — Anhtuan T Nguyen
*Assistant Examiner* — David Eastwood
(74) *Attorney, Agent, or Firm* — Knobbe, Martens, Olson & Bear, LLP

(57) ABSTRACT

Expandable medical implants for maintaining support of a body lumen are disclosed. These implants comprise an axially-radially nested, diametrically expandable, moveable vascular device for enlarging an occluded portion of a vessel. The device can be configured to allow for motion such as translating and/or slide and lock. One advantage of the axially-radially nested stent is that it maintains the expanded size, without significant recoil.

35 Claims, 26 Drawing Sheets

U.S. PATENT DOCUMENTS

| | | |
|---|---|---|
| 4,877,030 A | 10/1989 | Beck et al. |
| 4,922,905 A | 5/1990 | Strecker |
| 4,954,126 A | 9/1990 | Wallstén |
| 4,980,449 A | 12/1990 | Kohn et al. |
| 5,007,926 A | 4/1991 | Derbyshire |
| 5,040,548 A | 8/1991 | Yock |
| 5,059,211 A | 10/1991 | Stack et al. |
| 5,061,273 A | 10/1991 | Yock |
| 5,092,877 A | 3/1992 | Pinchuk |
| 5,099,060 A | 3/1992 | Kohn et al. |
| 5,108,416 A | 4/1992 | Ryan et al. |
| 5,140,094 A | 8/1992 | Kohn et al. |
| 5,151,100 A | 9/1992 | Abele et al. |
| 5,158,548 A | 10/1992 | Lau et al. |
| 5,192,307 A | 3/1993 | Wall |
| 5,194,570 A | 3/1993 | Kohn et al. |
| 5,195,984 A | 3/1993 | Schatz |
| 5,197,978 A | 3/1993 | Hess |
| 5,198,507 A | 3/1993 | Kohn et al. |
| 5,216,115 A | 6/1993 | Kohn et al. |
| 5,230,349 A | 7/1993 | Langberg |
| 5,232,445 A | 8/1993 | Bonzel |
| 5,242,399 A | 9/1993 | Lau et al. |
| 5,242,997 A | 9/1993 | Kohn et al. |
| 5,264,537 A | 11/1993 | Kohn et al. |
| 5,266,073 A | 11/1993 | Wall |
| 5,282,823 A | 2/1994 | Schwartz et al. |
| 5,300,085 A | 4/1994 | Yock |
| 5,306,286 A | 4/1994 | Stack et al. |
| 5,306,294 A | 4/1994 | Winston et al. |
| 5,317,077 A | 5/1994 | Kohn et al. |
| 5,344,426 A | 9/1994 | Lau et al. |
| 5,350,395 A | 9/1994 | Yock |
| 5,397,355 A | 3/1995 | Marin et al. |
| 5,402,554 A | 4/1995 | Oetiker |
| 5,421,955 A | 6/1995 | Lau et al. |
| 5,423,321 A | 6/1995 | Fontenot |
| 5,423,885 A | 6/1995 | Williams |
| 5,441,515 A | 8/1995 | Khosravi et al. |
| 5,443,496 A | 8/1995 | Schwartz et al. |
| 5,443,500 A | 8/1995 | Sigwart |
| 5,445,646 A | 8/1995 | Euteneur et al. |
| 5,449,382 A | 9/1995 | Dayton |
| 5,451,233 A | 9/1995 | Yock |
| 5,464,450 A | 11/1995 | Buscemi et al. |
| 5,476,508 A | 12/1995 | Amstrup |
| 5,484,449 A | 1/1996 | Amundson et al. |
| 5,490,962 A | 2/1996 | Cima et al. |
| 5,496,275 A | 3/1996 | Sirhan et al. |
| 5,496,346 A | 3/1996 | Horzewski et al. |
| 5,514,154 A | 5/1996 | Lau et al. |
| 5,527,337 A * | 6/1996 | Stack et al. .................. 606/198 |
| 5,545,135 A | 8/1996 | Iacob et al. |
| 5,545,138 A | 8/1996 | Fugoso et al. |
| 5,549,556 A | 8/1996 | Ndondo-Lay et al. |
| 5,549,662 A | 8/1996 | Fordenbacher |
| 5,551,954 A | 9/1996 | Buscemi et al. |
| 5,554,182 A | 9/1996 | Dinh et al. |
| 5,556,413 A | 9/1996 | Lam |
| 5,571,166 A | 11/1996 | Dinh et al. |
| 5,575,816 A | 11/1996 | Rudnick et al. |
| 5,578,075 A | 11/1996 | Dayton |
| 5,587,507 A | 12/1996 | Kohn et al. |
| 5,591,172 A | 1/1997 | Bachmann et al. |
| 5,591,223 A | 1/1997 | Lock et al. |
| 5,591,224 A | 1/1997 | Schwartz et al. |
| 5,591,227 A | 1/1997 | Dinh et al. |
| 5,599,352 A | 2/1997 | Dinh et al. |
| 5,603,722 A | 2/1997 | Phan et al. |
| 5,607,463 A | 3/1997 | Schwartz et al. |
| 5,618,299 A | 4/1997 | Khosravi et al. |
| 5,626,600 A | 5/1997 | Horzewski et al. |
| 5,628,785 A | 5/1997 | Schwartz et al. |
| 5,629,077 A | 5/1997 | Turnlund et al. |
| 5,632,771 A | 5/1997 | Boatman et al. |
| 5,643,312 A | 7/1997 | Fischell et al. |
| 5,643,314 A | 7/1997 | Carpenter et al. |
| 5,643,339 A | 7/1997 | Kavteladze et al. |
| 5,649,977 A | 7/1997 | Campbell |
| 5,651,174 A | 7/1997 | Schwartz et al. |
| 5,658,995 A | 8/1997 | Kohn et al. |
| 5,670,602 A | 9/1997 | Kohn et al. |
| 5,681,345 A | 10/1997 | Euteneuer |
| 5,697,967 A | 12/1997 | Dinh et al. |
| 5,707,387 A | 1/1998 | Wijay |
| 5,725,549 A | 3/1998 | Lam |
| 5,733,328 A | 3/1998 | Fordenbacher |
| 5,735,872 A | 4/1998 | Carpenter et al. |
| 5,741,293 A | 4/1998 | Wijay |
| 5,749,888 A | 5/1998 | Yock |
| 5,755,708 A | 5/1998 | Segal |
| 5,759,186 A | 6/1998 | Bachmann et al. |
| 5,766,710 A | 6/1998 | Turnlund et al. |
| 5,769,868 A | 6/1998 | Yock |
| 5,797,951 A | 8/1998 | Mueller |
| 5,799,384 A | 9/1998 | Schwartz et al. |
| 5,800,393 A | 9/1998 | Sahota |
| 5,800,507 A | 9/1998 | Schwartz |
| 5,833,707 A | 11/1998 | McIntyre et al. |
| 5,836,965 A | 11/1998 | Jendersee et al. |
| 5,849,034 A | 12/1998 | Schwartz |
| 5,851,217 A | 12/1998 | Wolff et al. |
| 5,851,231 A | 12/1998 | Wolff et al. |
| 5,855,600 A | 1/1999 | Alt |
| 5,855,802 A | 1/1999 | Acciai et al. |
| 5,868,747 A | 2/1999 | Ochoa et al. |
| 5,876,419 A | 3/1999 | Carpenter et al. |
| 5,893,840 A | 4/1999 | Hull et al. |
| 5,906,639 A | 5/1999 | Rudnick et al. |
| 5,910,816 A | 6/1999 | Fontenot et al. |
| 5,921,952 A | 7/1999 | Desmond, III et al. |
| 5,944,726 A | 8/1999 | Blaeser et al. |
| 5,951,586 A | 9/1999 | Berg et al. |
| 5,954,729 A | 9/1999 | Bachmann et al. |
| 5,957,971 A | 9/1999 | Schwartz |
| 5,976,181 A | 11/1999 | Whelan et al. |
| 5,984,963 A | 11/1999 | Ryan et al. |
| 5,989,280 A | 11/1999 | Euteneur et al. |
| 6,007,545 A | 12/1999 | Venturelli |
| 6,015,387 A | 1/2000 | Schwartz et al. |
| 6,019,785 A | 2/2000 | Strecker |
| 6,033,436 A * | 3/2000 | Steinke et al. ................ 623/1.15 |
| 6,036,715 A | 3/2000 | Yock |
| 6,048,521 A | 4/2000 | Kohn et al. |
| 6,080,190 A | 6/2000 | Schwartz |
| 6,093,157 A | 7/2000 | Chandrasekaran |
| 6,120,491 A | 9/2000 | Kohn et al. |
| 6,125,523 A | 10/2000 | Brown et al. |
| 6,132,457 A | 10/2000 | Chobotov |
| 6,160,084 A | 12/2000 | Langer et al. |
| 6,171,334 B1 | 1/2001 | Cox |
| 6,179,878 B1 | 1/2001 | Duerig et al. |
| 6,183,503 B1 | 2/2001 | Hart et al. |
| 6,190,403 B1 | 2/2001 | Fishchell et al. |
| 6,197,789 B1 | 3/2001 | Grainger |
| 6,214,037 B1 | 4/2001 | Mitchell et al. |
| 6,224,626 B1 | 5/2001 | Steinke |
| 6,238,430 B1 | 5/2001 | Klumb et al. |
| 6,258,117 B1 | 7/2001 | Camrud et al. |
| 6,262,079 B1 | 7/2001 | Grainger et al. |
| 6,264,624 B1 | 7/2001 | Desmond, III et al. |
| 6,264,672 B1 | 7/2001 | Fisher |
| 6,280,473 B1 | 8/2001 | Lemperle et al. |
| 6,283,983 B1 | 9/2001 | Makower et al. |
| 6,284,862 B1 | 9/2001 | Kohn et al. |
| 6,287,329 B1 | 9/2001 | Duerig et al. |
| 6,287,333 B1 | 9/2001 | Appling et al. |
| 6,302,907 B1 | 10/2001 | Hijlkema |
| 6,309,350 B1 | 10/2001 | Van Tassel et al. |
| 6,319,277 B1 | 11/2001 | Rudnick et al. |
| 6,319,492 B1 | 11/2001 | Kohn et al. |
| 6,322,586 B1 | 11/2001 | Monroe et al. |
| 6,350,277 B1 | 2/2002 | Kocur |
| 6,359,102 B1 | 3/2002 | Kemnitzer et al. |
| 6,383,211 B1 | 5/2002 | Staehle |
| 6,388,043 B1 | 5/2002 | Langer et al. |
| 6,391,032 B2 | 5/2002 | Blaeser et al. |

| | | |
|---|---|---|
| 6,409,750 B1 | 6/2002 | Hyodoh et al. |
| 6,409,752 B1 | 6/2002 | Boatman et al. |
| 6,447,508 B1 | 9/2002 | Sharkey et al. |
| 6,451,034 B1 | 9/2002 | Gifford, III et al. |
| 6,475,477 B1 | 11/2002 | Kohn et al. |
| 6,485,510 B1 | 11/2002 | Camrud et al. |
| 6,488,700 B2 | 12/2002 | Klumb et al. |
| 6,491,704 B2 | 12/2002 | Gifford, III et al. |
| 6,491,705 B2 | 12/2002 | Gifford, III et al. |
| 6,491,938 B2 | 12/2002 | Kunz et al. |
| 6,527,791 B2 | 3/2003 | Fisher |
| 6,530,940 B2 | 3/2003 | Fisher |
| 6,530,958 B1 | 3/2003 | Cima et al. |
| 6,562,021 B1 | 5/2003 | Derbin et al. |
| 6,565,582 B2 | 5/2003 | Gifford, III et al. |
| 6,565,596 B1 | 5/2003 | White et al. |
| 6,569,191 B1 | 5/2003 | Hogan |
| 6,569,441 B2 | 5/2003 | Kunz et al. |
| 6,582,458 B1 | 6/2003 | White et al. |
| 6,582,472 B2 | 6/2003 | Hart |
| 6,602,497 B1 | 8/2003 | Kohn et al. |
| 6,607,551 B1 | 8/2003 | Sullivan et al. |
| 6,613,073 B1 | 9/2003 | White et al. |
| 6,620,356 B1 | 9/2003 | Wong et al. |
| 6,623,491 B2 | 9/2003 | Thompson |
| 6,623,518 B2 | 9/2003 | Thompson et al. |
| 6,623,521 B2 * | 9/2003 | Steinke et al. ............... 623/1.16 |
| 6,645,143 B2 | 11/2003 | Van Tassel et al. |
| 6,652,555 B1 | 11/2003 | Van Tassel et al. |
| 6,659,105 B2 | 12/2003 | Burbank et al. |
| 6,676,658 B2 | 1/2004 | Burbank et al. |
| 6,682,541 B1 | 1/2004 | Gifford, III et al. |
| 6,685,736 B1 | 2/2004 | White et al. |
| 6,689,153 B1 | 2/2004 | Skiba |
| 6,689,158 B1 | 2/2004 | White et al. |
| 6,695,857 B2 | 2/2004 | Gifford, III et al. |
| 6,699,257 B2 | 3/2004 | Gifford, III et al. |
| 6,699,280 B2 | 3/2004 | Camrud et al. |
| 6,709,449 B2 | 3/2004 | Camrud et al. |
| 6,720,402 B2 | 4/2004 | Langer et al. |
| 6,736,838 B1 | 5/2004 | Richter |
| 6,746,477 B2 | 6/2004 | Moore |
| 6,749,627 B2 | 6/2004 | Thompson et al. |
| 6,786,922 B2 | 9/2004 | Schaeffer |
| 6,790,221 B2 | 9/2004 | Monroe et al. |
| 6,792,979 B2 | 9/2004 | Konya et al. |
| 6,802,849 B2 | 10/2004 | Blaeser et al. |
| 6,821,292 B2 | 11/2004 | Pazienza et al. |
| 6,852,308 B2 | 2/2005 | Kohn et al. |
| 6,869,143 B2 | 3/2005 | Secord |
| 6,878,159 B2 | 4/2005 | Iwasaka et al. |
| 6,916,868 B2 | 7/2005 | Kemnitzer et al. |
| 6,951,053 B2 | 10/2005 | Padilla et al. |
| 6,962,604 B2 | 11/2005 | Hijlkema |
| 6,964,680 B2 | 11/2005 | Shanley |
| 6,974,472 B2 | 12/2005 | Hong et al. |
| 6,974,475 B1 | 12/2005 | Wall |
| 6,991,647 B2 | 1/2006 | Jadhav |
| 7,041,126 B2 | 5/2006 | Shin et al. |
| 7,056,493 B2 | 6/2006 | Kohn et al. |
| 7,128,756 B2 | 10/2006 | Lowe et al. |
| 7,141,063 B2 | 11/2006 | White et al. |
| 7,175,653 B2 | 2/2007 | Gaber |
| 7,229,473 B2 | 6/2007 | Falotico et al. |
| 7,329,277 B2 | 2/2008 | Addonizio et al. |
| 7,704,275 B2 | 4/2010 | Schmid et al. |
| 2001/0010015 A1 | 7/2001 | Hijlkema |
| 2001/0020173 A1 | 9/2001 | Klumb et al. |
| 2001/0029378 A1 | 10/2001 | Blaeser et al. |
| 2001/0044651 A1 * | 11/2001 | Steinke et al. ............... 623/1.16 |
| 2002/0010504 A1 | 1/2002 | Alt et al. |
| 2002/0040238 A1 | 4/2002 | Rudnick et al. |
| 2002/0052641 A1 | 5/2002 | Monroe et al. |
| 2002/0072656 A1 | 6/2002 | Van Tassel et al. |
| 2002/0077693 A1 | 6/2002 | Barclay et al. |
| 2002/0095204 A1 | 7/2002 | Thompson et al. |
| 2002/0120322 A1 | 8/2002 | Thompson et al. |
| 2002/0120323 A1 | 8/2002 | Thompson et al. |
| 2002/0123791 A1 | 9/2002 | Harrison |
| 2002/0138081 A1 | 9/2002 | Blaeser et al. |
| 2002/0138126 A1 | 9/2002 | Camrud et al. |
| 2002/0147489 A1 | 10/2002 | Hong et al. |
| 2002/0156456 A1 | 10/2002 | Fisher |
| 2002/0156457 A1 | 10/2002 | Fisher |
| 2002/0193870 A1 | 12/2002 | Jang |
| 2003/0045923 A1 | 3/2003 | Bashiri |
| 2003/0074043 A1 | 4/2003 | Thompson |
| 2003/0078649 A1 | 4/2003 | Camrud et al. |
| 2003/0120334 A1 | 6/2003 | Gerberding |
| 2003/0176914 A1 | 9/2003 | Rabkin et al. |
| 2003/0199969 A1 * | 10/2003 | Steinke et al. ............... 623/1.16 |
| 2003/0208262 A1 | 11/2003 | Gaber |
| 2003/0211135 A1 | 11/2003 | Greenhalgh et al. |
| 2003/0212451 A1 | 11/2003 | Cox et al. |
| 2003/0220682 A1 | 11/2003 | Kujawski |
| 2004/0054400 A1 | 3/2004 | Granada |
| 2004/0062788 A1 | 4/2004 | Richter |
| 2004/0068316 A1 | 4/2004 | Schaeffer |
| 2004/0086458 A1 | 5/2004 | Kohn et al. |
| 2004/0086462 A1 | 5/2004 | Kohn et al. |
| 2004/0093073 A1 | 5/2004 | Lowe et al. |
| 2004/0097959 A1 | 5/2004 | Thompson |
| 2004/0106971 A1 | 6/2004 | Schwartz et al. |
| 2004/0106977 A1 | 6/2004 | Sullivan et al. |
| 2004/0127971 A1 * | 7/2004 | Padilla et al. ............... 623/1.15 |
| 2004/0133260 A1 | 7/2004 | Schwartz et al. |
| 2004/0143319 A1 | 7/2004 | Schwartz et al. |
| 2004/0167616 A1 | 8/2004 | Camrud et al. |
| 2004/0186551 A1 | 9/2004 | Kao et al. |
| 2004/0191175 A1 | 9/2004 | Kohn et al. |
| 2004/0193251 A1 | 9/2004 | Rudnick et al. |
| 2004/0224003 A1 | 11/2004 | Schultz |
| 2004/0236401 A1 | 11/2004 | Shin et al. |
| 2004/0243217 A1 | 12/2004 | Andersen et al. |
| 2004/0243218 A1 | 12/2004 | Schaeffer |
| 2005/0038503 A1 | 2/2005 | Greenhalgh et al. |
| 2005/0106119 A1 | 5/2005 | Brandom et al. |
| 2005/0123481 A1 | 6/2005 | Kohn et al. |
| 2005/0165203 A1 | 7/2005 | Kohn et al. |
| 2005/0203615 A1 * | 9/2005 | Forster et al. ............... 623/2.11 |
| 2006/0020324 A1 * | 1/2006 | Schmid et al. ............... 623/1.16 |
| 2006/0024266 A1 | 2/2006 | Brandom et al. |
| 2006/0026815 A1 | 2/2006 | Padilla et al. |
| 2006/0034769 A1 | 2/2006 | Kohn et al. |
| 2006/0036316 A1 | 2/2006 | Zeltinger et al. |
| 2006/0115449 A1 | 6/2006 | Pacetti |
| 2006/0136041 A1 | 6/2006 | Schmid et al. |
| 2006/0182779 A1 | 8/2006 | Brandom et al. |
| 2006/0204440 A1 | 9/2006 | Kohn et al. |
| 2007/0010870 A1 | 1/2007 | Alt et al. |
| 2007/0032854 A1 | 2/2007 | Schmid et al. |
| 2007/0032857 A1 | 2/2007 | Schmid et al. |
| 2007/0061004 A1 | 3/2007 | Steinke |
| 2007/0142901 A1 | 6/2007 | Steinke |
| 2008/0051868 A1 | 2/2008 | Cottone et al. |
| 2008/0051873 A1 | 2/2008 | Cottone et al. |
| 2008/0051874 A1 | 2/2008 | Cottone et al. |
| 2008/0051875 A1 | 2/2008 | Cottone et al. |
| 2008/0071355 A1 | 3/2008 | Weber |
| 2008/0183275 A1 | 7/2008 | Schmid et al. |
| 2009/0030501 A1 | 1/2009 | Morris et al. |
| 2009/0143853 A1 | 6/2009 | Morris et al. |

FOREIGN PATENT DOCUMENTS

| | | |
|---|---|---|
| JP | 9-313617 | 12/1997 |
| WO | WO 90/14046 A1 | 11/1990 |
| WO | WO 94/21196 A2 | 9/1994 |
| WO | WO 94/21196 A3 | 2/1995 |
| WO | WO 96/14030 A1 | 5/1996 |
| WO | WO 97/07751 A1 | 3/1997 |
| WO | WO 97/42911 A1 | 11/1997 |
| WO | WO 98/22045 | 5/1998 |
| WO | WO 98/22073 A2 | 5/1998 |
| WO | WO 98/22073 A3 | 2/1999 |
| WO | WO 99/08740 A1 | 2/1999 |
| WO | WO 99/15106 A1 | 4/1999 |
| WO | WO 99/40874 A1 | 8/1999 |
| WO | WO 99/65421 A2 | 12/1999 |

| | | |
|---|---|---|
| WO | WO 96/65421 A3 | 1/2000 |
| WO | WO 00/09195 A1 | 2/2000 |
| WO | WO 00/10623 A1 | 3/2000 |
| WO | WO 00/30565 A1 | 6/2000 |
| WO | WO 00/59405 A1 | 10/2000 |
| WO | WO 00/62708 A1 | 10/2000 |
| WO | WO 00/71058 A1 | 11/2000 |
| WO | WO 01/24735 A1 | 4/2001 |
| WO | WO 01/35864 A1 | 5/2001 |
| WO | WO 01/51114 A2 | 7/2001 |
| WO | WO 01/70298 A2 | 9/2001 |
| WO | WO 01/87180 A2 | 11/2001 |
| WO | WO 01/51114 A3 | 1/2002 |
| WO | WO 01/70298 A3 | 2/2002 |
| WO | WO 00/62708 C2 | 6/2002 |
| WO | WO 01/87180 A3 | 6/2002 |
| WO | WO 02/47582 A2 | 6/2002 |
| WO | WO 02/053204 A2 | 7/2002 |
| WO | WO 02/054990 A2 | 7/2002 |
| WO | WO 02/047582 A3 | 10/2002 |
| WO | WO 02/054990 A3 | 11/2002 |
| WO | WO 02/053204 A3 | 3/2003 |
| WO | WO 03/022178 A1 | 3/2003 |
| WO | WO 03/047464 A2 | 6/2003 |
| WO | WO 03/057076 A1 | 7/2003 |
| WO | WO 03/047464 A3 | 9/2003 |
| WO | WO 03/047464 C2 | 11/2003 |
| WO | WO 03/094798 A1 | 11/2003 |
| WO | WO 03/099161 A2 | 12/2003 |
| WO | WO 03/099161 A3 | 2/2004 |
| WO | WO 2004/019820 A1 | 3/2004 |
| WO | WO 2004/026112 A2 | 4/2004 |
| WO | WO 2004/032803 A1 | 4/2004 |
| WO | WO 2004/026112 C2 | 6/2004 |
| WO | WO 2004/026112 A3 | 10/2004 |
| WO | WO 2004/087015 | 10/2004 |
| WO | WO 2004/096340 A1 | 11/2004 |
| WO | WO 2004/110312 A1 | 12/2004 |
| WO | WO 2006/010636 A1 | 2/2006 |
| WO | WO 2006/014596 A1 | 2/2006 |
| WO | WO 2006/020616 A1 | 2/2006 |
| WO | WO 2006/107608 A1 | 10/2006 |
| WO | WO 2007/084444 A2 | 7/2007 |
| WO | WO 2010/022005 | 2/2010 |
| WO | WO 2010/042879 | 4/2010 |

OTHER PUBLICATIONS

Autieri, M.V. et al. "Antisense oligonucleotides to the p65 subunit of NF-Kb inhibit human vascualr smooth muscle cell adherence and proliferation and prevent neointima formation in rat carotid arteries," Biochemical and Biophysical Research Communications 213: 827-836, 1995.

Brauner, R. "Controlled periadverntitial administration of verapamil inhibits neointimal smooth muscle cell proliferation and ameliorates vasomotor abnormalities in experimental vein bypass grafts," The Journal of Thoracic and Cardiovascular Surgery 114: 53-63, 1997.

Carmeliet, P. et al. "Inhibitory role of plasminogen activator inhibitor-1 in arterial wound healing and neointima formation," Circulation 96: 3180-3191, 1997.

Epstein, S.E. et al. "Cytotoxic effects of a recombinant chimeric toxin on rapidly proliferating vascular smooth muscle cells," Circulation 84: 778-787, 1991.

Hu, Y. "Inhibition of neointima hyperplasia of mouse vein grafts by locally applied suramin," Circulation 100: 861-868, 1999.

Kurisu, Y. et al. "Protective effect of beraprost sodium, a stable prostacyclin analogue, on cardiac allograft vasculopathy in rats," Hiroshima Journal of Medical Science 56: 11-19, 1997.

Morishita, R. et al. "Novel in vitro gene transfer method for study of local modulators in vascular smooth muscle cells," Hypertension 21: 894-899, 1993.

Nerem, R.M. et al. "Tissue engineering and the vascular system, synthetic biodegradable polymer scaffolds," pp. 164-185, 1997.

Von Der Leyen, H.E. et al. "Gene therapy neointimal vascular lesion: in vivo transfer of endothelial cell nitric oxide synthase gene," PNAS USA 92:1137-1141, 1995.

Yasukawa, H. "Inhibition of intimal hyperplasia after balloon injury by antibodies to intercellular adhesion molecule-1 and lymphocyte funtion, Associated antigen-1," Circulation 95: 1515-1522, 1997.

Balcon, R. et al., Recommendations on stent manufacture, implantation and utilization, European Heart Journal, Oct. 1997, vol. 18, pp. 1536-1547.

Charles, Roger et al., Ceramide-Coated Balloon Catheters Limit Neointimal Hyperplasia After Stretch Injury in Carotid Arteries, Circulation Research, 2000; 87; pp. 282-288.

Coroneos, Emmanuel et al., Differential Regulation of Sphingomyelinase and Ceramidase Activities by Growth Factors and Cytokines, The Journal of Biological Chemistry, Oct. 6, 1995, vol. 270, No. 40, pp. 23305-23309.

Coroneos, Emmanuel et al., Sphingolipid metabolites differentially regulate extracellular signal-regulated kinase and stress-activated protein kinase cascades, Biochem. J., 1196; 316, pp. 13-17 (Printed in Great Britain).

Jacobs, Leila S. et al., Sphingolipids as mediators of effects of platelet-derived growth factor in vascular smooth muscle cells, Am J Physiol (American Physiological Society), 1993, pp. C740-C747.

Tanguay, Jean Francois et al., Current Status of Biodegradable Stents, Cardiology Clinics, Contemporary Interventional Techniques, Nov. 1994, vol. 12, No. 4, pp. 699-713, W.B. Saunders Company.

Nikol, S. et al., Molecular biology and post-angioplasty restenosis, Atherosclerosis, 1996; 123, pp. 17-31.

Phillips, Paul S. MD, et al., The Stenter's Notebook, 1998, (entire book), Physicians' Press, Birmingham, Michigan.

Ratner, Buddy D. et al., Biomaterials Science, An Introduction to Materials in Medicine, 2nd Edition, 2004, (entire book), Elsevier Acadmeic Press.

Serruys, Patrick W. et al., Handbook of Coronary Stents, Fourth Edition, 2002, (entire book), Martin Dunitz Ltd.

Atala, Anthony et al., Synthetic Biodegradable Polymer Scaffolds, 1997, (entire book), Birkhauser Boston.

International Search Report and Written Opinion in related International Application No. PCT/US2007/86422, mailed Aug. 18, 2008, in 18 pages.

International Search Report and Written Opinion received in corresponding PCT Application No. PCT/US07/86422, mailed Aug. 18, 2008, 18 pages.

* cited by examiner

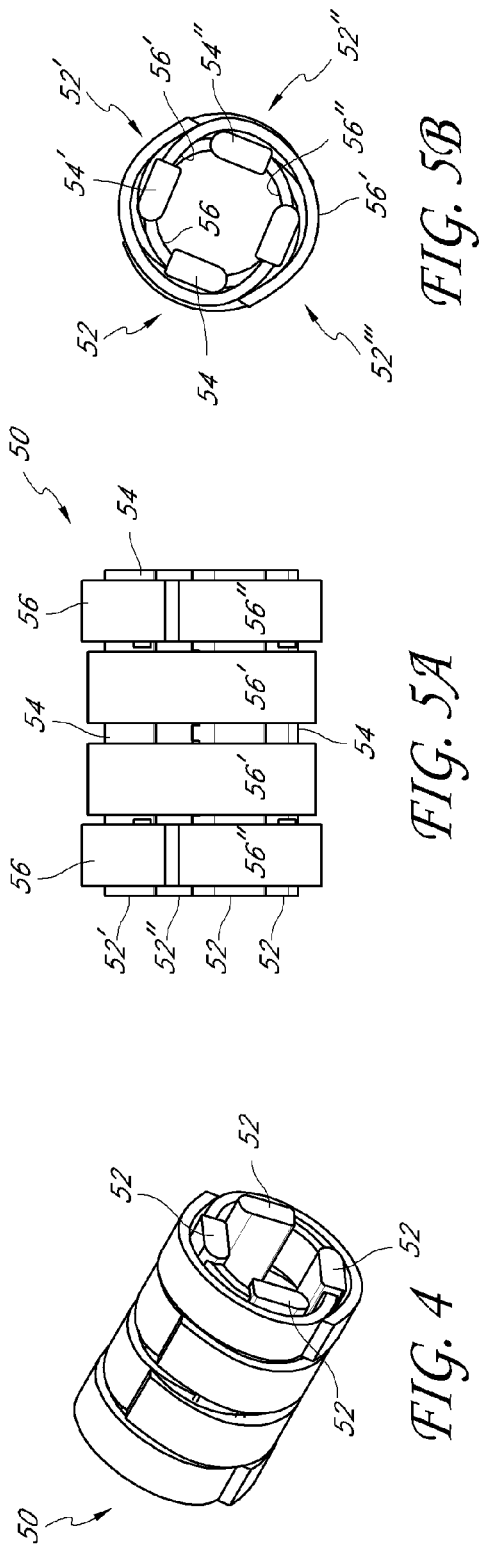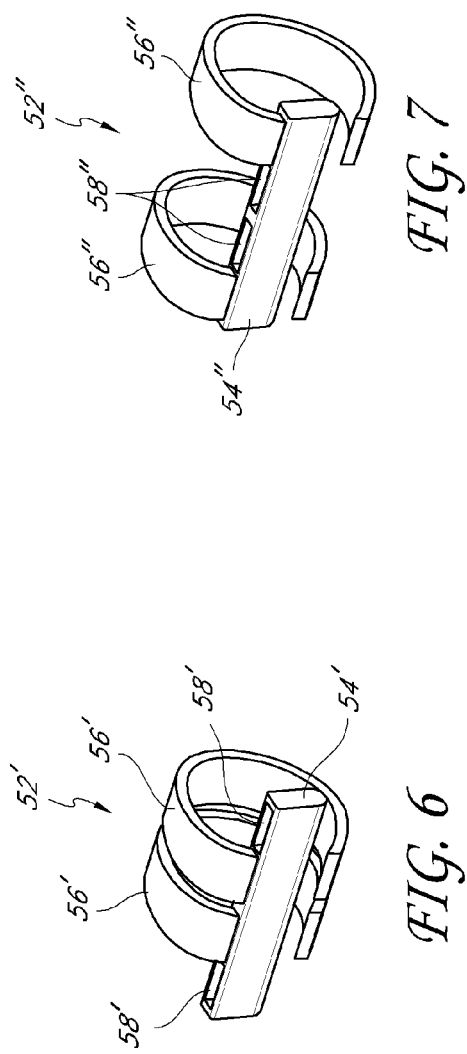

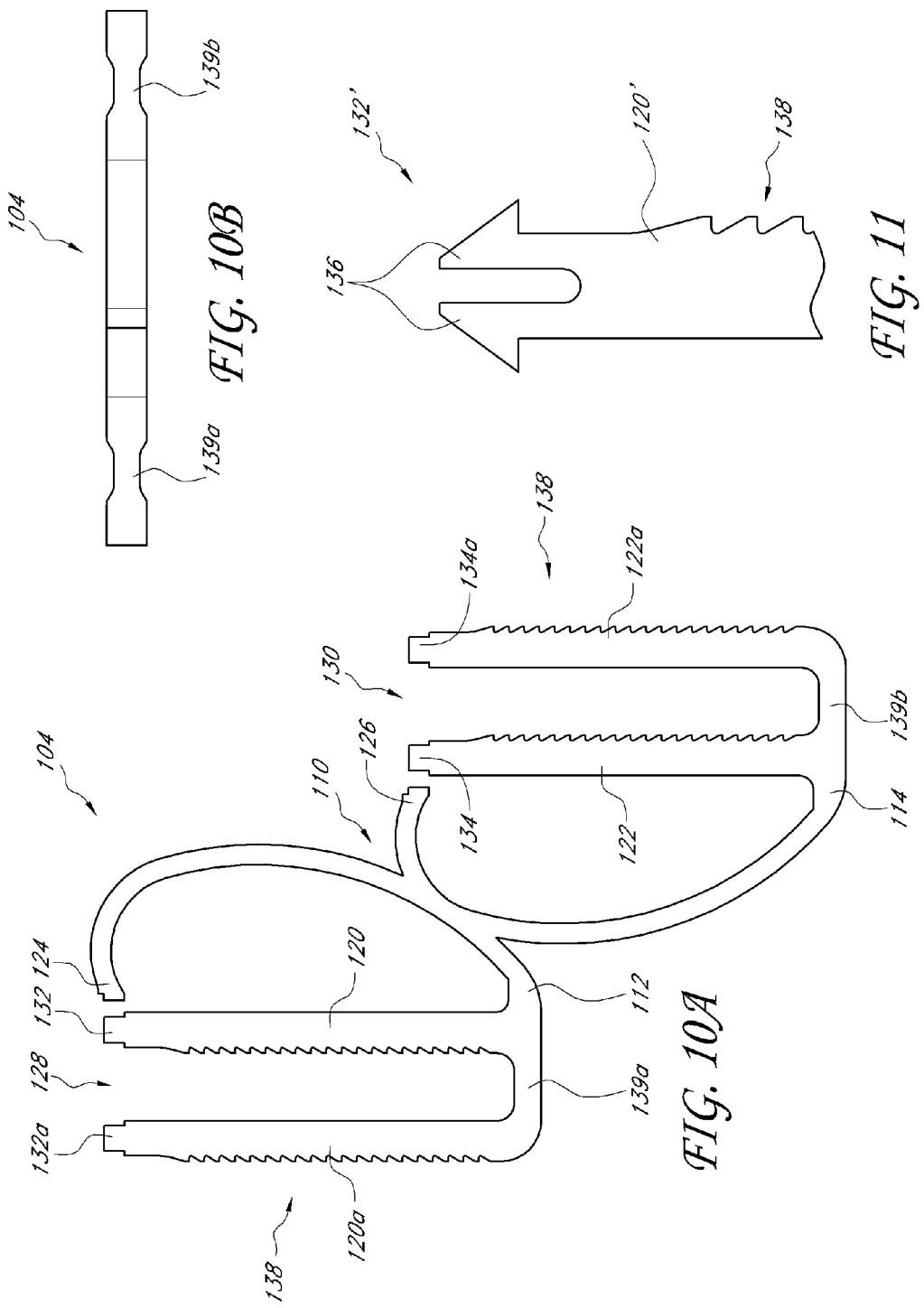

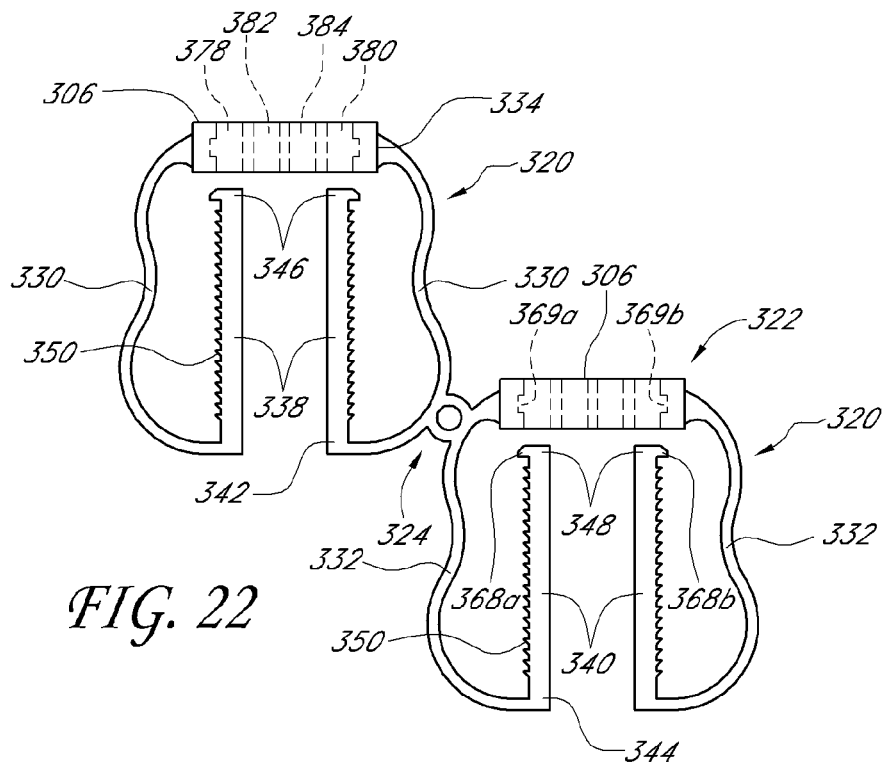
FIG. 22
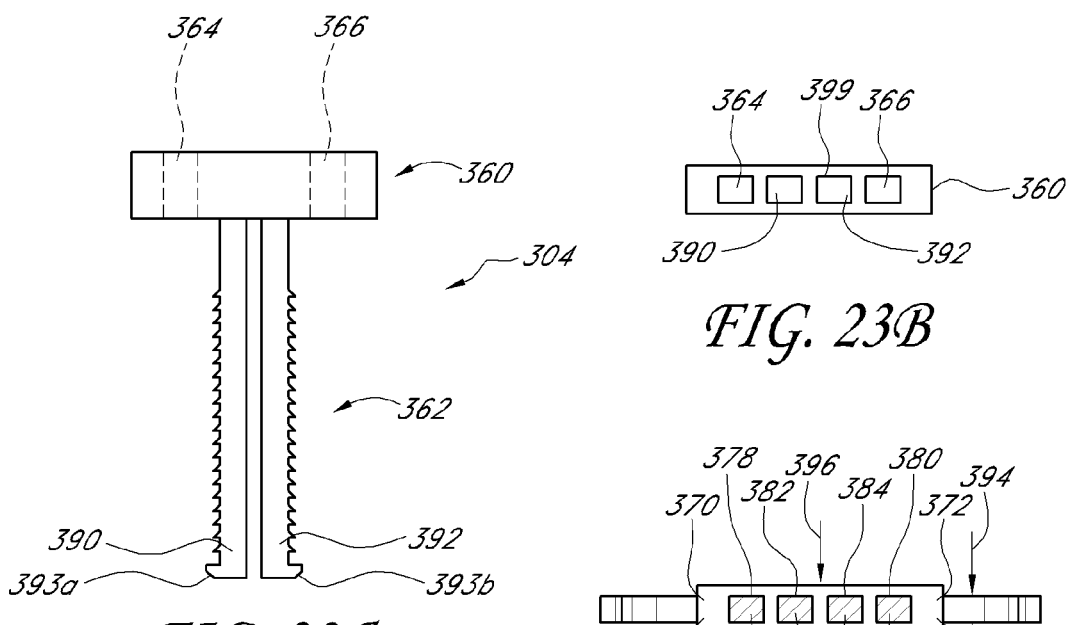
FIG. 23A
FIG. 23B
FIG. 24

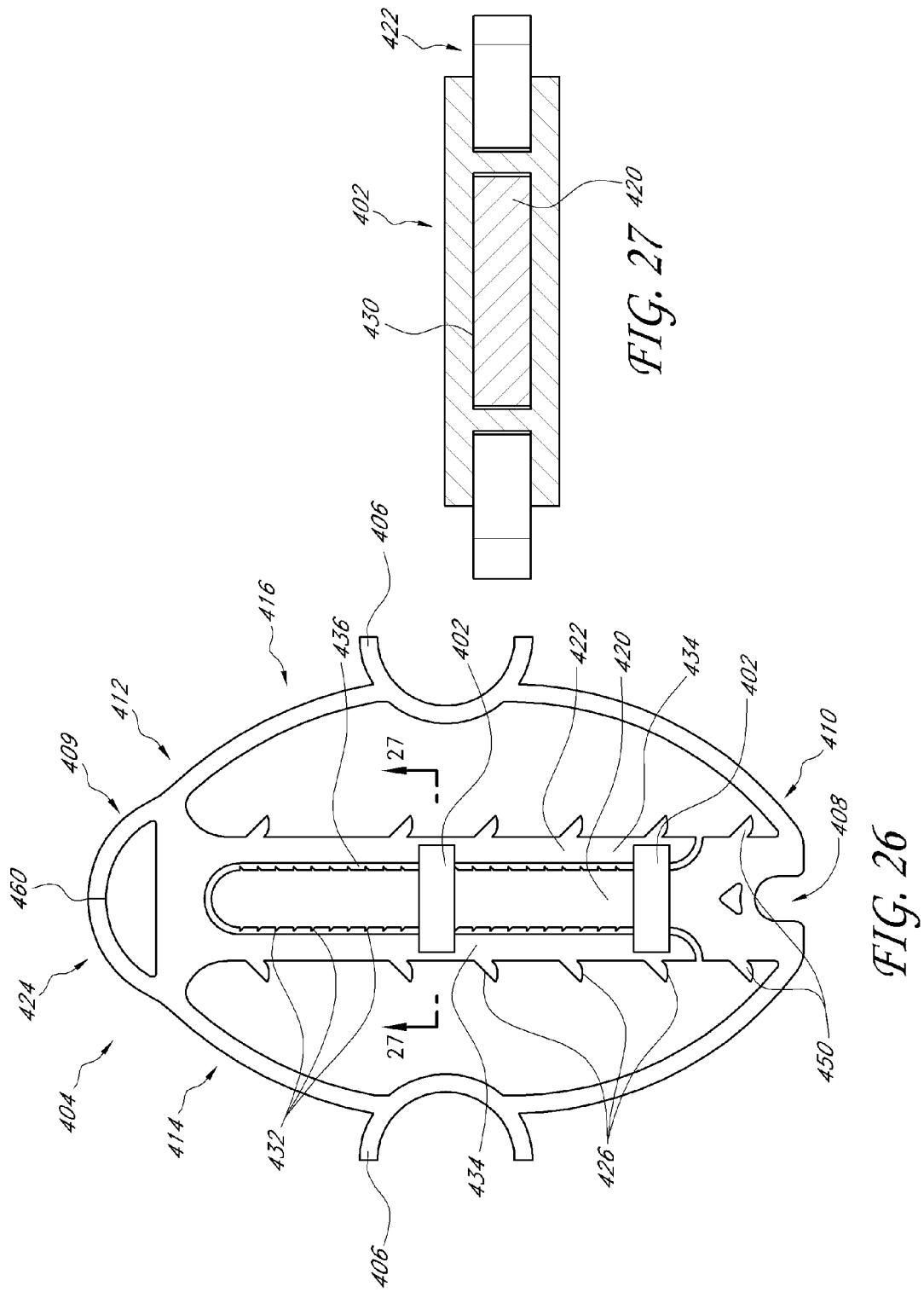

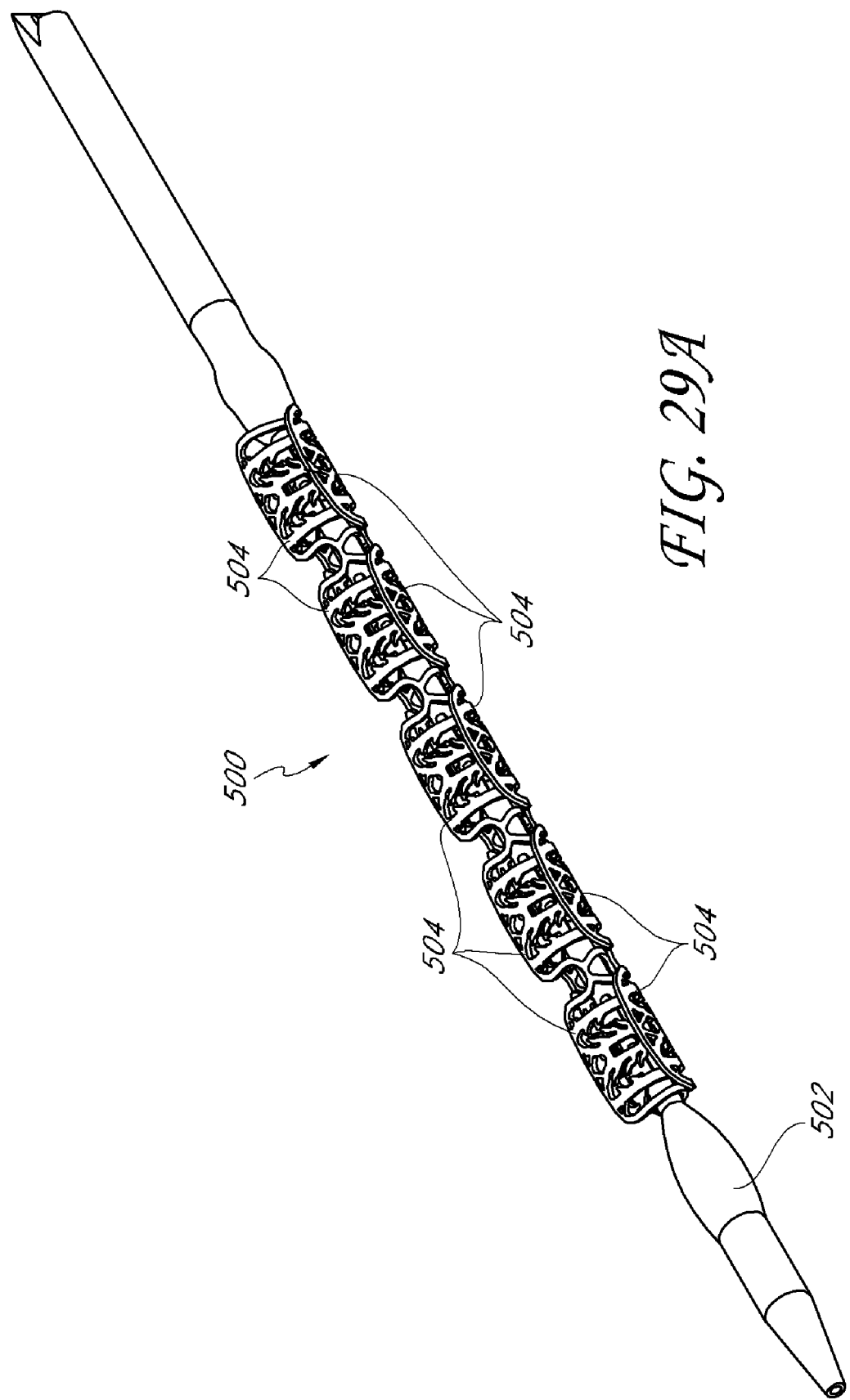

AXIALLY-RADIALLY NESTED EXPANDABLE DEVICE

This application claims the benefit of U.S. Patent Application No. 60/991,481, filed Nov. 30, 2007, the entirety of which is hereby incorporated herein by reference.

BACKGROUND

1. Field of the Inventions

The present inventions relate generally to expandable medical implants for maintaining support of a body lumen, and more particularly, to a predominantly axially-radially nested, diametrically expandable, moveable device for enlarging a portion of a body lumen.

2. Description of the Related Art

Stents or expandable stent grafts are implanted in a variety of body lumens in an effort to maintain their patency. The body lumens no matter how large or small can be vascular and nonvascular. These devices are typically intraluminally implanted by use of a catheter, which is inserted at an easily accessible location and then advanced to the deployment site. The stent is initially in a radially compressed or collapsed state to enable it to be maneuvered through the lumen. Once in position, the stent is deployed which, depending on its configuration, can be achieved either automatically or manually, by for example, the inflation of a balloon about which the stent is carried on the catheter.

An important and frequent use of stents is the treatment of blood vessels in situations where part of the vessel wall or stenotic plaque blocks or occludes fluid flow in the vessel. Often, a balloon catheter is utilized in a percutaneous transluminal coronary angioplasty procedure to enlarge the occluded portion of the vessel. However, the dilation of the occlusion can cause fissuring of atherosclerotic plaque and damage to the endothelium and underlying smooth muscle cell layer, potentially leading to immediate problems from flap formation or perforations in the vessel wall, as well as long-term problems with restenosis of the dilated vessel. Implantation of stents can provide support for such problems and prevent re-closure of the vessel or provide patch repair for a perforated vessel. Further, the stent can overcome the tendency of diseased vessel walls to collapse, thereby maintaining a more normal flow of blood through that vessel. Stents are also now being used in other clinical conditions such as in patients with unstable vulnerable plaque lesions.

As stents are normally employed to hold open an otherwise blocked, constricted or occluded lumen, a stent must exhibit sufficient radial or hoop strength in its expanded state to effectively counter the anticipated forces. Additionally, it can be beneficial for the stent to be as compact as possible in its collapsed state in order to facilitate its advancement through the lumen. As a result, it is advantageous for a stent to have as large an expansion ratio as possible.

An additional consideration is the longitudinal flexibility of the device. Such characteristic is important not only in maneuvering the stent into position, which can require the traversal of substantial convolutions of the vasculature, but also to better conform to any curvature of the vasculature at the deployment site. At the same time it is, however, necessary for the stent to nonetheless exhibit sufficient radial strength to provide the necessary support for the lumen walls upon deployment.

A number of very different approaches have been previously devised in an effort to address these various requirements. A popular approach calls for the stent to be constructed wholly of wire. The wire is bent, woven and/or coiled to define a generally cylindrical structure in a configuration that has the ability to undergo radial expansion. The use of wire has a number of disadvantages associated therewith including for example, its substantially constant cross-section which can cause greater or lesser than an ideal amount of material to be concentrated at certain locations along the stent. Additionally, wire has limitations with respect to the shapes it can be formed into thus limiting the expansion ratio, coverage area, flexibility and strength that can ultimately be attained therewith.

As an alternative to wire-based structures, stents have been constructed from tube stock. By selectively removing material from such tubular starting material, a desired degree of flexibility and expandability can be imparted to the structure. Etching techniques as well as laser-cutting processes are utilized to remove material from the tube. Laser cutting provides for a high degree of precision and accuracy with which very well defined patterns of material can be removed from the tube to conversely leave very precisely and accurately defined patterns of material in tact. The performance of such stent is very much a function of the pattern of material which remains (i.e., design) and material thickness. The selection of a particular pattern can have a profound effect on the coverage area, expansion ratio and strength of the resulting stent as well as its longitudinal flexibility and longitudinal dimensional stability during expansion.

While the tube-based stents offer many advantages over the wire-based designs, it is nonetheless desirable to improve upon such designs in an effort to further enhance longitudinal flexibility and longitudinal dimensional stability during radial expansion without sacrificing radial hoop strength.

One stent design described by Fordenbacher, see e.g., U.S. Pat. Nos. 5,549,662 and 5,733,328, employs a plurality of elongated parallel stent components, each having a longitudinal backbone that spans the entire axial length of the stent and a plurality of opposing circumferential elements or fingers extending therefrom. The circumferential elements from one stent component weave into paired slots in the longitudinal backbone of an adjacent stent component. This weave-like interlocking configuration, wherein a circumferential element passes through the first slot in a pair and then weaves back through the second slot in the pair, is essential to Fordenbacher's goal of permitting radial expansion without material deformation. In addition, sufficient members of circumferential elements in the Fordenbacher stent can provide adequate scaffolding. Unfortunately, the circumferential elements have free ends, protruding from the paired slots. Moreover, the circumferential elements weaving through the paired slots also necessarily stand off from the lumen wall. Both the free ends and the stand off can pose significant risks of thrombosis and/or restenosis. Moreover, this stent design would tend to be rather inflexible as a result of the plurality of longitudinal backbones.

Some stents employ "jelly roll" designs, wherein a sheet is rolled upon itself with a high degree of overlap in the collapsed state and a decreasing overlap as the stent unrolls to an expanded state. Examples of such designs are described in U.S. Pat. No. 5,421,955 to Lau, U.S. Pat. Nos. 5,441,515 and 5,618,299 to Khosravi, and U.S. Pat. No. 5,443,500 to Sigwart. The disadvantage of these designs is that they tend to exhibit very poor longitudinal flexibility. In a modified design that exhibits improved longitudinal flexibility, multiple short rolls are coupled longitudinally. See e.g., U.S. Pat. No. 5,649,977 to Campbell and U.S. Pat. Nos. 5,643,314 and 5,735,872 to Carpenter. However, these coupled rolls lack vessel support between adjacent rolls. Furthermore, these designs exhibit extensive overlapping of stent elements in multiple layers, which makes the delivery profile rather thick.

Various types of stents, including those referenced above, are often described based on their means for expansion. For additional information, a variety of stents types are described by Balcon et al., "Recommendations on Stent Manufacture, Implantation and Utilization," European Heart Journal (1997), vol. 18, pages 1536-1547, and Phillips, et al., "The Stenter's Notebook," Physician's Press (1998), Birmingham, Mich.

Balloon expandable stents are manufactured in the collapsed condition and are expanded to a desired diameter with a balloon. The expandable stent structure can be held in the expanded condition by mechanical deformation of the stent as taught in, for example, U.S. Pat. No. 4,733,665 to Palmaz. Alternatively, balloon expandable stents can be held in the expanded condition by engagement of the stent walls with respect to one another as disclosed in, for example, U.S. Pat. No. 4,740,207 to Kreamer, U.S. Pat. No. 4,877,030 to Beck et al., and U.S. Pat. No. 5,007,926 to Derbyshire. Further still, the stent can be held in the expanded condition by one-way engagement of the stent walls together with tissue growth into the stent, as disclosed in U.S. Pat. No. 5,059,211 to Stack et al.

Although balloon expandable stents are the first stent type to be widely used in clinical applications, it is well recognized that current balloon expandable stents have a variety of shortcomings which can limit their effectiveness in many important applications. For example, these balloon expandable stents often exhibit substantial recoil (i.e., a reduction in diameter) immediately following deflation of the inflatable balloon. Accordingly, it can be necessary to over-inflate the balloon during deployment of the stent to compensate for the subsequent recoil. This is disadvantageous because it has been found that over-inflation can damage the blood vessel. Furthermore, a deployed balloon expandable stent can exhibit chronic recoil over time, thereby reducing the patency of the lumen. Still further, balloon expandable stents often exhibit foreshortening (i.e., a reduction in length) during expansion, thereby creating undesirable stresses along the vessel wall and making stent placement less precise. Still further, many balloon expandable stents, such as the original Palmaz-Schatz stent and later variations, are configured with an expandable mesh having relatively jagged terminal prongs, which increases the risk of injury to the vessel, thrombosis and/or restenosis.

Self-expanding stents are manufactured with a diameter approximately equal to, or larger than, the vessel diameter and are collapsed and constrained at a smaller diameter for delivery to the treatment site. Self-expanding stents are commonly placed within a sheath or sleeve to constrain the stent in the collapsed condition during delivery. After the treatment site is reached, the constraint mechanism is removed and the stent self-expands to the expanded condition. Most commonly, self-expanding stents are made of Nitinol or other shape memory alloy. One of the first self-expanding stents used clinically is the braided "WallStent," as described in U.S. Pat. No. 4,954,126 to Wallsten. Another example of a self-expanding stent is disclosed in U.S. Pat. No. 5,192,307 to Wall wherein a stent-like prosthesis is formed of plastic or sheet metal that is expandable or contractible for placement. Finally, U.S. Pat. No. 6,964,680 B2 to Shanley discloses an expandable medical device with a tapered hinge.

Heat expandable stents are similar in nature to self-expanding stents. However, this type of stent utilizes the application of heat to produce expansion of the stent structure. Stents of this type can be formed of a shape memory alloy, such as Nitinol or other materials, such as polymers, that must go through a thermal transition to achieve a dimensional change. Heat expandable stents are often delivered to the affected area on a catheter capable of receiving a heated fluid. Heated saline or other fluid can be passed through the portion of the catheter on which the stent is located, thereby transferring heat to the stent and causing the stent to expand. However, heat expandable stents have not gained widespread popularity due to the complexity of the devices, unreliable expansion properties and difficulties in maintaining the stent in its expanded state. Still further, it has been found that the application of heat during stent deployment can damage the blood vessel.

In summary, although a wide variety of stents have been proposed over the years for maintaining the patency of a body lumen, none of the existing schemes has been capable of overcoming most or all of the above described shortcomings. As a result, clinicians are forced to weigh advantages against shortcomings when selecting a stent type to use in a particular application.

SUMMARY

In accordance with an aspect of at least one of the embodiments disclosed herein is the realization that there is a need for an improved stent that is compact and flexible enough when collapsed to permit uncomplicated delivery to the affected area; that is sufficiently flexible upon deployment to conform to the shape of the affected body lumen; that expands uniformly to a desired diameter; that maintains the expanded size, without significant recoil; and that has sufficient scaffolding to provide a clear through-lumen.

One of the key aspects of various stent embodiments disclosed herein is that the stent is provided with an axially-radially nested stent design in which the elements and/or components of the stent employ a combination of the two major types of nesting. For example, elements and/or components of the stent can be "axially" nested, i.e. side by side along the axis of the stent, while the stent is in the non-deployed state in order to greatly reduce non-deployed profile. Further, portions of the elements and/or components can also be nested "radially," i.e. in the radial direction of the stent, which allows for increased expansion ratio. In comparison to a purely radially nested stent, such embodiments can have a smaller non-deployed profile. In contrast to a purely axially nested stent, elements and/or components are allowed to overlap each other when non-deployed, which allows for a larger expansion ratio than would be possible with a purely axially nested stent. As such, embodiments can thereby combine the advantages of both design platforms to simultaneously achieve a smaller crossing profile and a large expansion ratio.

Various embodiments of an axially-radially nested, diametrically expandable vascular device or stent for maintaining support of a body lumen are disclosed herein. Such embodiments of the vascular device can be expandable medical implants that can be axially-radially nested, expandable, translating, and moveable for enlarging an occluded portion of a vessel. For example, the vascular device can be a slide-and-lock vascular device. One advantage of embodiments of the axially-radially nested stent is that it maintains the expanded size, without significant recoil.

In an embodiment, an axially-radially nested stent is provided that is expandable from an axially-radially nested unexpanded state to an expanded state. The stent can comprise a tubular member having longitudinal and circumferential axes. The tubular member can comprise a plurality of linkage assemblies. In some embodiments, each linkage assembly can comprise a linkage section and at least one connector.

The linkage section can have a central body and at least one interconnection member extending from the central body in a circumferential direction. The central body can include at least one engagement aperture being disposed through the central body in a circumferential direction. The engagement aperture can be sized and configured to receive a given interconnection member from an adjacent linkage assembly to provide one-way movement of the linkage assembly relative to the adjacent linkage assembly from the axially-radially nested unexpanded state to the expanded state.

The connector can have at least one connection point whereat an interlocking end of the interconnection member can be coupled to the connector. The connector can further have at least one engagement aperture being disposed through the connector in a circumferential direction. The engagement aperture can be sized and configured to receive another given interconnection member of another adjacent linkage to provide one-way movement of the linkage assembly relative to the other adjacent linkage assembly during expansion of the stent.

In another embodiment, an axially-radially nested stent is provided that can comprise a tubular member comprising a plurality of linkage sections. Each linkage section can comprise a central body and at least one interconnection member. The central body can include at least one engagement aperture being disposed through the central body in a circumferential direction. The interconnection member can extend from the central body in a circumferential direction. The engagement aperture can be sized and configured to receive a given interconnection member from an adjacent linkage section to provide one-way movement of the linkage section relative to the adjacent linkage section from the axially-radially nested unexpanded state to the expanded state. Further, the interconnection member can be axially offset from the given interconnection member of the adjacent linkage section.

In accordance with another embodiment, an offset rail stent is provided that is expandable from an axially-radially nested unexpanded state to an expanded state. Similar to the embodiment mentioned above, the stent can comprise a tubular member having longitudinal and circumferential axes. The tubular member can comprise a plurality of linkage assemblies. Each linkage assembly can comprise a linkage section, and first and second connectors.

The linkage section can comprise a central section, at least first and second ratcheting elements, and first and second bridge sections. The linkage section can be disposed along the circumferential axis of the tubular member, and can define a radial thickness. The central section can have first and second ends. The first and second ratcheting elements can be coupled to the respective ones of the first and second ends of the central section and can extend in a generally circumferential direction. The first and second ratcheting elements can have respective first and second distal interlocking ends. The first and second bridge sections can be disposed adjacent the respective ones of the first and second ends of the central section. The first and second bridge sections can have a reduced thickness relative to other portions of the linkage section for allowing first and second ratcheting elements of an adjacent linkage section to pass therealong for reducing the axial profile of the tubular member.

In addition, the first connector can comprise a first connection point whereto the first distal interlocking end of the first ratcheting element can be coupled. The first connector can further comprise at least one first engagement aperture wherethrough a ratcheting element of a third adjacent linkage assembly or module can be received and engaged by the first engagement aperture for facilitating one-way circumferential movement of the first connector and linkage assembly relative to the third adjacent linkage assembly or module with the third adjacent linkage assembly or module moving in a direction opposite to the direction of one-way movement of the first adjacent linkage assembly or module.

Further, the second connector can comprise a second connection point whereto the second distal interlocking end of the second ratcheting element can be coupled. The second connector can further comprise at least one second engagement aperture wherethrough a ratcheting element of a fourth adjacent linkage assembly or module can be received and engaged by the second engagement aperture for facilitating one-way circumferential movement of the second connector and linkage assembly relative to the fourth adjacent linkage assembly or module with the fourth adjacent linkage assembly or module moving in a direction opposite to the direction of one-way movement of the second adjacent linkage assembly or module.

In accordance with another embodiment, the offset rail stent can comprise a tubular member comprising a plurality of linkage strands and at least one connector. The plurality of linkage strands can extend in generally parallel directions along the longitudinal axis. Each linkage strand can have a plurality of central bodies being interconnected in an end-to-end fashion via flexible portions. Each central body can comprise at least one interconnection member having an interlocking end and extending therefrom in a circumferential direction. Each central body can include at least one bridge section being disposed on the central body. The bridge section can have a reduced thickness relative to other portion of the linkage strand for allowing passage of an interconnection member of an adjacent linkage strand therealong for reducing an axial profile of the stent.

Additionally, the connector can have at least one connection point whereat the interlocking end of the interconnection member can be coupled to the connector. The connector can further have at least one engagement aperture being disposed through the connector in a circumferential direction. The engagement aperture can be configured to receive another given interconnection member of another adjacent linkage to provide one-way movement of the linkage assembly relative to the other adjacent linkage assembly during expansion of the stent from an axially-radially nested unexpanded state to an expanded state.

In accordance with yet another embodiment, another offset rail stent is provided that can comprise a tubular member comprising a plurality of linkage strands and a plurality of coupling elements.

The linkage strands can extend in generally parallel directions along the longitudinal axis. Each linkage strand can have a plurality of frame elements being interconnected in an end-to-end fashion via at least one interconnection element. Each frame element can comprise at least one rail member extending from the frame element in a circumferential direction. Each frame element can further comprise at least one engagement aperture configured to receive an adjacent rail member of an adjacent linkage strand.

The coupling elements can each be attachable to a respective rail member after insertion of the rail member through the engagement aperture. Engagement of the coupling element and the engagement aperture can provide one-way movement of a given linkage strand relative to an adjacent linkage strand during expansion of the stent from an axially-radially nested unexpanded state to an expanded state.

In accordance with yet another embodiment, a telescoping slide-and-lock stent is provided. The stent can comprise a tubular member comprising at least one linkage component, at least one slide-and-lock element, and at least one interconnector block. The linkage component can be disposed along the longitudinal axis of the tubular member. Each linkage component can comprise at least one section. The section can include a pair of flexible portions. The section can further include generally elongate rail portions attached to the flexible portions. The rail portions can each have distal ends and proximal ends whereat the rail portions are attached to the flexible portions. The rail portions can be oriented generally parallel with respect to each other.

The slide-and-lock element can have a head portion and an elongate neck portion. The head portion can have a pair of apertures being sized and configured to receive the rail portions of the section of the linkage component to facilitate one-way movement of the linkage component relative to the slide-and-lock element. The neck portion can be longitudinally interposed between the rail portions.

The interconnector block can be disposed intermediate the flexible portions of the section of the linkage component. The interconnector block can comprise a pair of central connection points being configured to attachably receive the respective ones of the distal ends of the rail portions. The interconnector block can further comprise at least one engagement aperture wherethrough the neck portion of the slide-and-lock element can be received for facilitating one-way circumferential movement of the slide-and-lock element relative to the linkage component.

In accordance with yet another embodiment, a modular dual expansion stent is provided. The stent can comprise a tubular member comprising a plurality of strands of interconnected expandable modules. Each of the strands of interconnected modules can be disposed along the longitudinal axis of the tubular member. Each module can comprise first and second portions. The first and second portions can be interconnected via opposing flexible portions.

The first portion can have a belt component extending therefrom in the circumferential direction. The second portion can have a guide rail component and a buckle component. The guide rail component can extend in the circumferential direction adjacent and generally parallel to the belt component. The guide rail component can have at least one lateral protrusion. The buckle component can be configured for receiving therethrough a belt component and a guide rail component from another module of another circumferentially adjacent strand for interconnecting the strands about the circumferential axis of the tubular member. The buckle component can be operative to slide along the guide rail component and engage the at least one lateral protrusion for facilitating one-way circumferential movement of the buckle component of the module relative to the guide rail component of the other module for facilitating one-way circumferential expansion of the stent.

Further, the module can also include at least one stabilizer block that can be attachable to the guide rail component. The stabilizer block can be sized and configured to engage the belt component such that relative movement between the guide rail component and the belt component produces one-way circumferential expansion of the module to provide a second means of circumferential expansion of the stent.

In another embodiment, an improved stent is provided that desirably is small enough and flexible enough when collapsed to permit uncomplicated delivery to the affected area; one that expands uniformly to a desired diameter; one that maintains the expanded size, without significant recoil; one that can have sufficient scaffolding to provide a clear through-lumen; one that supports endothelialization or covering of the stent with vessel lining, which in turn minimizes the risk of thrombosis; and one that can have a greater capacity to deliver therapeutic agents to minimize injury, treat restenosis and other vascular diseases. Some embodiments provide a stent that can be sufficiently flexible upon deployment to conform to the shape of the affected body lumen and one that expands uniformly to a desired diameter, without undesired change in length. There can be no change length or the stent length can increase or decrease with efficacy, as required or desired.

In some embodiments, axially offset stent sections can be linked together in a wide variety of techniques for example by utilizing linkage sections, segments or frames. The linkage sections can include spring elements that advantageously provide enhanced stent flexibility.

At full expansion, the stent articulating and/or interlocking structural members can be captured through a wide variety of techniques, to limit and control the stent maximum expansion. These include, for example, but are not limited to, hard stops, capture straps, overhanging elements, covers, tongue-groove configurations and other suitable geometries, that can be employed or created through a wide variety of techniques to provide for stent expansion control.

Some embodiments can utilize a number of features to create slide and lock mechanisms that allow for controlled and predictable device expansion. For example, deflectable and non-deflectable elements and members can be employed to achieve desired deployment and lock out performance. The skilled artisan will appreciate that a variety of mechanisms, features and/or geometries can readily be included to achieve the desired deployment and lock out performance. For example, mechanisms can be employed that incorporate the bulk of the structural element, or smaller localized sub-elements can be employed.

In other embodiments, structural elements can be linked together and interlocking elements captured through a wide variety of techniques. For example, channels can be created or added that allow the elements to slide within, between or therethrough. Other examples include, but are not limited to, capture straps, overhanging elements, covers, tongue-groove configurations and other suitable geometries, that can be employed or created through a wide variety of techniques to provide for linkage and capture of elements.

Stents in accordance with some embodiments can be fabricated or created using a wide variety of manufacturing methods, techniques and procedures. These include, but are not limited to, laser processing, milling, stamping, forming, casting, molding, laminating, bonding, welding, adhesively fixing, and the like, among others.

In some embodiments, stent features and mechanisms can be created in a generally two dimensional geometry and further processed, for example by utilizing, but not limited to, bonding, lamination and the like, into three dimensional designs and features. In other embodiments, stent features and mechanisms can be directly created into three dimensional shapes, for example by utilizing, but not limited to, processes such as injection molding and the like.

The stent can be fabricated from at least one or more materials. In preferred variations to the above-described stents, the stent further can comprise a material selected from the group consisting of metals, polymers, and composites. Preferably, the polymer can comprise a bioresorbable polymer. More preferably, the polymer can comprise a radiopaque, bioresorbable polymer. In one aspect, the polymer forms a coating on at least a portion of the stent. The polymer coating can further comprise a biocompatible, bioresorbable polymer adapted to promote a selected biological response.

The vascular devices, prostheses or stents can be formed from a number of suitable materials. These include, without limitation, stainless steel alloys, spring-steel alloys, cobalt-chrome alloys, nickel-titanium alloys, titanium alloys, platinum-iridium alloys, tantalum and derivatives thereof, and combinations thereof, among others.

Advantageously, the substantially non-deforming components of certain embodiments allow the use of other suitable materials as well. These include, but are not limited to, ceramics, polymers, rubbers, bioresorbable and other materials which dissipate in time, combinations thereof, among others.

A method for re-treatment of a body lumen is disclosed in accordance with another embodiment. The method can comprise the steps of: deploying to a region of the body lumen any of the above described stents, wherein the stent can be made from a bioresorbable polymer, and resides at the region for a period of time; and administering to the region, after the period of time, a second treatment, such as for example, treatments selected from the group consisting of a second stent of any kind, angioplasty, arthrectomy, surgical bypass, radiation, ablation, local drug infusion, etc., or any subsequent intervention or treatment.

In preferred variations to the above-described stents, the stent further can comprise at least one therapeutic agent. The therapeutic agent can be selected from the group consisting of an antiproliferative agent, an anti-inflammatory agent, an anti-matrix metalloproteinase agent, a lipid lowering agent, a cholesterol modifying agent, an anti-thrombotic agent and an antiplatelet agent. The therapeutic agent can be an antiproliferative agent selected from the group consisting of Paclitaxel, Rapamycin, ABT-578, Biolimus A9, Everolimus, tacrolimus, and derivatives and analogs thereof.

In preferred variations to the above-described stents, the stent further can comprise a layered material. Preferably, the layered material can comprise a bioresorbable polymer. The stent can also comprise a plurality of scales extending from an exterior surface of at least one component of the stent to at least engage a sidewall of a body lumen.

One key design aspect of embodiments of an expandable vascular device is its deployment ratio, that is, the ratio of final maximum diameter to initial compacted diameter. Depending upon the particular design being pursued or the application being addressed, the deployment ratio can vary. Advantageously, certain stent embodiments can allow the number of elements to be increased or decreased, that is, varied, as needed or desired, to achieve optimization of the deployment ratio as well as device performance, crossing profile, flexibility, among others. This desirably adds to the device versatility and utility. Advantageously, dimensions (e.g., length, width, and the like) can also be modified to change expansion characteristics and features.

In preferred variations to the above-described stents, the stent further can comprise a retractable sheath sized for enclosing the tubular member during delivery to a treatment site.

In preferred variations to the above-described stents, the stent further can comprise a solid wall region. The solid wall region can further comprise an opening.

In preferred variations to the above-described stents, the stent further can comprise a polymeric sheath.

A system for treating a site within a vessel is also disclosed. The system can comprise a catheter having a deployment means, and any of the above-described stents, wherein the catheter is adapted to deliver the stent to the site and the deployment means is adapted to deploy the stent. In preferred variations, the catheter can be selected from the group consisting of over-the-wire catheters, coaxial rapid-exchange catheters, and multi-exchange delivery catheters.

A process of making a therapeutic agent-eluting device is also disclosed. The process comprises the steps of: applying at least one therapeutic agent mixture onto at least one frame of the device; and forming the device using the at least one frame. The device can be a stent. The step of separating the at least one frame from a polymer film can be performed after the step of applying at least one therapeutic agent onto a polymer film. Further, the method can further comprise the step of creating a pattern on the polymer film to define the at least one frame such that the at least one frame is detachable from the film.

In some embodiments, the creating a pattern step can be performed before the applying at least one therapeutic agent step is performed. The creating a pattern step can comprise using a laser to lase the pattern onto the polymer film.

The applying step can comprise mounting the polymer film in a spraying apparatus. The applying step can also comprise spraying at least one time the therapeutic agent mixture onto the polymer film. The applying step can also comprise applying a plurality of therapeutic agent mixtures onto the at least a portion of the polymer film. The applying step can also comprise applying at least one therapeutic agent mixture onto one side of the polymer film. The applying step can also comprise applying at least one therapeutic agent mixture onto both sides of the polymer film. The applying step can also comprise dipping the polymer film into at least one therapeutic agent mixture. The applying step can also comprise impregnating the polymer film with at least one therapeutic agent mixture.

The process can further comprise the step of cleaning the at least one frame with a cleaning solution. The process can also further comprise the step of drying the polymer film after applying the at least one therapeutic agent mixture thereto.

In accordance with another embodiment, another process of making a therapeutic agent-eluting device is also provided. The process can comprise: applying at least one therapeutic agent onto at least one frame of the device; and forming the device using the at least one frame. The device can be a stent. The process can also comprise the step of creating a pattern on a polymer film to define the at least one frame such that the at least one frame is detachable from the film.

The creating a pattern step can be performed before the applying at least one therapeutic agent step is performed. The creating a pattern step can comprise using a laser to lase the pattern onto the polymer film.

The applying step can comprise mounting the at least one frame in a spraying apparatus. The applying step can also comprise spraying at least one time the therapeutic agent mixture onto the at least one frame. The applying step can also comprise applying a plurality of therapeutic agent mixtures onto the at least a portion of the at least one frame. The applying step can also comprise applying at least one therapeutic agent mixture onto one side of the at least one frame. The applying step can also comprise applying at least one therapeutic agent mixture onto both sides of the at least one frame. The applying step can also comprise dipping the at least one frame into at least one therapeutic agent mixture. The applying step can also comprise impregnating the at least one frame with at least one therapeutic agent mixture.

The process can also comprise the step of cleaning the at least one frame with a cleaning solution. The process can also comprise the step of drying the at least one frame after applying the at least one therapeutic agent mixture thereto. The process can also comprise the step of separating the at least one frame from a polymer film.

Certain aspects, advantages and novel features of the various embodiments have been described herein above. Of course, it is to be understood that not necessarily all such advantages can be achieved in accordance with any particular embodiment. Thus, many embodiments can be carried out in a manner that achieves or optimizes one advantage or group of advantages as taught or suggested herein without necessarily achieving other advantages as can be taught or suggested herein.

All of these embodiments are intended to be within the scope of the present disclosure. These and other embodiments will become readily apparent to those skilled in the art from the following detailed description of the preferred embodiments having reference to the attached Figures.

BRIEF DESCRIPTION OF THE DRAWINGS

The abovementioned and other features of the embodiments disclosed herein are described below with reference to the drawings of the preferred embodiments. The illustrated embodiments are intended to illustrate, but not to limit the same. The drawings contain the following Figures:

FIG. 4 is a perspective view of an axially-radially nested stent in accordance with another embodiment.

FIG. 5A is a top view of the stent of FIG. 4 illustrating a plurality of interconnected linkage assemblies.

FIG. 5B is a side view of the stent of FIG. 4.

FIG. 6 is a perspective view of a first linkage section of the stent of FIG. 4 in accordance with an embodiment.

FIG. 7 is a perspective view of a second linkage section of the stent of FIG. 4 in accordance with an embodiment.

FIG. 10A is a top view of a linkage section of a linkage assembly, in accordance with an embodiment.

FIG. 10B is an end view of the linkage section of FIG. 10A.

FIG. 11 is an enlarged top view of an interlocking end of the linkage section, in accordance with an embodiment.

FIG. 22 is a top view of a linkage component of the stent of FIGS. 21A-B.

FIG. 23A is a top view of a slide-and-lock element of the stent of FIGS. 21A-B.

FIG. 23B is a cross-sectional view of the slide-and-lock element of FIG. 21A taken along the lines 23B-23B of FIG. 21A.

FIG. 24 is a cross-sectional view of an interconnector block of the stent of FIG. 21A taken along the lines 24-24 of FIG. 21A.

FIG. 26 is a top view of a module of the stent of FIG. 25 in the nested or unexpanded state.

FIG. 27 is a cross-sectional view of a stabilizer block of the module of FIG. 26 taken along the lines 27-27 of FIG. 26, in accordance with an embodiment.

FIG. 29A is a perspective view of another embodiment of a stent placed on a balloon catheter.

DETAILED DESCRIPTION

Figure 1:
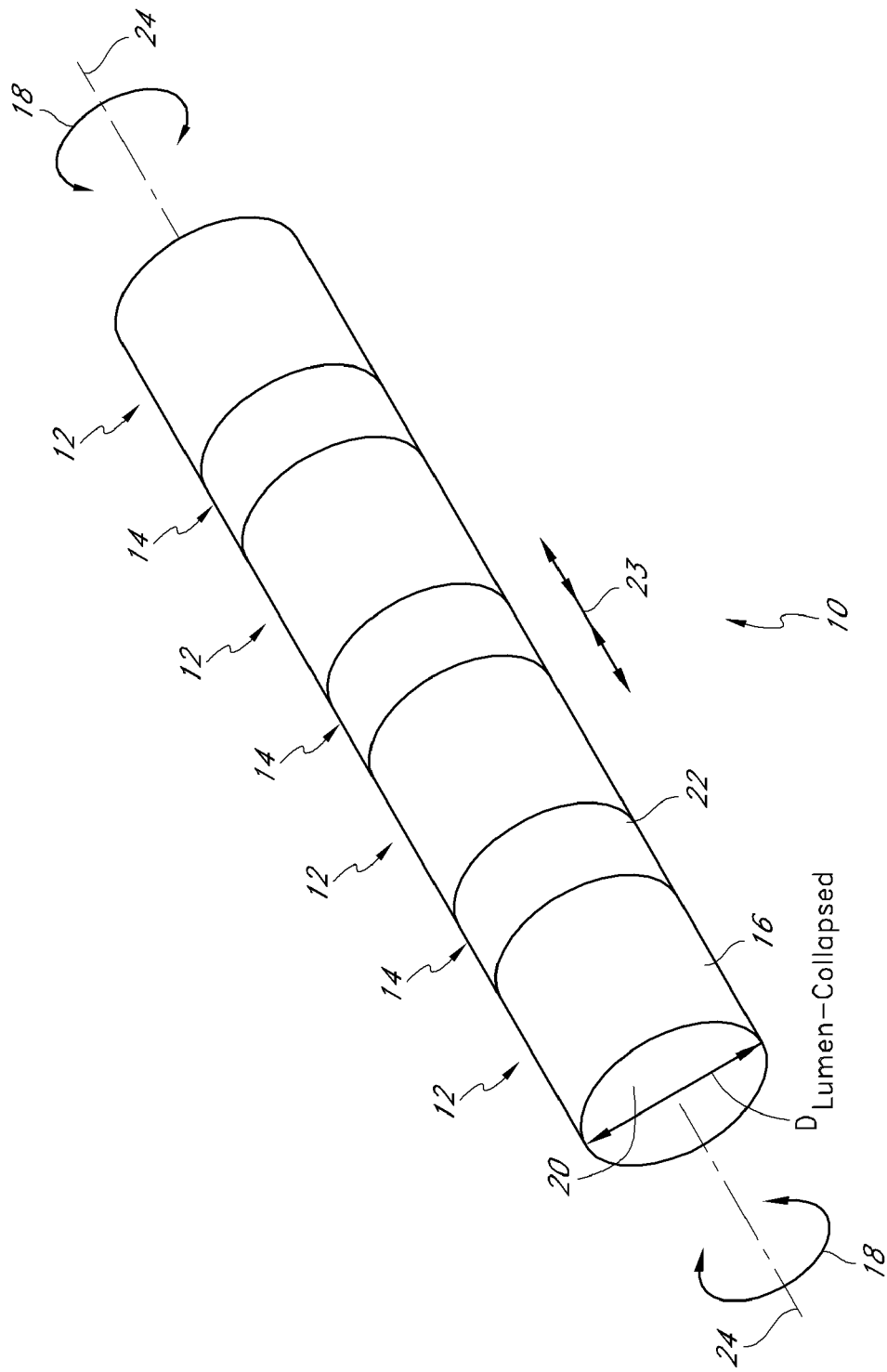
FIG. 1 is a simplified schematic perspective view of an expandable rotary axially-radially nested stent in an undeployed state in accordance with an embodiment.

The preferred embodiments described herein relate generally to expandable medical implants for maintaining support of a body lumen and, in particular, to an axially-radially nested, diametrically expandable, rotary vascular device for enlarging an occluded portion of a vessel.

While the description sets forth various embodiments in specific detail, it will be appreciated that the description is illustrative only and should not be construed in any way as limiting the same. Furthermore, various applications of the embodiments, and modifications thereto, which can occur to those who are skilled in the art, are also encompassed by the general concepts described herein.

The term "stent" is used herein to designate embodiments for placement in (1) vascular body lumens (i.e., arteries and/or veins) such as coronary vessels, neurovascular vessels and peripheral vessels for instance renal, iliac, femoral, popliteal, subclavian and carotid; and in (2) nonvascular body lumens such as those treated currently i.e., digestive lumens (e.g., gastrointestinal, duodenum and esophagus, biliary ducts), respiratory lumens (e.g., tracheal and bronchial), and urinary lumens (e.g., urethra); (3) additionally such embodiments can be useful in lumens of other body systems such as the reproductive, endocrine, hematopoietic and/or the integumentary, musculoskeletal/orthopedic and nervous systems (including auditory and ophthalmic applications); and, (4) finally, stent embodiments can be useful for expanding an obstructed lumen and for inducing an obstruction (e.g., as in the case of aneurysms).

In the following description of embodiments, the term "stent" can be used interchangeably with the term "prosthesis" and should be interpreted broadly to include a wide variety of devices configured for supporting a segment of a body passageway. Furthermore, it should be understood that the term "body passageway" encompasses any lumen or duct within a body, such as those described herein.

Still further, it should be understood that the term "shape-memory material" is a broad term that can include a variety of known shape memory alloys, such as nickel-titanium alloys, as well as any other materials that return to a previously defined shape after undergoing substantial plastic deformation.

The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon can be regulated for expanding the stent to a particular desired diameter. Accordingly, balloon expandable stents can be used in applications wherein precise placement and sizing are important. Balloon expandable stents can be used for direct stenting applications, where there is no pre-dilation of the vessel before stent deployment, or in prosthetic applications, following a pre-dilation procedure (e.g., balloon angioplasty). During direct stenting, the expansion of the inflatable balloon dilates the vessel while also expanding the stent.

The stent can be fabricated from at least one or more materials. In another preferred embodiment, the stent further can comprise a tubular member formed from a biocompatible and preferably, bioresorbable polymer, such as those disclosed in co-pending U.S. application Ser. No. 10/952,202, the disclosure of which is incorporated herein in its entirety by reference. It is also understood that the various polymer formulae employed can include homopolymers and heteropolymers, which can include stereoisomerism, composites, filled materials, etc. Homopolymer is used herein to designate a polymer comprised of all the same type of monomers. Heteropolymer is used herein to designate a polymer comprised of two or more different types of monomer which is also called a co-polymer. A heteropolymer or co-polymer can be of a kind known as block, random and alternating. Further with respect to the presentation of the various polymer formulae, products according to embodiments can be comprised of a homopolymer, heteropolymer and/or a blend of such polymers.

The term "bioresorbable" is used herein to designate polymers that undergo biodegradation (through the action of water and/or enzymes to be chemically degraded) and at least some of the degradation products can be eliminated and/or absorbed by the body. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The term "inherently radiopaque" is used herein to designate polymer that is intrinsically radiopaque due to the covalent bonding of halogen species to the polymer. Accordingly, the term does encompass a polymer which is simply blended with a halogenated species or other radiopacifying agents such as metals and their complexes.

In another preferred variation, the stent further can comprise an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that can be natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, can include virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" can include 1) "biomolecule", as used herein, encompassing a biologically active peptide, protein, carbohydrate, vitamin, lipid, or nucleic acid produced by and purified from naturally occurring or recombinant organisms, tissues or cell lines or synthetic analogs of such molecules, including antibodies, growth factors, interleukins and interferons; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent can also include vitamin or mineral substances or other natural elements.

In some embodiments, the design features of the circumferentially nested elements can be varied to customize the functional features of strength, compliance, radius of curvature at deployment and expansion ratio. In some embodiments, the stent can comprise a resorbable material and vanishes when its job is done. In some embodiments, the stent serves as a therapeutic delivery platform.

Some aspects are also disclosed in co-pending U.S. patent application Ser. Nos. 11/016,269, 60/601,526, 10/655,338, 10/773,756, and 10/897,235, the disclosures of each of which are incorporated herein in their entirety by reference thereto.

Some features and arrangements of embodiments of stents are disclosed in U.S. Pat. Nos. 6,033,436, 6,224,626, and 6,623,521, each issued to Steinke, the disclosures of each of which are hereby incorporated in their entirety by reference thereto.

Some embodiments relate to an expandable stent having a plurality of longitudinally arranged sections, segments or frames. The sections can have a plurality of circumferentially nesting sliding and locking elements permitting one-way sliding, including locking and/or deforming and locking, of the elements from a collapsed diameter to an expanded/deployed diameter, but inhibiting recoil from the expanded diameter. In some embodiments, these circumferentially nested sliding and locking elements pivot and/or slide. In some embodiments, the stent can comprise a polymer and can be fabricated by a combination of laminating and laser cutting a plurality of layers.

Advantageously, the stent design elements and interlocks can be varied to customize the functional features of strength, compliance, radius of curvature at deployment and expansion ratio. In some embodiments, the stent can comprise a resorbable material and vanishes when its job is done. In some embodiments, the stent serves as a delivery platform for therapeutic agents such as pharmaceutical compounds or biological materials.

Some embodiments relate to a radially expandable stent used to open, or to expand a targeted area in a body lumen. Some embodiments relate to a radially expandable stent used as a drug delivery platform to treat vascular conditions. In some embodiments, the assembled stent can comprise a tubular member having a length in the longitudinal axis and a diameter in the radial axis, of appropriate size to be inserted into the body lumen. The length and diameter of the tubular member can vary considerably for deployment in different selected target lumens depending on the number and configuration of the structural components, described below.

The tubular member in accordance with some embodiments can have a "clear through-lumen," which can be defined as having no structural elements protruding into the lumen in either the collapsed or expanded diameters. Further, the tubular member can have smooth marginal edges to minimize the trauma of edge effects. The tubular member can be preferably thin-walled and flexible (e.g., less than about 0.01 Newtons force/millimeter deflection) to facilitate delivery to small vessels and through tortuous vasculature.

In preferred embodiments, the wall thickness can be about 0.0001 inches to about 0.0250 inches, and more preferably about 0.0010 to about 0.0100 inches. However, the wall thickness depends, at least in part, on the selected material. For example, the thickness can be less than about 0.0080 inches for plastic and degradable materials and can be less than about 0.0020 inches for metal materials. More particularly, for a 3.00 mm stent application, when a plastic material is used, the thickness can be preferably in the range of about 0.0020 inches to about 0.0100 inches. The thin walled design can also minimize blood turbulence and thus risk of thrombosis. The thin profile of the deployed tubular member in accordance with some embodiments also facilitates more rapid endothelialization of the stent. The above thickness ranges have been found to provide preferred characteristics through all aspects of the device including assembly and deployment. However, it will be appreciated that the above thickness ranges should not be limiting with respect to the scope of the embodiments and that the present teachings can be applied to devices having dimensions not discussed herein.

In some embodiments, the wall of the tubular member can comprise at least one section, which can comprise at least one sliding and locking structural element. Preferably, a plurality of sections can be connected in the longitudinal axis via linkage elements which couple at least some of the structural elements between adjacent sections. The structural elements can be configured within each section so as to generally define the circumference of the tubular member. In some embodiments, each structural element within a section can be a discrete, unitary structure. In some embodiments, the tubular member can comprise an integral unit including one or more sections with one or more structural elements. In one embodiment, each structural element can comprise one or more circumferential ribs bowed in the radial axis to form a fraction of the total circumference of the tubular member.

At least some of the structural elements can have two or more structural members and at least one articulating mechanism for providing relative motion between associated structural members. In one embodiment, the articulating mechanism can include a translation inducing mechanism that generates controlled stent expansion. The articulating between structural members can be such that a locking or ratcheting mechanism is formed, whereby the associated structural members and elements can slide circumferentially in one direction but can be substantially prevented from sliding circumferentially in an opposite direction. The tubular member can be adjustable from at least a first collapsed diameter to at least a second expanded diameter, but advantageously recoil to a smaller diameter can be minimized by the locking mechanism. The amount of recoil can be customized for the application by adjusting the configuration of the articulating locking mechanism. For example, one or more stops, teeth, slots or grooves and engaging elements, tabs, teeth or tongues can be incorporated into the structural components of the tubular member whereby recoil (i.e., collapse from an expanded diameter to a more collapsed diameter) can be minimized to less than about 5%.

In many of the embodiments illustrated and described herein, the intraluminal stent can be preferably provided with "slide-and-lock elements" generally referred to herein as "circumferential elements" or "circumferentially nested elements." The circumferential elements can be slidably interconnected with circumferentially adjacent elements in a manner wherein the stent exhibits mono-directional circumferential expansion from a collapsed state to an expanded state, e.g., during deployment. The circumferential elements can be preferably configured to provide a ratcheting effect such that the stent can be maintained (i.e., "locked-out") in the expanded diameter after deployment within the body passage. More particularly, the structures (e.g., circumferential elements) can flex or bend; however, in certain embodiments, unlike conventional balloon expandable stents, no substantial plastic deformation of the elements are required during expansion of the stent from a collapsed diameter to an expanded diameter. Elements of this type can be generally referred to herein as "non-deforming elements." Accordingly, the term "non-deforming element" is intended to generally describe a structure that substantially maintains its original dimensions (i.e., length and width) during deployment of the stent. Each circumferential element can be preferably formed as a flat sheet that can be cut or otherwise shaped to provide a moveable and/or slide-and-lock mechanism. In some embodiments, the stent can comprise "deforming elements" which preferably undergo plastic deformation during stent expansion The phrase "weaves through paired slots" can have the meaning described in U.S. Pat. Nos. 5,549,662 and 5,733,328. As used herein, this phrase describes a particular slidable coupling or articulation between stent components, wherein a portion of one stent component passes through one of a pair of slots in another stent component, and then passes back through the second of the pair of slots, creating a weave-like interlocking configuration. Preferred embodiments employ slidable couplings or articulations between stent components that avoid weave-like configurations, such that in these preferred embodiments, no portion of a stent component weaves through paired slots in another stent component.

In some embodiments, the stent preferably can comprise at least one longitudinal module, which can consist of a series of axial elements, including one or more slide-and-lock axial elements and optionally one or more passive axial elements, linked in the longitudinal axis by flexible coupling portions. Preferably, the axial elements from two or more similar longitudinal modules can be slidably connected to circumferentially adjacent axial elements. Additionally, single module (or jellyroll-type) embodiments can also be encompassed within the scope of this disclosure. For example, each module can be a discrete, unitary structure that, in some embodiments, does not stretch or otherwise exhibit any substantial permanent deformation during stent deployment.

Advantageously, some embodiments of the stent substantially can at least partially reduce or minimize overlap between the structural elements and thus can desirably reduce the effective wall thickness of the stent.

In some embodiments, at least some of the structural elements can have at least one articulating mechanism (e.g., deflecting or non-deflecting) for providing slidable engagement between adjacent circumferentially offset structural elements and/or adjacent axially offset structural elements. In one embodiment, the articulating mechanism can include a tongue and groove configuration.

Embodiments and Design Features of the Inventions

Figure 2:
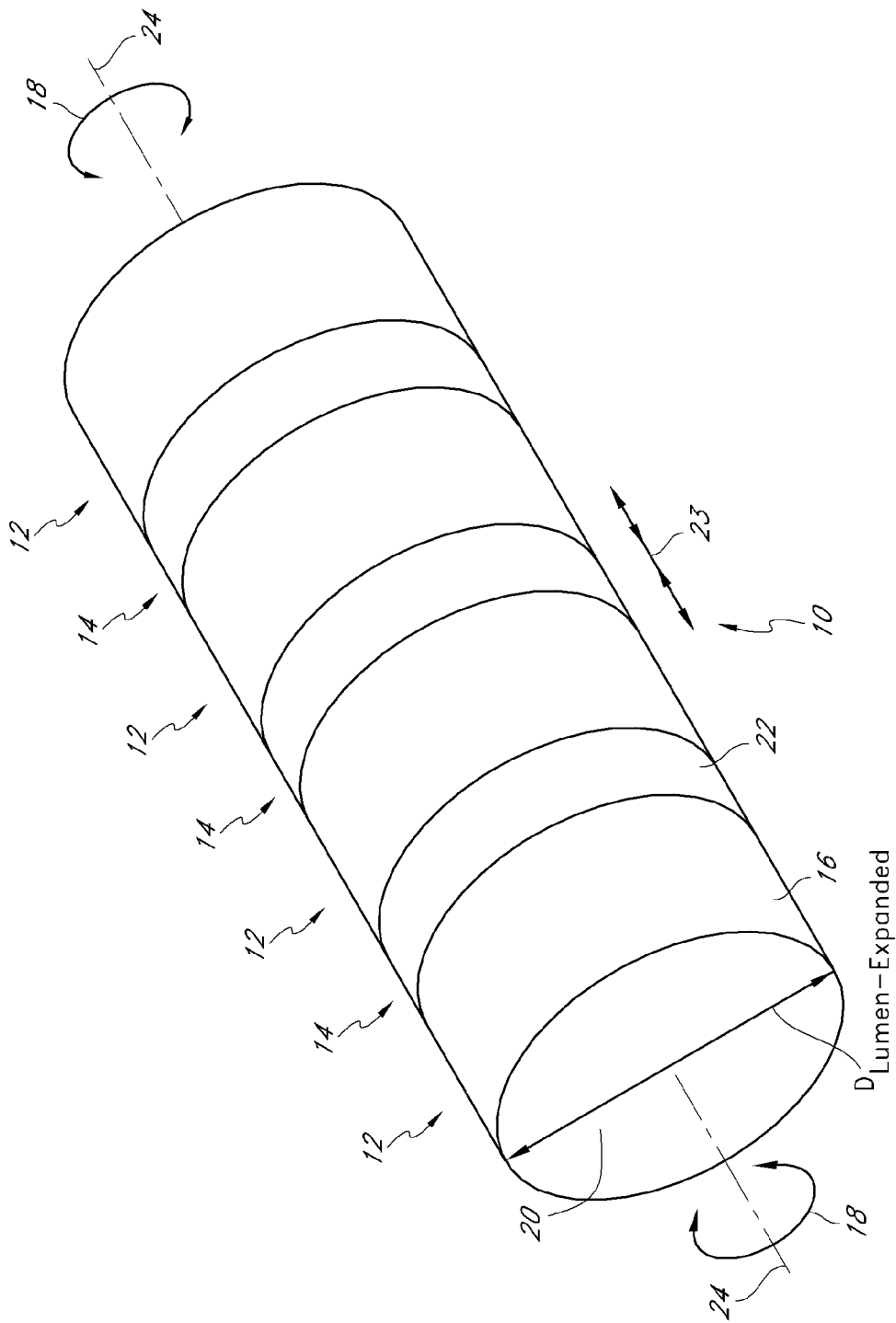
FIG. 2 is a simplified schematic perspective view of the expandable rotary axially-radially nested stent in a deployed state.
Figure 3:
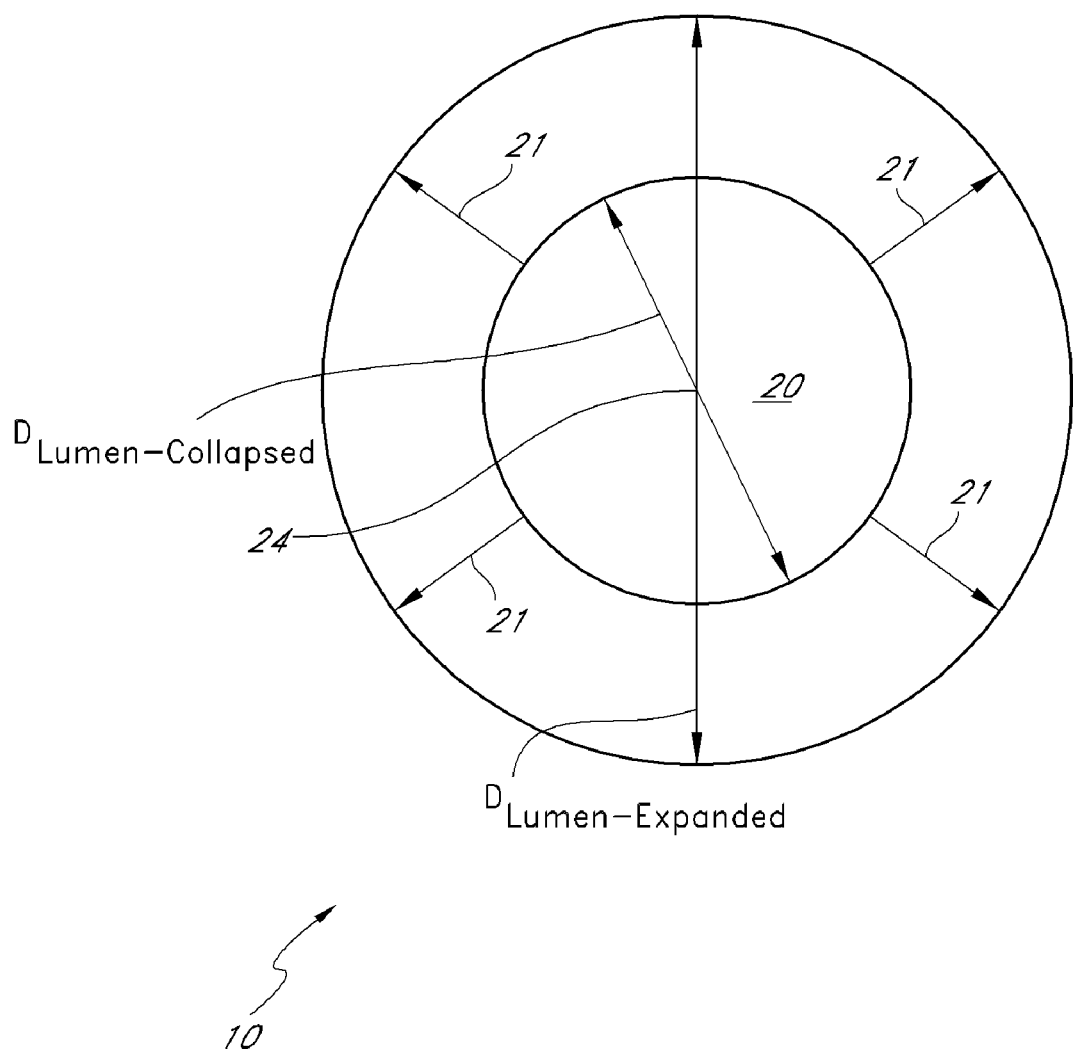
FIG. 3 is a simplified schematic end view of the expandable rotary axially-radially nested stent depicting diametric expansion.

FIGS. 1-3 show conceptual views of embodiments of an expandable vascular device, prosthesis or stent 10 in deployed and undeployed states. The stent 10 can be operative to move via translation and/or slide and lock movement. These drawings are intended to be conceptual in nature and certain embodiments of the stent and its structural elements, structural members, slide and lock mechanisms and other features are discussed in further detail below with reference to further drawings as described in further detail herein.

Referring in particular to FIGS. 1-3, the stent 10 can have a tubular form with a wall comprising a plurality of generally longitudinally arranged linked circumferential sections, segments or frames 12 and 14. The stent 10 can have a through lumen 20 which, along with the stent itself, can be expandable from a first diameter ($D_{lumen\text{-}collapsed}$ or $D_{inner\text{-}collapsed}$) to a second diameter ($D_{lumen\text{-}expanded}$ or $D_{inner\text{-}expanded}$). The stent 10 and/or the lumen 20 can have a generally longitudinal axis 24.

The stent 10 can comprise alternatingly arranged sections 12 and flexible sections 14. The section 12 can be operative to move via translation and/or slide and lock movement. Each section 12 can include one or more expandable structural elements 16 that can have articulating and/or ratcheting mechanisms (as discussed in more detail below) to facilitate controlled stent expansion while minimizing recoil. The number of structural elements in a section 12 and/or the number of sections 12 in the stent 10 can be efficaciously varied and selected, as needed or desired.

Each flexible section 14 can include a plurality of linkage elements 22 and can connect adjacent stent sections 12. One or more of the linkage elements 22 can comprise resilient components, such as spring elements. The linkage elements 22 provide flexibility and allow expansion of the flexible sections 14 along with stent expansion. The linkage elements 22 also allow for rotary and/or axial deflection of members of the structural elements 16 during stent expansion to a deployed state. In some embodiments, the linkage elements 22 can facilitate this deflection by providing a resilient biasing mechanism to achieve substantially elastic deflection or deformation. The number of linkage elements 22 in a flexible section 14 and/or the number of flexible sections 14 in a stent 10 can be efficaciously varied and selected, as needed or desired.

During stent expansion, there can be circumferential motion (as generally indicated by arrows 18) and diametric expansion (as generally indicated by arrows 21) from a collapsed diameter ($D_{lumen\text{-}collapsed}$ or $D_{inner\text{-}collapsed}$) to an expanded diameter ($D_{lumen\text{-}expanded}$ or $D_{inner\text{-}expanded}$). In certain embodiments there can also be axial or longitudinal motion of some of the stent elements and/or members that can be generally parallel to the stent axis 24 (as generally indicated by arrows 23).

In one embodiment, $D_{lumen\text{-}collapsed}$ or $D_{inner\text{-}collapsed}$ can be in the range from about 0.812 mm (0.032 inches) to about 0.914 mm (0.036 inches), including all values and sub-ranges therebetween. In one embodiment, $D_{lumen\text{-}expanded}$ or $D_{inner\text{-}expanded}$ can be in the range from about 2.0 mm (0.07874 inches) to about 8.0 mm (0.315 inches), including all values and sub-ranges therebetween. In modified embodiments, $D_{lumen\text{-}collapsed}$ and/or $D_{lumen\text{-}expanded}$ can have other suitable values with efficacy, as needed or desired.

At full expansion, a capture mechanism can be provided to limit further stent expansion. Each section 12 can comprise one or more capture mechanisms such as, but not limited to, hard stops, straps, overhanging elements, covers, tongue-groove configurations and other suitable geometries or devices that prevent further stent expansion. This desirably serves to control and limit the stent diameter to a predetermined deployment diameter.

Axially-Radially Nested Stent Inventions

FIGS. 4-7 illustrate an embodiment of an axially-radially nested stent 50. The stent 50 can include a plurality of interconnecting linkage sections 52 that can form a tubular member. The linkage sections 52 can be operative to move relative to each other in order to cause expansion of the tubular member from a nested or unexpanded state to an expanded or deployed state. It is also contemplated that the linkage sections 52 can include an interlocking means in order to at least prevent the stent from collapsing. Thus, in some embodiments, the linkage sections 52 can interlock to maintain the stent 50 in the deployed state after expansion.

FIG. 4 is a perspective view of an embodiment of the stent 50 illustrating that the linkage sections 52 can be formed to interlock and/or overlap adjacent linkage sections 52. Referring to FIGS. 5A-B, the stent 50 can be configured such that linkage sections 52 extend circumferentially about the tubular member. The linkage sections 52 can include a central body 54 and at least one interconnection member 56. The linkage sections 52 can be configured such that the interconnection members 56 of a given linkage section 52 are axially offset from interconnection members 56 of an adjacent linkage section 52.

For example, as illustrated in FIG. 5A, linkage section 52' includes interconnection members 56' that are axially offset from linkage members 56" of interconnection member 52". Although the embodiment illustrated in FIG. 5A illustrates that the interconnection members 56' are axially interposed between the interconnection members 56", it is contemplated that other configurations can also be provided. For example, the interconnection members 56', 56" can be positioned in an alternating fashion such that a single interconnection member 56', 56" is interposed between a pair of respective interconnection members 56', 56".

Additionally, FIG. 5B illustrates the interconnection and overlapping of interconnection members 56 of adjacent linkage sections 52. As illustrated in the front view of FIG. 5A, the side view of FIG. 5B shows the interconnection members 56', 56" and linkage sections 52', 52". As shown therein, the interconnection members 56' can extend from the linkage section 52' and engage linkage section 52" in a radially nested configuration. The interconnection members 56' then extend circumferentially beyond the linkage section 52" and overlap a portion of linkage section 52"'. Similarly, interconnection members 56" extend from the linkage section 52" to engage linkage section 52"' and overlap linkage section 52. The illustrated embodiment can therefore expand through circumferential retraction of the interconnection members 56 through the central bodies 54 of the linkage sections 52.

Referring now to FIGS. 6 and 7, embodiments of the linkage section are illustrated. FIG. 6 is an illustration of linkage section 52'. The linkage section 52' includes the central body 54' and the interconnection members 56'. In addition, linkage section 52' can also be formed to include engagement apertures 58'. The engagement apertures 58' can extend through the central body 54' in a circumferential direction. The engagement apertures 58' are preferably sized and configured to receive interconnection members 56 of an adjacent linkage section 52. In some embodiments, the engagement apertures 58' can be configured to provide one-way relative movement of the interconnection members 56 therein. As described in regard to other embodiments of the stents disclosed herein, various locking and/or ratcheting mechanisms can be implemented for allowing the one-way movement of the interconnection member 56 relative to the body 54' of the linkage 52'.

FIG. 7 is an illustration of the linkage section 52" in accordance with another embodiment. The linkage section 52" can include interconnection members 56" and the central body 54". Additionally, the linkage section 52" can include engagement apertures 58". The engagement apertures 58", similar to engagement apertures 58', can be configured to receive interconnection members 56'. The engagement apertures 58" can be configured to allow one-way movement of the interconnection members 56' relative to a central body 54", as similarly discussed above.

It is contemplated that the linkage sections 52 can be integrally formed of a single piece of material. However, it is also contemplated that the central body 54 can be formed separately from the interconnection members 56. As also discussed above, the arrangement and configuration of the interconnection members 56 relative to each other and to the engagement apertures 58 can be variously modified to achieve a variety of configurations, as desired.

For example, as illustrated in FIGS. 6 and 7, the interconnection members 56, 56', 56" can be axially spaced adjacent to each other or separated by engagement apertures 58". In addition, it is contemplated that a plurality of engagement apertures can axially separate a pair of interconnection members 56. Thus, physical properties of the stent, such as strength, crush resistance, flexibility, and the like can be selectively modified based on the configuration of one or more of the linkage sections 52 of the stent 50. The assembled stent 50 can also be configured to include side apertures or other features based on the overlapping and/or interlocking of the interconnection members with adjacent linkage sections.

In addition, it is also contemplated that the interconnection members 56 of the linkage sections 52 of the stent 50 can include interlocking ends and/or deflectable members to facilitate interconnection of the interconnection member 56 with the engagement apertures 58 of the linkage section 52. Further, the interconnection members 56 can also include a plurality of teeth or other engagement means disposed therealong. For example, as shown and described below with reference to FIGS. 10A and 11, the interconnection members 56 can include teeth disposed along a side thereof that can be configured to engage the engagement aperture 58 in a manner sufficient to couple the interconnection member 56 to an adjacent linkage section. Preferably, the interconnection between the interconnection member 56 and the adjacent linkage section provides for a non-releasable engagement between the components. Further, the connection should preferably be a durable connection that is able to withstand tension and compression which the stent 50 will likely undergo.

Offset Rail Stent Inventions

FIGS. 8-16 illustrate inventions and various features and configurations of portions of offset rail stents that can be expanded from an axially-radially nested unexpanded state to an expanded state. Although the illustrated embodiments show only portions of a stent, it is contemplated that a plurality of these portions can be interconnected with each other to form a tubular member having longitudinal and circumferential axes. Accordingly, the tubular member can comprise a plurality of these portions, herein called linkage assemblies or strands, embodiments of which are shown in FIGS. 8-10B and FIGS. 14-16, respectively. Although specific embodiments of the linkage assemblies or strands are disclosed, various modifications can be performed by one of skill provided with the disclosure and teachings herein. Further, it should be noted that the elements and features disclosed with regard to FIGS. 11-13C can be implemented with these and other embodiments disclosed herein.

Figure 8:
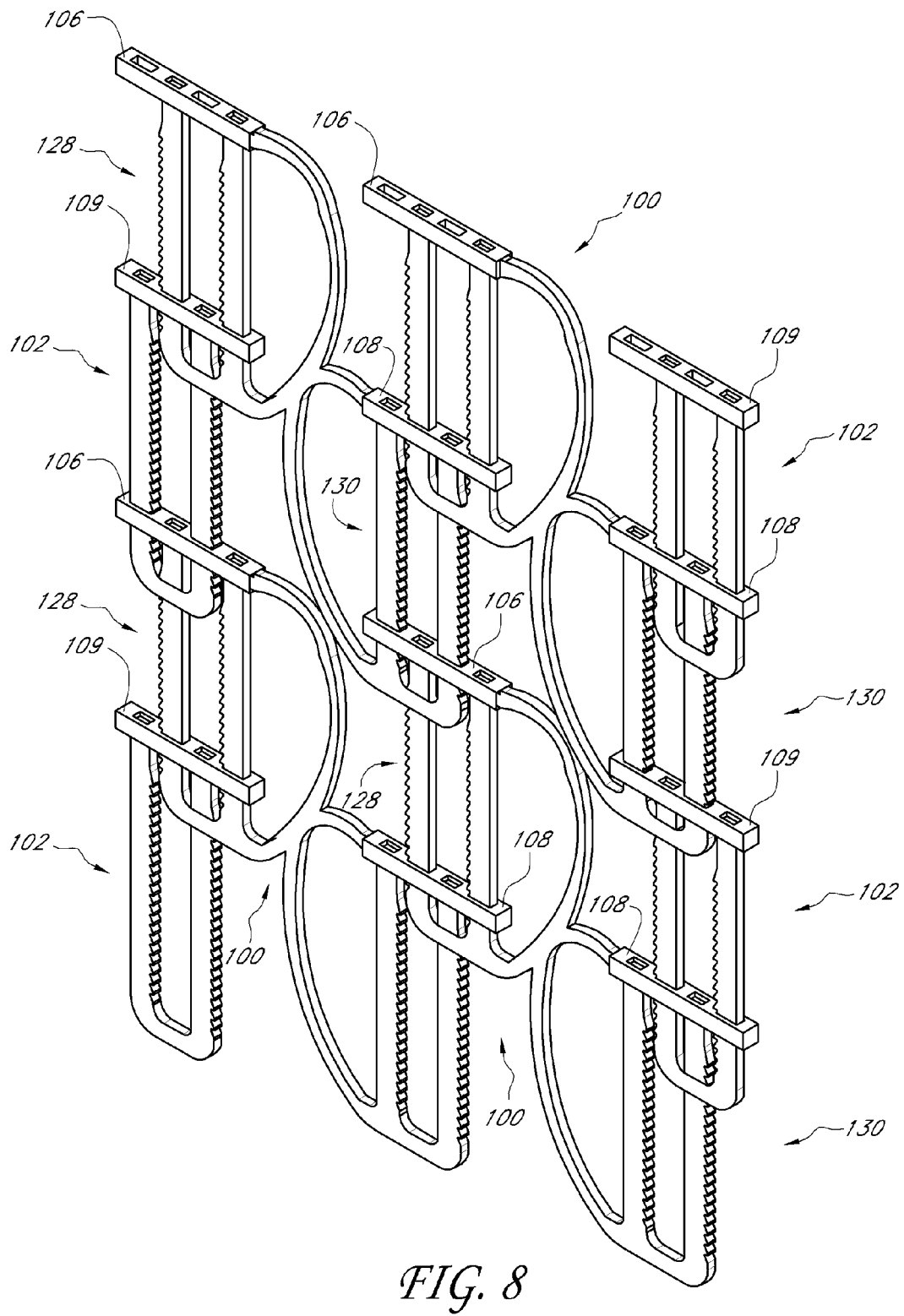
FIG. 8 is a perspective view of a portion of an axially-radially nested stent in accordance with yet another embodiment.

FIG. 8 is a perspective view of a plurality of linkage assemblies 100 that are interconnected to form a portion of the tubular member. As shown, FIG. 8 represents the linkage assemblies 100 being in the expanded state. These linkage assemblies 100 can be interconnected with additional linkage assemblies to form a tubular member thereby forming a stent. As described below, the linkage assemblies 100 can each be configured to interconnect with an adjacent linkage assembly 100 and to provide one way, ratchet-type motion in order to facilitate expansion of the stent.

Figure 9:
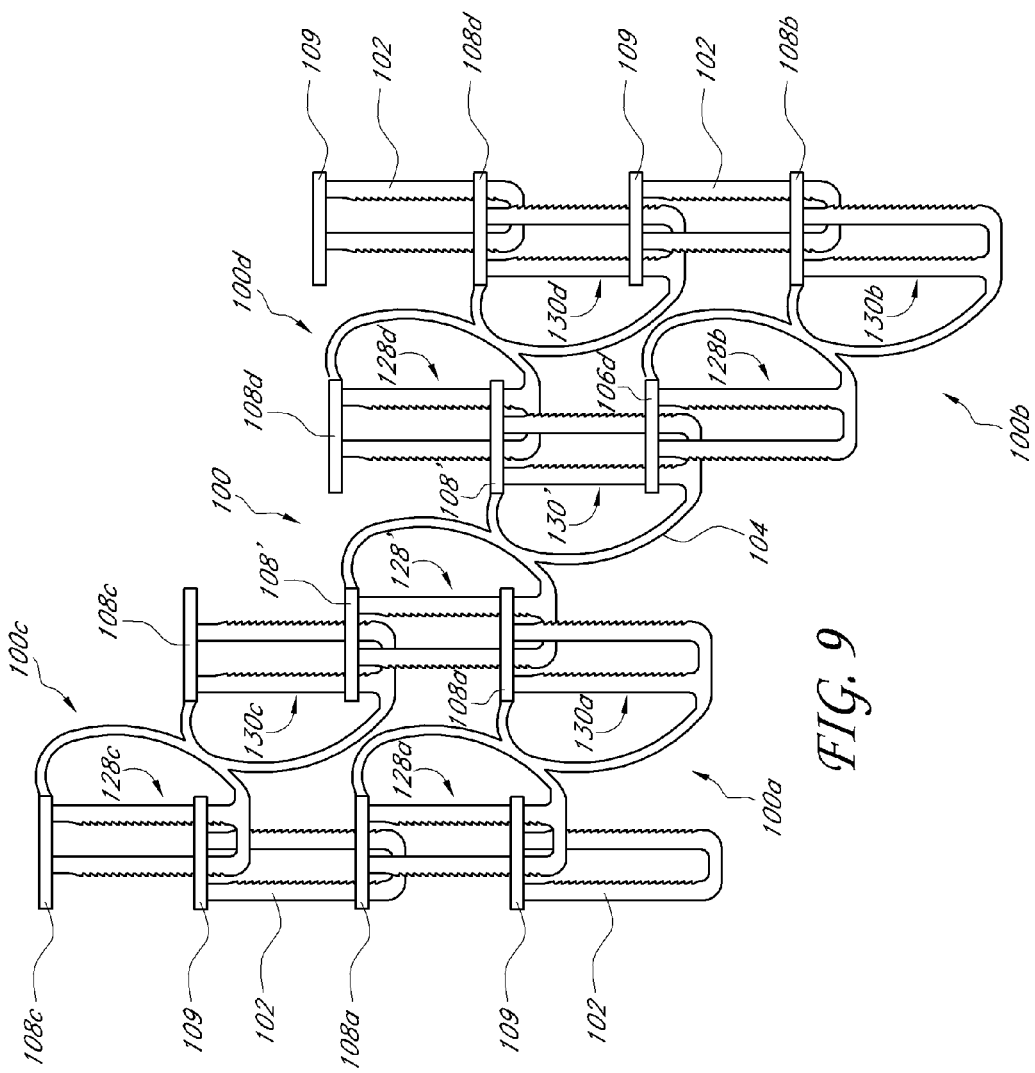
FIG. 9 is a top view of the stent of FIG. 8 illustrating a plurality of interconnected linkage assemblies.

FIG. 9 is a top view of a central linkage assembly 100' and four linkage assemblies 100a, 100b, 100c, and 100d that are interconnected with the central linkage assembly 100'. FIG. 9 is intended to illustrate a representative linkage assembly 100' and to illustrate the various interconnections that the linkage assembly 100' can create with adjacent linkage assemblies. However, as shown in FIG. 8, the linkage assembly 100 can also interconnect with at least one module 102 (which module 102 can be used at the ends of the stent to interconnect adjacent linkage assemblies), which will be described in greater detail below. As shown in FIGS. 8-9, each linkage assembly 100 can include a linkage section 104, a first connector 106, and a second connector 108, and each module 102 can include a third connector 109. In some embodiments, the first, second, and third connectors 106, 108, 109 can be configured to be interchangeable and/or the have the same configuration as each other.

With reference now to FIG. 10A, an exemplary embodiment of the linkage assembly 100 will now be described. FIG. 10A is a top plan view of the linkage section 104. The linkage section 104 can include a central section 110 having first and second ends 112, 114. In addition, the linkage section 104 also includes at least first and second ratcheting elements 120, 122. The first and second ratcheting elements 120, 122 can be coupled to the respective ones of the first and second ends 112, 114 of the central section 110. As illustrated, in some embodiments, the first and second ratcheting elements 120, 122 can be oriented generally parallel relative to each other. In addition, when the stent is in an assembled state, the first and second ratcheting elements 120, 122 can generally extend in the circumferential direction, which is generally transverse relative to the longitudinal axis of the tubular member.

According to an aspect of some embodiments, the central section 110 is preferably configured as a non-rigid structure that interconnects the first and second ratcheting elements 120, 122. In this regard, the non-rigid interconnection can facilitate and accommodate bending of the tubular member as it is placed into the body lumen. The central section 110 can also be configured to include first and second connection ends 124, 126. In some embodiments, the first and second connection ends 124, 126 can extend in a direction generally opposite the first and second ends 112, 114. In this regard, the first end 112 can be generally separated from the first connection end 124, and similarly, the second end 114 can be generally separated from the second connection end 126. As described further below, each of the respective ends can be utilized to provide circumferential support for the ratcheting elements of the linkage section 104, according to some embodiments.

As also illustrated in FIG. 10A, the linkage section 104 can be configured to include first and second pairs of ratcheting elements 128, 130. The first and second pairs of ratcheting elements 128, 130 can be coupled to the respective ones of the first and second ends 112, 114 of the central section 110. As with the first and second ratcheting elements 120, 122, the other ratcheting element of the respective first and second pairs 128, 130 can likewise extend in a generally circumferential direction and generally parallel relative to the respective first and second ratcheting element 120, 122.

In some embodiments, each of the ratcheting elements in the first and second pairs 128, 130 can be configured to include a distal interlocking end. For example, as shown in FIG. 10A, the first ratcheting element includes a first interlocking end 132 and the other ratcheting element 120a of the first pair 128 likewise includes an interlocking end 132a. Similarly, the second ratcheting element 122 includes a second interlocking end 134, and the other ratcheting end 122a of the second pair 130 includes a second interlocking end 134a.

The first and second interlocking ends 132, 134 can be configured to interconnect with the respective ones of the first and second connectors 106, 108. It is contemplated that the connection can be achieved by means of mechanical means, adhesive means, and the like. Referring to FIG. 11, an exemplary embodiment of an interlocking end 132' of a first ratcheting element 120' is illustrated. As shown therein, the interlocking end 132' can include a pair of deflectable members 136 that can be configured to engage the first connector 106 in a manner sufficient to couple the ratcheting element 120' to the first connector 106. Preferably, the interconnection between the interlocking end 132' and the first connector 106 provides for a non-releasable engagement between the components. Further, the connection should preferably be a durable connection that is able to withstand tension and compression which the stent will likely undergo.

As is shown in FIGS. 10A and 11, the ratcheting elements 120, 120a, 122, and 122a can include a plurality of teeth 138 along at least one side thereof. The teeth 138 can be configured to engage at least a portion of the respective connector 106, 108, in order to facilitate one-way movement of the ratcheting element relative to the connector. In other embodiments, the ratcheting elements can include a variety of locking mechanisms including indents, friction, etc.

Referring to FIGS. 10A-10B, the ratcheting elements 120, 122 and 120a, 122a can be of a different thickness than that of the remainder of the linkage section 104. Such a configuration can allow the ratcheting elements 120, 122 and 120a, 122a to overlay or underlay at least a portion of an adjacent linkage section when in the assembled state.

For example, the linkage section 104 shown in FIGS. 10A-10B can be configured such that bridge sections 139a, 139b have a reduced thickness compared to the remainder of the linkage section 104. Thus, when assembled, the ratcheting elements 120, 122 and 120a, 122a overlaying the bridge sections of an adjacent linkage section would tend to create a lesser cross-sectional or axial thickness.

The thicknesses of the bridge sections 139a, 139b and the ratcheting elements 120, 122 and 120a, 122a can be selectively configured to allow relative movement of these components during expansion of the stent. Indeed, various embodiments can be configured wherein one or both of these components can be thinner than the remainder of the linkage section. It is contemplated that such features can be modified as desired to enhance the axial cross-sectional profile or flow profile of the stent.

Figure 12A:
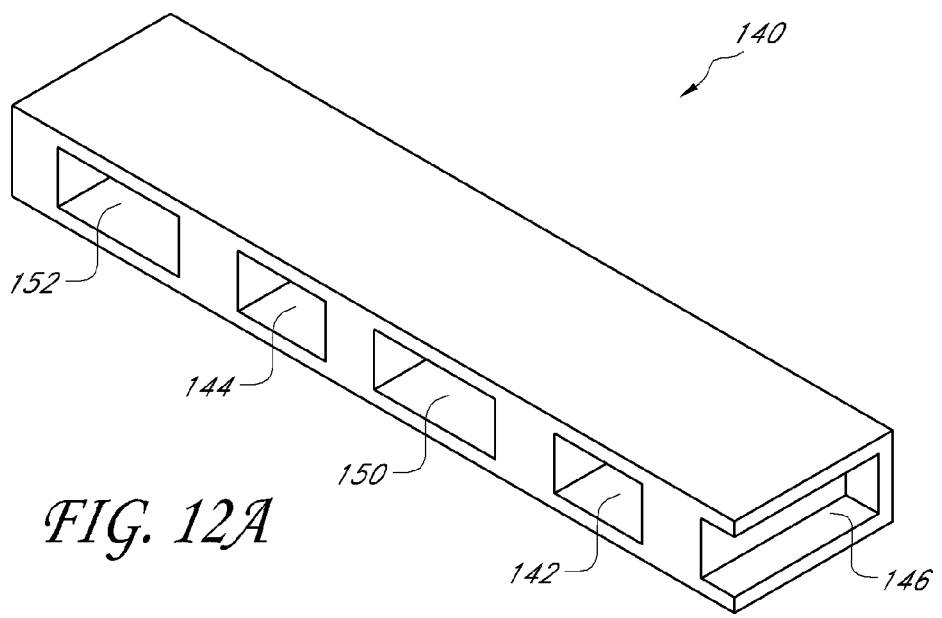
FIG. 12A is a perspective view of a connector of the linkage assembly of FIG. 8, in accordance with an embodiment.

FIG. 12A is an illustration of an exemplary connector 140 that can be used as one or both of the first and second connectors 106, 108 in the linkage assemblies 100. Further, as will be discussed further below, the connector 140 can also be used with the linkage strands 300 shown in FIGS. 14-16. The connector 140 preferably comprises at least a first connection point 142, where at the first distal interlocking end 132 of the first ratcheting element 120 can be coupled. In addition, as shown in FIG. 12A, the connector 140 can also include a second connection point 144 and a side connection point 146 in order to facilitate to interconnection of the interlocking end 132a and the first connection end 124, referring to the exemplary linkage section 104 of FIG. 10A. The connection points 142, 144, and 146 are preferably configured as apertures in some embodiments in order to allow the respective ends 132, 132a, and 124 to be received there unto. As mentioned above, it is contemplated that the connection intermediate the connector 140 and the linkage section 104 can be accomplished via mechanical, adhesive, or other means.

Figure 12B:
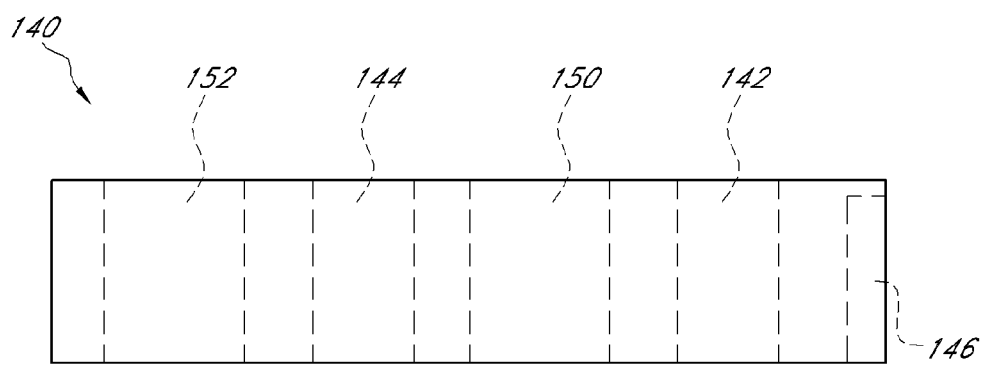
FIG. 12B is a top view of the connector of FIG. 12A.
Figure 12C:
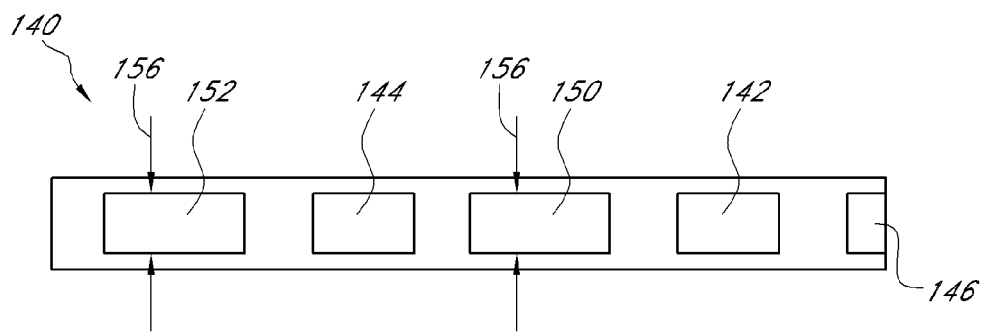
FIG. 12C is a front view of the connector of FIG. 12A.

As also shown in the embodiment illustrated in FIG. 12A, the connector 140 preferably comprises at least one first engagement aperture 150, and in some embodiments, includes a pair of engagement apertures 150, 152. As discussed in greater detail below, the engagement apertures 150, 152 are preferably sized and configured to allow passage therethrough of ratcheting elements of an adjacent linkage section. In this regard, in many embodiments, and as similarly mentioned above, the ratcheting elements should have a thickness that is less than a thickness 156 of the engagement apertures 150, 152 and the respective linkage sections in order to facilitate interconnection of the ratcheting elements therewith. FIGS. 12B and 12C illustrate respective top and front views of the connector 140 to indicate the configuration of an embodiment of the connector 140. As generally indicated in FIGS. 8 and 9, the connector 140 is preferably configured to allow a ratcheting element to be engaged within its engagement aperture to allow one-way movement of the ratcheting element relative to the connector 140. In this regard, one-way circumferential expansion of the stent can be achieved.

Figure 13A:
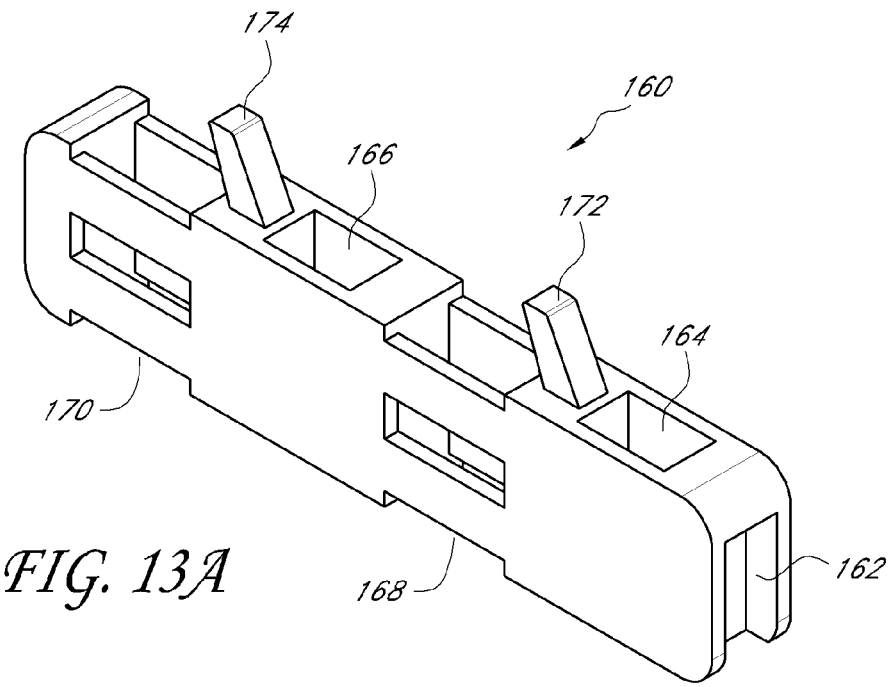
FIG. 13A is a perspective view of another connector, in accordance with another embodiment.
Figure 13B:
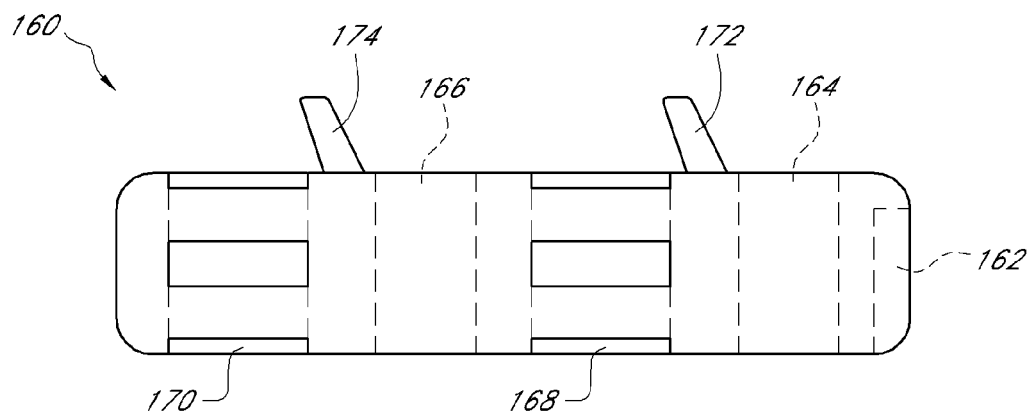
FIG. 13B is a top view of the connector of FIG. 13A.
Figure 13C:
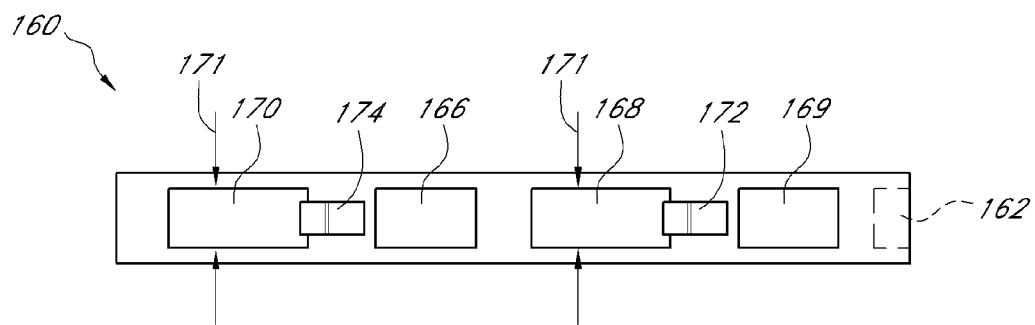
FIG. 13C is a front view of the connector of FIG. 13A.

FIGS. 13A-13C illustrate another embodiment of a connector 160. As similarly shown in FIGS. 12A-12C, the connector 160 of FIGS. 13A-13C can include a side connection point 162, a pair of first connection points 164, 166, and a pair of first engagement apertures 168, 170 having a thickness 171. However, the connector 160 can also be configured to include a locking means that resists movement of the ratcheting element relative to the engagement aperture. For example, the locking means can be configured as a pair of locking tabs 172, 174, as shown in FIGS. 13A-13C.

In accordance with an embodiment, the locking means can be configured as the locking tabs 172, 174, as shown in FIGS. 13A-13C. The locking tabs 172, 174 can be configured to extend from the connector 160 adjacent the respective ones of the pair of first engagement apertures 168, 170. In this manner, it is contemplated that when a ratcheting element is disposed through one of the pair of first engagement apertures 168, 170, one of the locking tabs 172, 174 can engage one of the plurality of teeth 138 disposed along the side of the ratcheting element. The locking means can include one or multiple locking tabs as desired to facilitate engagement of the connector with the ratcheting element.

In some embodiments, the locking means can be configured to include frictional engagement between surfaces. For example, an interior surface of the engagement apertures, can have a surface texture or finish configured to provide a frictional engagement between the ratcheting element and the engagement aperture. Further, the engagement apertures 168, 170 can be configured to include at least one protrusion or bump that can engage with the ratcheting element, similarly to the teeth mentioned above. Further, these various features can be used interchangeably on one or both of the ratcheting element and the respective engagement aperture. Accordingly, various features can be incorporated into the locking means in order to prevent recoil of the stent.

Referring again to FIGS. 8-9, various linkage assemblies are illustrated in an interconnected state. As best shown in FIG. 8, the linkage assemblies 100 are interconnected in a generally repetitive manner. It would be appreciated that, as discussed above, the first connectors 106 illustrated in FIG. 8 served to not only interconnect the first pair 128 of ratchet elements, but also interconnects with the second pair 130 of ratchet elements of an adjacent linkage assembly 100. In this regard, the interconnection of linkage assemblies 100 can result in a very stable and robust interconnection and framework of the stent.

In accordance with the embodiment shown in FIGS. 8-10B, a desired plurality of linkage assemblies 100 can be interconnected to create a stent of a desired axial length. Further, if desired, a plurality of linkage assemblies 100 can also be interconnected in the circumferential direction in order to provide a stent having a desired diameter in collapsed and/or expanded states. This is illustrated for example, in FIG. 9, where a grouping of linkage assemblies 100, 100a, 100b, 100c, and 100d are interconnected with linkage assemblies 100a, 100c and linkage assemblies 100b, 100d being interconnected via linkage assembly 100. Additional linkage assemblies can be added and interconnected to form the tubular member of the stent. In this regard, it is contemplated that the individual linkage assemblies 100 can be selectively configured as required in order to produce a stent having desirable size characteristics.

Figure 14:
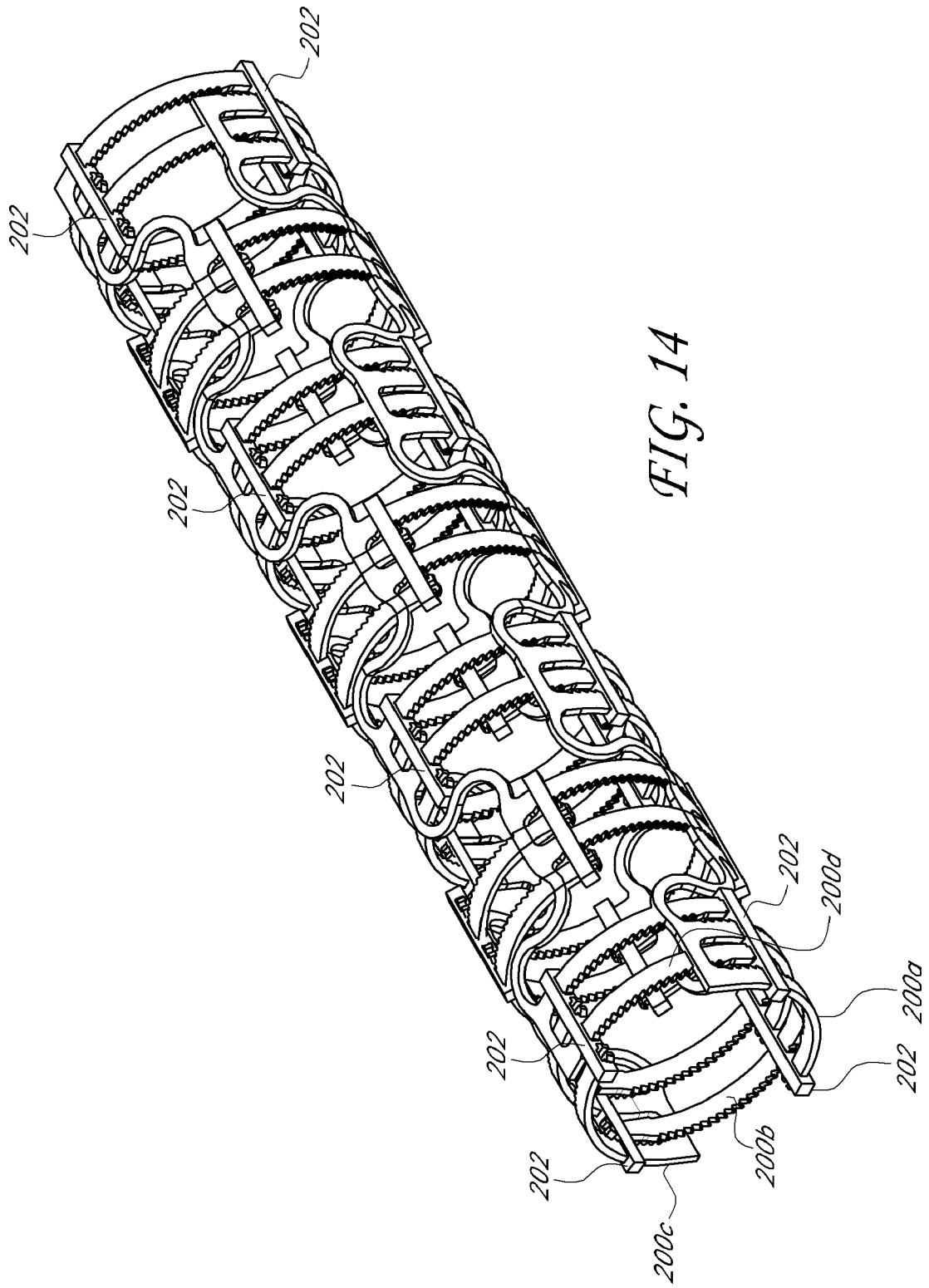
FIG. 14 is a perspective view of an axially-radially nested stent in accordance with yet another embodiment.
Figure 15:
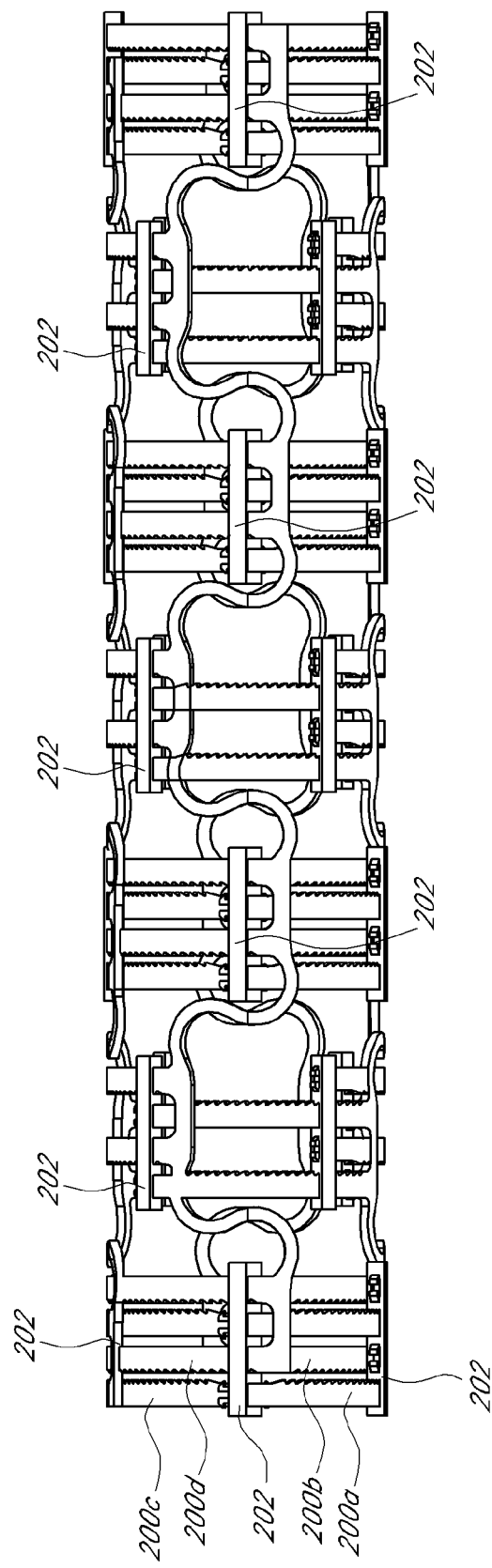
FIG. 15 is a top view of the stent of FIG. 14.
Figure 16:
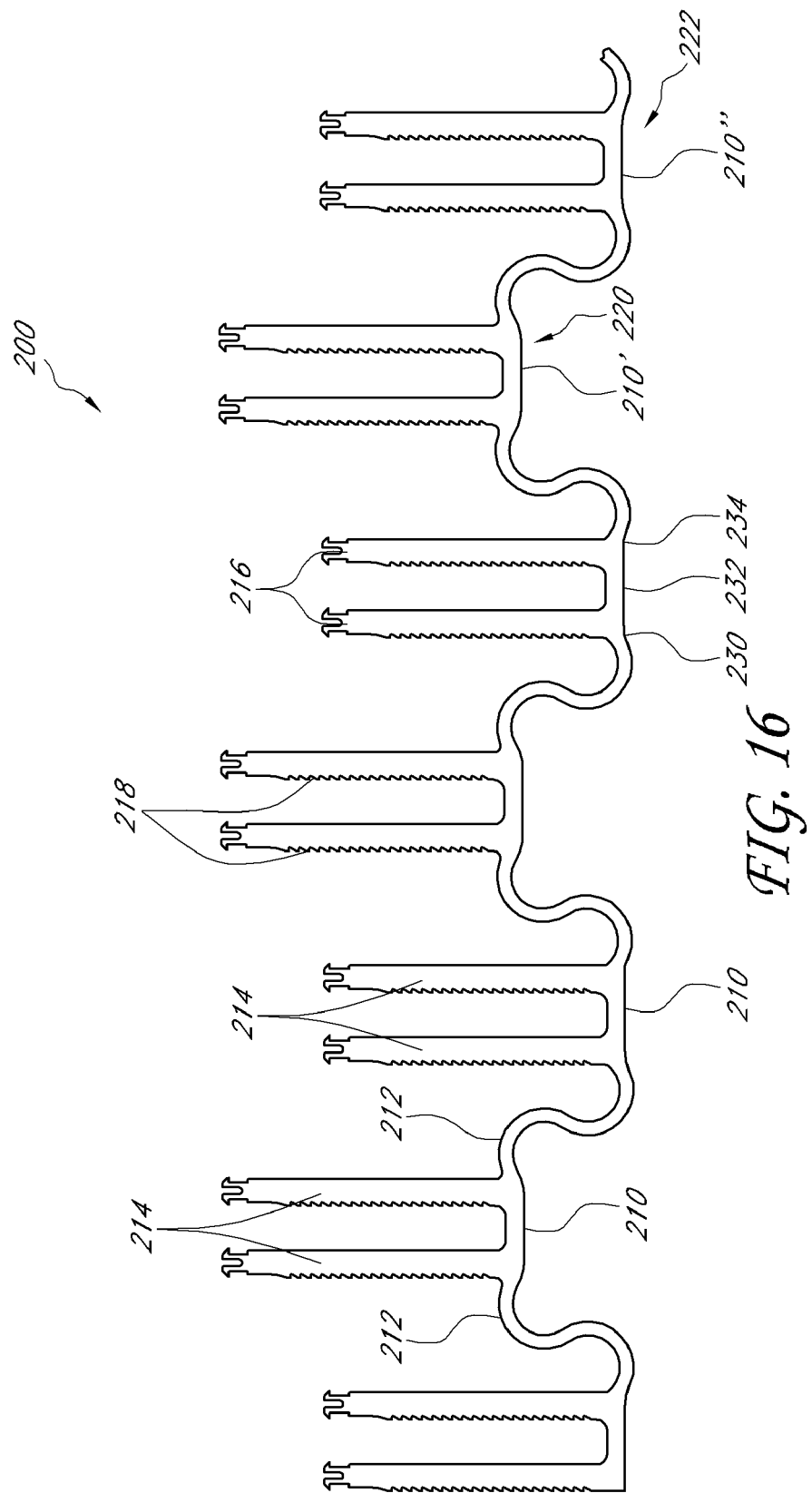
FIG. 16 is a top view of a linkage strand of the stent of FIG. 14.

Referring now to FIGS. 14-16, another embodiment of an axially-radially nested stent is shown. The tubular member of the stent in this embodiment can comprise a plurality of the linkage strands 200 and a plurality of connectors 202. As mentioned above, the linkage strands 200 and connectors 202 can be configured to have the elements and features disclosed above with regard to FIGS. 8-13C.

In contrast to the embodiments discussed above in relation to FIGS. 8-10B, the embodiments discussed now with respect to FIGS. 14-16, and others discussed herein, can be formed to a desired length and need only be interconnected in the circumferential direction (as opposed to interconnecting a plurality of linkage assemblies of the embodiments of FIGS. 8-13C). In other words, the embodiments of the linkage strands of the stent shown in FIGS. 14-16 can be formed to a desired axial or longitudinal length. As discussed herein, such forming operations can include injection molding and the like. Thus, individual linkage strands 200 can be injection molded at a desired length and then circumferentially interconnected to form the stent.

FIG. 14 is a perspective view and FIG. 15 is a top view of the stent in a generally expanded state. As shown, the stent includes four linkage strands 200a, 200b, 200c, and 200d. The linkage strands 200a, 200b, 200c, and 200d extend in generally parallel directions along the longitudinal axis and are interconnected such that in the unexpanded state and the expanded state, the linkage strands 200a, 200b, 200c, and 200d are axially-radially nested and do not include portions that protrude radially beyond the thicknesses of the linkage strands 200a, 200b, 200c, and 200d and the various connectors 202 used therewith. As such, a distinct advantage can be realized, as discussed above, in that the flow of fluids and the delivery of the stent can be facilitated.

Referring to FIG. 16, a linkage strand 200 is shown in a non-arcuate configuration. The linkage strand 200 can have a plurality of central bodies 210 being interconnected in an end-to-end fashion via flexible portions 212. Each central body 210 can comprise at least one interconnection member 214 having an interlocking end 216 and extending from the central body 210 in a circumferential direction. It is also contemplated that each central body 210 can be configured to have two interconnection members 214 extending therefrom. As discussed above with respect to other embodiments, the interconnection members 214 can be configured to include a connecting means 218, which can be a plurality of teeth disposed along a side of the interconnection member 214.

As will also be appreciated from FIG. 16, the linkage strand 200 can be configured such that adjacent central bodies 210 can be circumferentially offset relative to each other. Thus, in some embodiments, adjacent central bodies 210' and 210'' of the linkage strand 200 can be disposed in one of top and bottom positions 220, 222, as shown, respectively.

In addition, it is contemplated that at least one portion of the central body 210 disposed adjacent the interconnection members 214 can be configured to be of a different thickness than that of the remainder of the central body 210 and/or linkage strand 200. Such a configuration can allow the interconnection members 214 to overlay or underlay at least a portion of the central body an adjacent linkage strand when the stent is in the assembled state.

For example, the linkage strand 200 can be configured similarly to the embodiment shown in FIGS. 10A-10B. In this regard, at least one bridge section 230, 232, 234 of the linkage strand 200 can have a reduced thickness compared to the remainder of the linkage strand 200. Thus, when assembled, the interconnection members 214 overlaying the bridge sections of an adjacent linkage strand would tend to create a lesser cross-sectional or axial thickness.

The thicknesses of the bridge sections 230, 232, 234 and the interconnection members 214 can be selectively configured to allow relative movement of these components during expansion of the stent. Indeed, various embodiments can be configured wherein one or both of these components can be thinner than the remainder of the linkage section. It is contemplated that such features can be modified as desired to enhance the axial cross-sectional profile or flow profile of the stent.

Additionally, it is noted that the connectors 202 used with the linkage strands 200 can be configured similarly to the connectors 140 and 160 discussed above with regard to FIGS. 12A-13C. However, in embodiments using the linkage strands 200, it is contemplated that the side connection points 146, 162 of the respective ones of the connectors 140, 160 can be omitted. Nevertheless, the features and elements discussed above with respect to the connectors 140, 160 can similarly be used for the connectors 202 in order to facilitate interconnection, one-way relative movement, and structural support of the linkage strands 200 and connectors 202 of embodiments of the stent.

Referring now to FIGS. 17-20, other embodiments and features of some embodiments of an offset rail stent 250 are illustrated. The stent 250 comprises a tubular member having longitudinal and circumferential axes. As will be described below, the embodiments illustrated in FIGS. 17-20 utilize a unique structure that facilitates assembly of the stent 250. The stent 250 can be configured as an axially-radially nested stent that can be expandable from an axially-radially nested unexpanded state to an expanded state.

Figure 17:
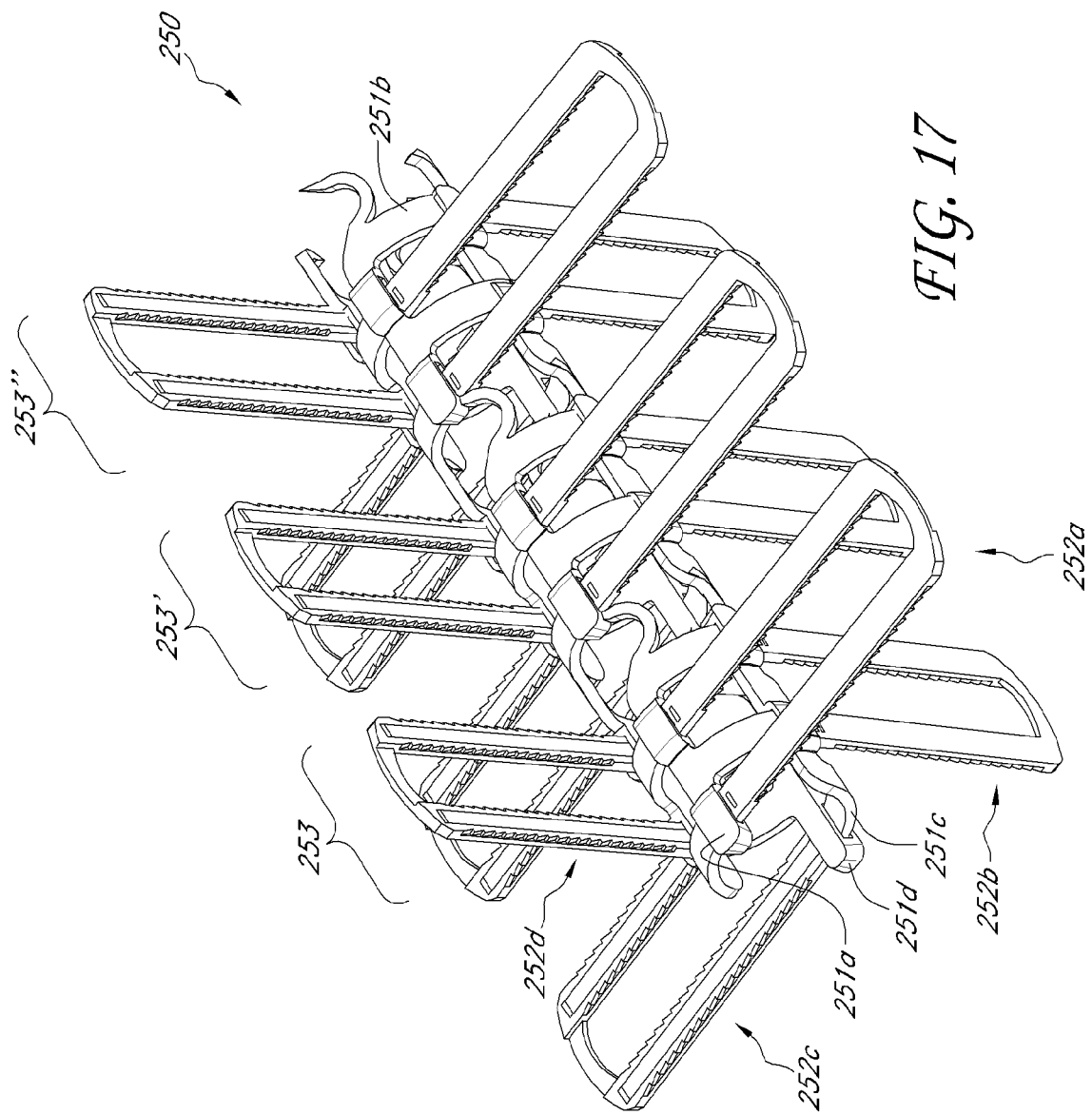
FIG. 17 is a perspective view of an axially-radially nested stent formed from a plurality of strands each comprising frame elements interwoven to form a closed loop wherein the stent is in an unexpanded, pre-deployment state, according to an embodiment.
Figure 18:
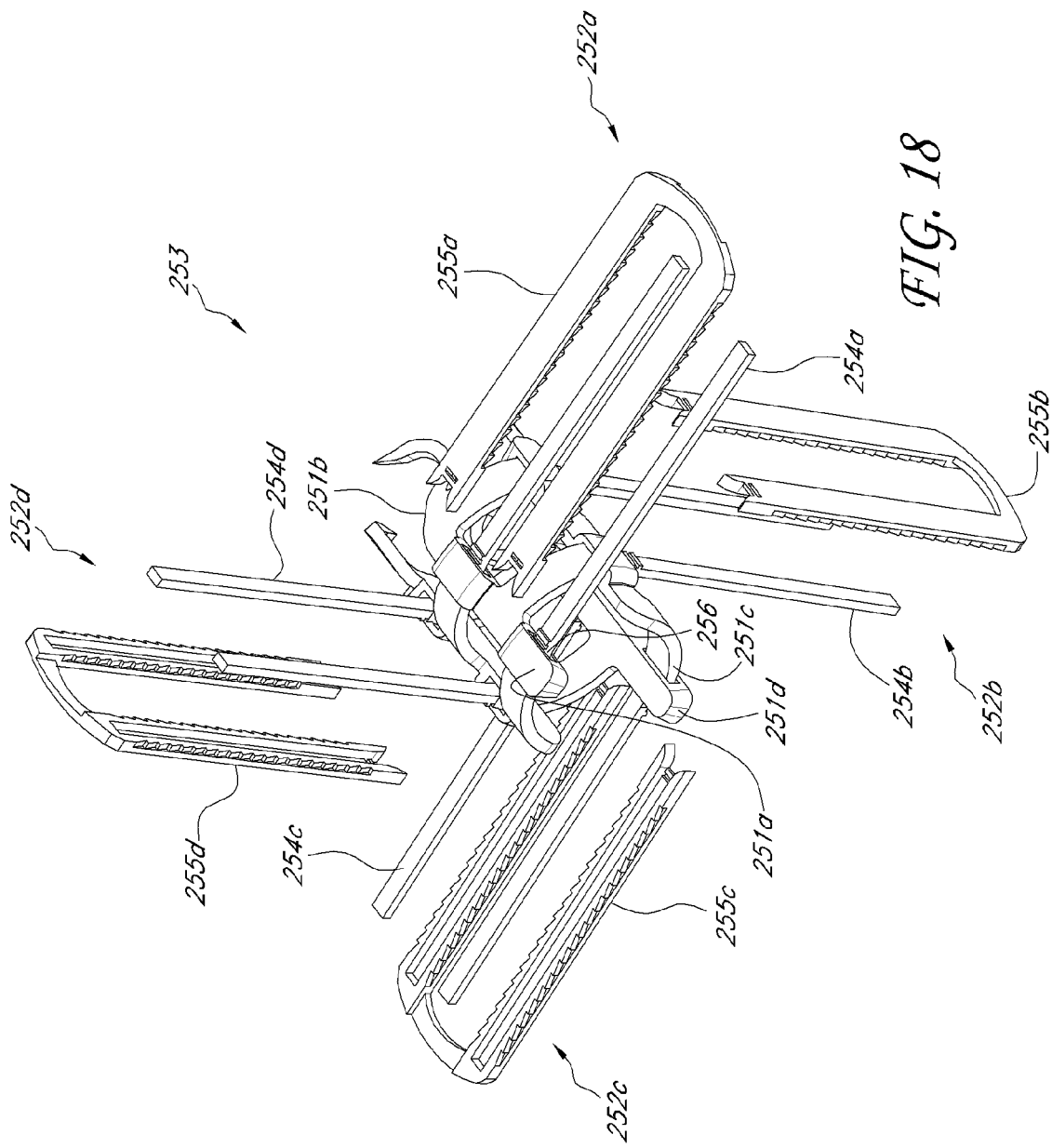
FIG. 18 is an exploded perspective view of a module of the stent shown in FIG. 17.

FIGS. 17 and 18 both illustrate the stent 250 generally in an unexpanded, pre-deployment state wherein ends of components of the stent protrude freely therefrom. In this regard, FIGS. 17-18 illustrate the stent during the assembly of the stent. After assembly is completed, the configuration of the stent can be manipulated further. For example, when the stent is mounted on a balloon and prepared for deployment, the protruding ends of the components of the stent can be bended or deformed to conform to an exterior surface of the stent. It is contemplated that the protruding ends of the components can be bended or deformed using mechanical means such as snaps, weaves, etc., thermal means, or by using a sheath to capture the protruding components to hold the protruding elements down in a final rolled configuration and thereby reduce the cross-sectional profile of the stent. For example, the protruding elements (such as frame elements discussed below) can be bended or deformed inwardly to conform to the exterior surface of the stent such that the cross-sectional profile of the stent becomes generally circular for facilitating placement of the stent within body lumens.

In accordance with the embodiment shown in FIG. 17, the stent 250 can comprise a plurality of interwoven strands 251a, 251b, 251c, 251d. Each of the strands 251a, 251b, 251c, 251d can comprise at least one frame element 252a, 252b, 252c, 252d, respectively. As illustrated in FIG. 17, each strand 251a, 251b, 251c, 251d can include at least one frame element, and in embodiments where multiple frame elements are used on each strand, the frame elements can be interconnected to each other via interconnection elements. The interconnection elements can be flexible and extend from a given frame element to an adjacent frame element. When assembled, FIG. 17 illustrates that the frame elements 252a, 252b, 252c, 252d of the strands 251a, 251b, 251c, 251d strand can form a single module 253. Additionally, the stent 250 can be formed to comprise several repeating modules 253', 253". The modules 253, 253', 253" can be identically configured such that the stent 250 is formed using a repeating structure. However, it is also contemplated that the modules 253, 253', 253" can be configured dissimilarly from each other in order to incorporate other features and characteristics as needed. For example, the stent 250 can be formed to include apertures that can allow access to side branches. Other various modifications to individual frame elements can also be made in other embodiments of the stent 250.

The number of modules 253 present in the stent 250 can correlate with the length of the stent 250. Thus, it is contemplated that stents 250 can be prepared having three, five, ten, or any number of modules 253, depending on the desired length. Furthermore, the number of strands can also be modified to provide a larger or smaller maximum diameter of the stent 250 in the expanded state. Thus, the embodiment shown in FIG. 17 having three modules and four strands is an exemplary embodiment to illustrate the interrelationships of the strands, the frame elements, and the module structures of the stent 250 and should not be construed as limiting.

FIG. 18 is an exploded perspective view of a module 253 of the stent shown in FIG. 17. The module 253 comprises the frame elements 252a, 252b, 252c, 252d of the respective strands 251a, 251b, 251c, 251d. The exploded view of FIG. 18 illustrates that each frame element 252a, 252b, 252c, 252d can be formed to comprise respective rail members 254a, 254b, 254c, 254d, coupling elements 255a, 255b, 255c, 255d, and at least one engagement aperture 256.

The rail members 254a, 254b, 254c, 254d can each comprise at least one rail, and are illustrated as having a pair of rails. Further, the coupling elements 255a, 255b, 255c, 255d can be formed to correspond to the configuration of the rail member, and accordingly, can include one or more sections that attaches to the respective rail(s) of the rail member. The engagement aperture 256 can be configured to receive a given rail member therethrough. In some embodiments, the stent can include an equal number of engagement apertures corresponding to the number of rail members. In this regard, after a rail member is passed through an engagement aperture, a coupling element can be attached to the rail member. The coupling members can be configured to provide a one-way movement of the rail member relative to the engagement aperture. As such, although the rail member may fit within the engagement aperture, the rail member assembled with the coupling element may only be able to pass through the engagement aperture in one direction, thus providing one-way expansion of the stent from an axially-radially nested unexpanded state to an expanded state. The coupling elements 255a, 255b, 255c, 255d are shown as being formed in pairs, in a U-shape, with sections thereof being connected to each other at respective ends. However, it is contemplated that the coupling elements can be formed in various shapes, such as an H-shape, a planar shape, etc.

In accordance with the embodiment of FIG. 18, the stent 250 can be formed with the rail members 254a, 254b, 254c, 254d first being interwoven into respective apertures of the frame elements 252a, 252b, 252c, 252d, and subsequently, the coupling elements 255a, 255b, 255c, 255d can be attached to the respective ones of the rail members 254a, 254b, 254c, 254d. In this regard, the assembly of the stent 250 can be done by interweaving adjacent strands having a desired number of modules 253. Further, a sufficient number of strands can be interwoven such that the stent 250 can obtain a desired cross sectional expansion diameter.

The rail members 254a, 254b, 254c, 254d and the coupling elements 255a, 255b, 255c, 255d can be interconnected or attached to one another using a variety of mechanisms and materials. For example, the coupling elements 255a, 255b, 255c, 255d can be attached to the rail members 254a, 254b, 254c, 254d using adhesives, bonding or joining processes, mechanical means, and the like. It is contemplated that the stent 250 can beneficially incorporate attachable coupling elements 255a, 255b, 255c, 255d and rail members 254a, 254b, 254c, 254d in order to generally simplify the stent configuration and facilitate construction and assembly thereof.

Figure 19:
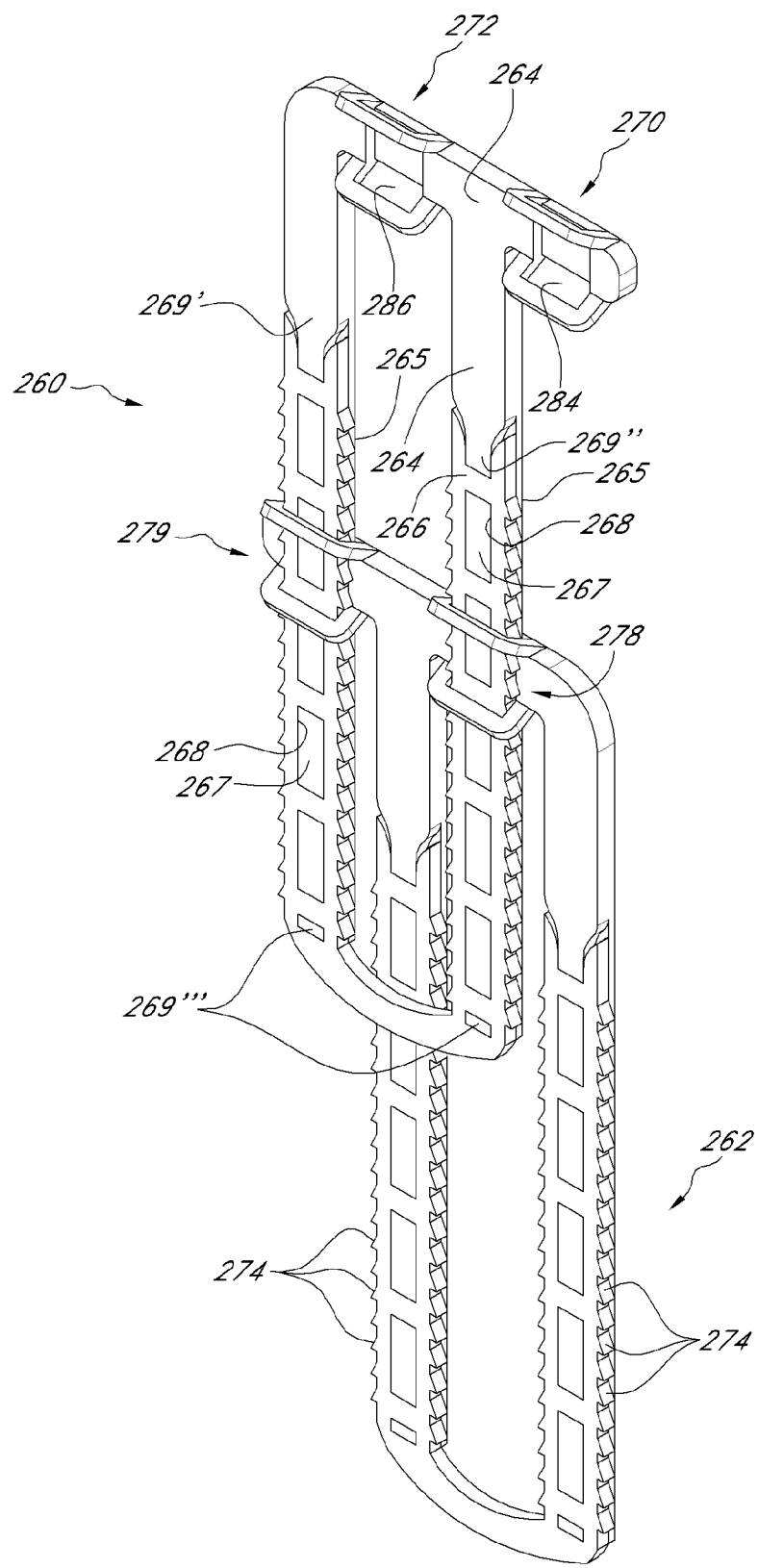
FIG. 19 is a perspective view of an embodiment of a frame element of the module shown in FIG. 18.

FIG. 19 is a perspective view of an embodiment of exemplary frame elements 260, 262 of a module, as shown in FIGS. 17 and 18. The frame element 260 can include a body section 264 and rail members 265 extending therefrom. In some embodiments, the rail members 265 can extend generally perpendicularly relative to the body section 264. The frame element 260 can also include a coupling element 266 that can be attached to the rail members 264.

In accordance with the embodiment of the frame element 260 shown in FIG. 19, the rail members 265 can comprise one or more protrusions 267 that can be received at respective securing points 268 of the coupling element 266. The protrusions 267 can be formed in any of a variety of geometric shapes and preferably extend from a base surface of the rail members 265. The securing points 268 can be formed as apertures or cavities and can be configured to receive the respective protrusions 267. In some embodiments, the protrusions 267 can be snap fit or press fit into the securing points 268 to attach the coupling element 266 to the rail member 265. Further, adhesives or other materials and processes can also be employed to securely attach the coupling element 266 to the rail member 265.

The rail member 265 can also comprise one or more alignment elements 269' and 269". These alignment elements 269' and 269", similarly to the protrusions 267, can be used to interconnect with portions of the coupling element 266. The alignment elements 269' and 269" can be employed in some embodiments to facilitate proper alignment and attachment of the coupling element 266 to the rail members 265.

Each frame element 260 and 262 can also be configured to include at least one or more engagement apertures, which can comprise one or more loops. FIG. 19 illustrates the engagement apertures as loops 270, 272 and 278, 279. However, it is noted that as in FIGS. 17-18, the engagement apertures can comprise individual loops or passages. Further, the engagement apertures can incorporate interior or exterior locking mechanisms, such as those described and illustrated above with respect to FIGS. 13A-B. The loops 270, 272 and 278, 279 can be formed integrally with the body sections of the frame elements. The loops 270, 272 and 278, 279 can be configured to allow the rail members of an adjacent frame element to be received therethrough. However, after the rail members are passed through the loops, and the coupling elements are attached to the rail members, the loops should be configured to allow one-way movement of the coupling elements relative to the frame element.

In such embodiments, the coupling element 266 of the frame element 260 can be formed to include at least one motion-limiting feature that can interact with the loops of the frame element 262, such as teeth 274 illustrated in FIG. 19. However, the motion-limiting feature can comprise various geometric configurations, not just the teeth 274. For example, the motion-limiting feature can refer to a widening shape of the coupling element such that the coupling element engages top or side portions of the loops as it is drawn therethrough. The motion-limiting feature can refer to a roughened surface or structures that allow one-way and/or step-wise passage of the coupling element relative to the loop. FIG. 19 illustrates teeth 275 that engage the loops 278, 279 generally on the sides thereof. However, as described below, FIG. 20 illustrates another embodiment wherein the motion-limiting member includes teeth that engage protruding corners of the loops.

Referring again to FIG. 19, the loops 278 and 279 of the frame element 262 illustrate that as the stent expands the coupling element 266 and the rail members 265 will be urged through the loops 278, 279. The coupling member 266 can be configured to engage the loops 278, 279 such that the frame element 260 is allowed one-way movement relative to the frame element 262.

In this regard, the loops 270, 272 and 278, 279 can be formed to include apertures of different shapes and designs. For example, the embodiment illustrated in FIG. 19 shows that the loops 270, 272 can include generally rectangular-shaped apertures 284, 286 (similarly illustrated for loops 278, 279 having the coupling element 266 received therein) that can engage teeth 274 of the coupling element 266.

Figure 20:
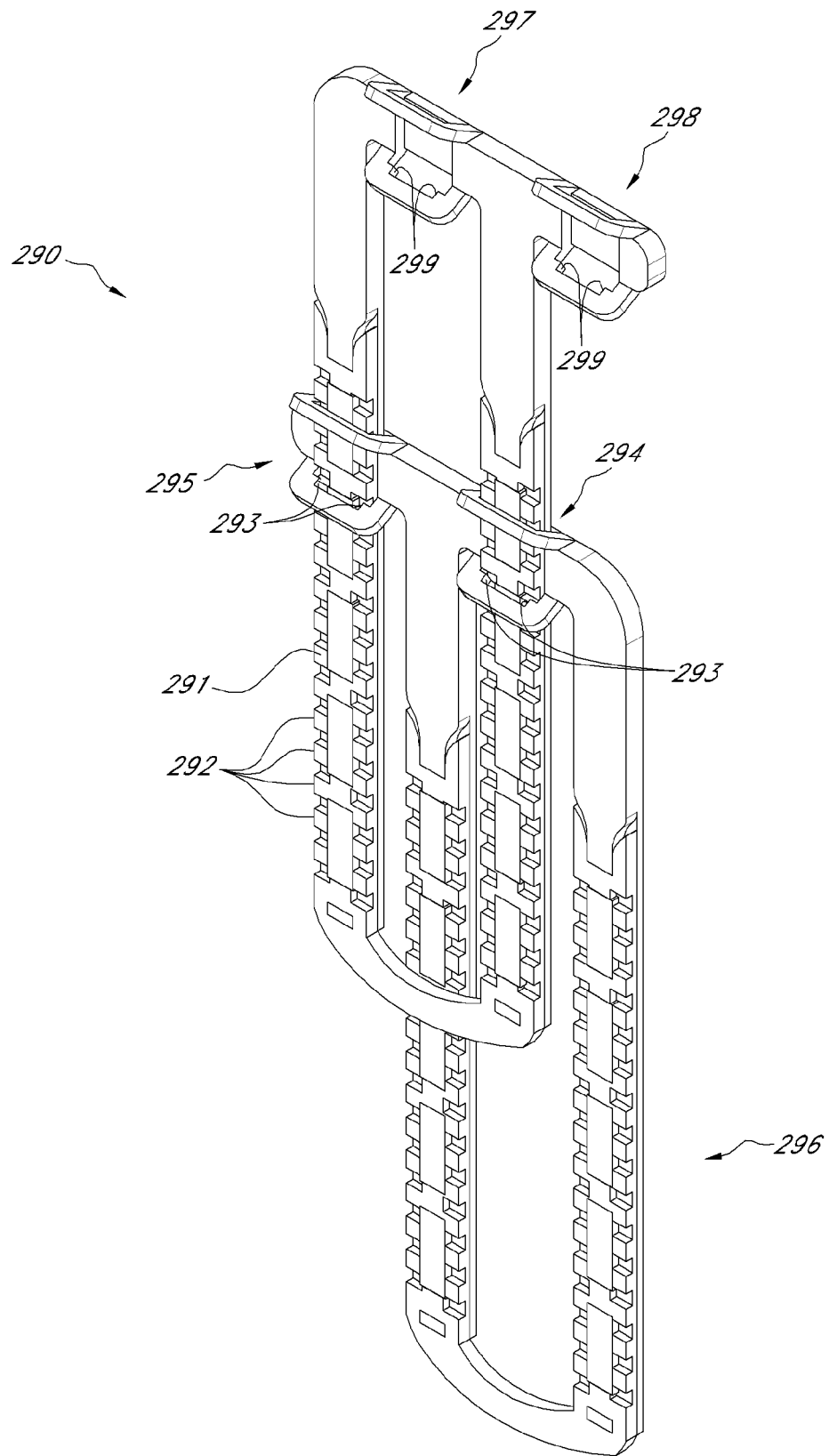
FIG. 20 is a perspective view of another embodiment of a frame element of the module shown in FIG. 18.

However FIG. 20 illustrates a perspective view of another embodiment wherein a frame element 290 comprises a coupling element 291 having a motion-limiting feature, shown as teeth 292, configured to loops 294, 295 of an adjacent frame element 296. In this embodiment, the loops 294, 295 are configured to comprise apertures having at least one internal corner 293 that can engage the teeth 292 of the coupling element 291. Loop elements 297, 298 (which are illustrated without a coupling element disposed therethrough) also illustrate the structure of the apertures and corners 299.

Accordingly, various embodiments can be provided wherein the coupling element is attached to the rail member after the rail member is inserted through the loop of an adjacent frame element. Further, the one-way movement of the frame elements relative to each other can be facilitated through the engagement of the coupling element with the loop.

Telescoping Slide-and-Lock Stent Inventions

Figure 21A:
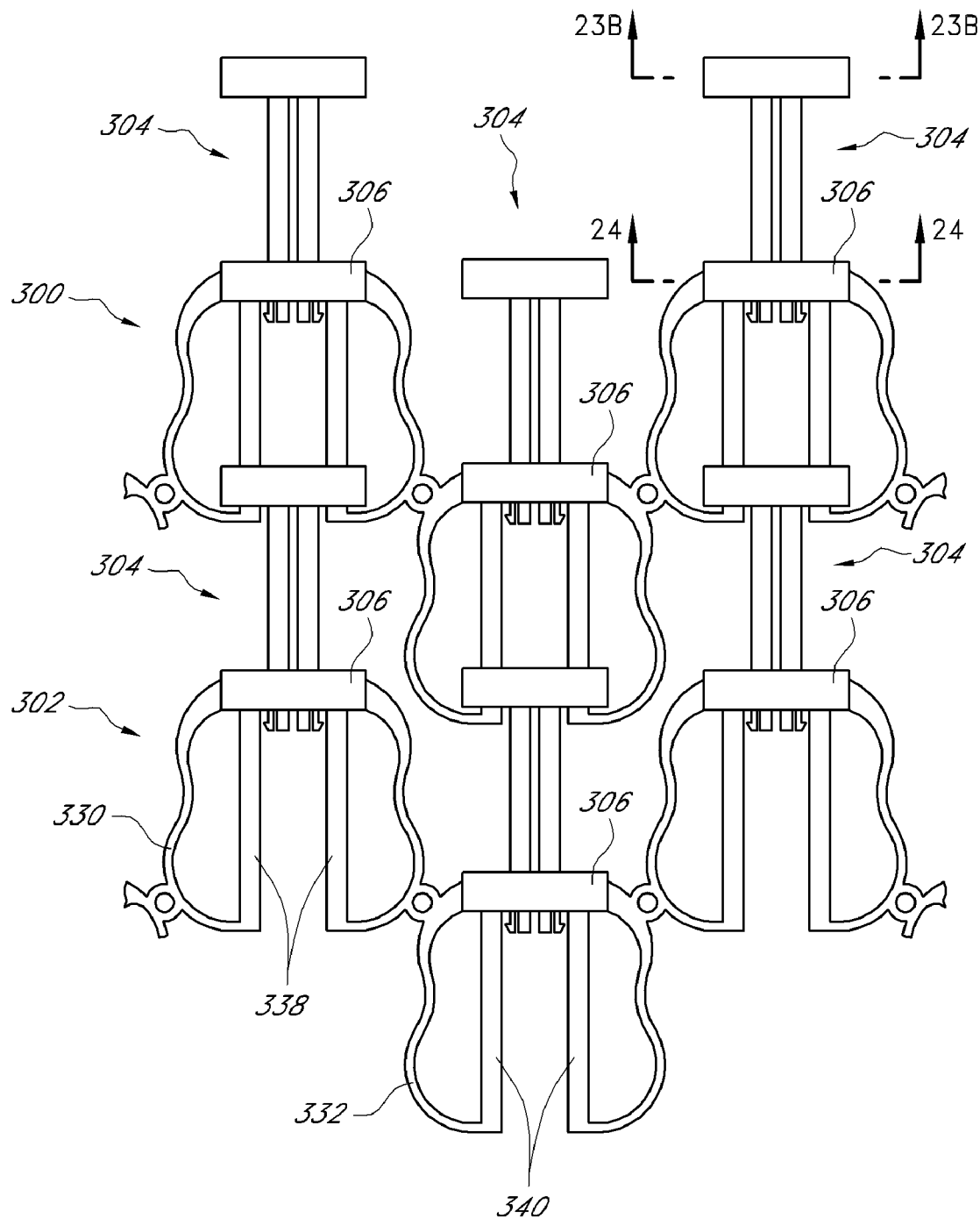
FIG. 21A is a top view of a portion of an axially-radially nested stent in an expanded state, in accordance with yet another embodiment.

In accordance with yet another of the inventions, a telescoping slide-and-lock stent is provided that can be configured in accordance with the exemplary embodiment shown in FIGS. 21A-24. FIG. 21A is a top plan view of the axially-radially nested stent in an expanded state having first and second linkage components 300, 302, with the stent being in an expanded state. FIG. 21B is a top plan view of the stent shown in FIG. 21A wherein the stent is in a nested state. As discussed above with other embodiments of the stent, the embodiment illustrated in FIGS. 21A-24 can likewise comprise a tubular member that has circumferential and longitudinal axes. The tubular member of the embodiments illustrated in FIGS. 21A-24 can comprise at least one linkage component. However, it can also include various linkage components, such as linkage components 300, 302 that interconnect with various at least one slide and lock element 304, and at least one interconnector block 306. While FIGS. 21A-B illustrate the assembled state of these various components of the tubular member, FIGS. 22-24 provide detailed views of these components and will be described below.

Figure 21B:
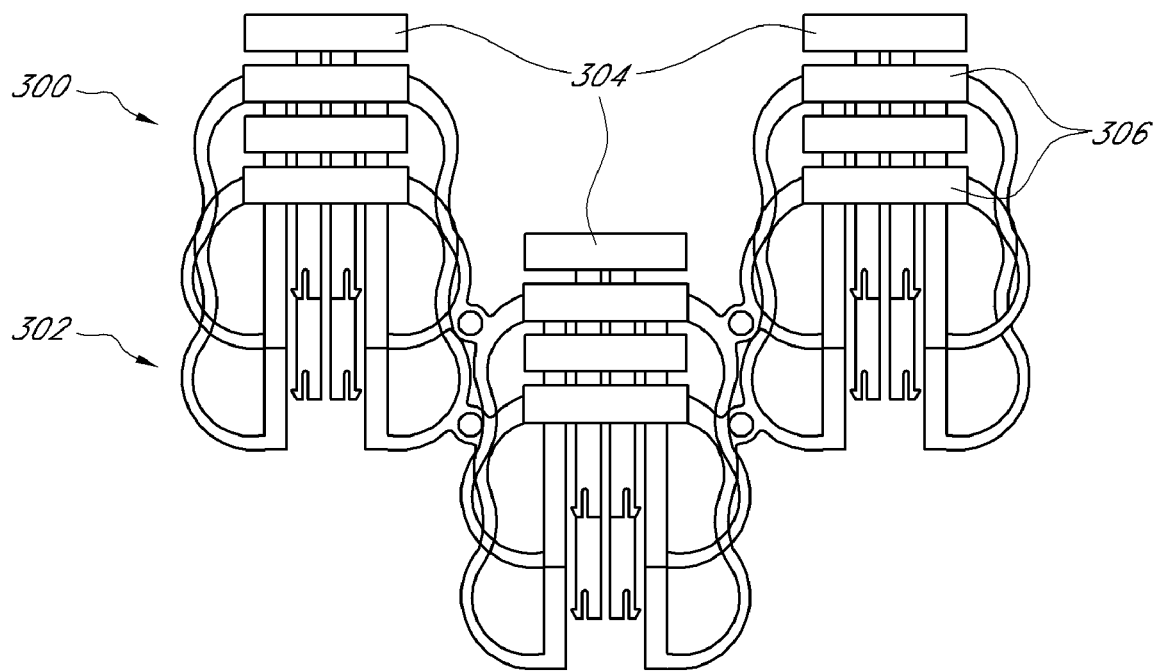
FIG. 21B is a top view of the axially-radially nested stent of FIG. 21A in a nested or unexpanded state.

With further reference to FIGS. 21A-B, the linkage components 300, 302 can be formed to a desired axial or longitudinal length as desired. As mentioned above in discussing FIGS. 14-16, embodiments discussed with respect to FIGS. 21-24 can also be formed to a desired length and need only be interconnected with other linkage components in the circumferential direction, if desired, to form the stent to have a desired diameter in collapsed and/or expanded states. For example, individual linkage components 300, 302 can be injection molded at a desired length and then circumferentially interconnected with other linkage components to form the stent.

FIG. 22 is a top plan view of an individual linkage component 300. The linkage component 300 can comprise at least one section, and as shown in FIG. 21A, can comprise multiple sections that are interconnected in a side-to-side longitudinal configuration. As described above, the length of the linkage component 300, which corresponds to the number of interconnected sections, can also correspond to the desired stent length. Further, although the sections can be connected in a simple side-to-side configuration, FIGS. 21A-22 illustrate that first and second sections 320, 322 of the linkage component 300 can be arranged in a circumferentially offset configuration. In addition, it is contemplated that the linkage component 300 can also include at least one central joint 324 that interconnects sections of the linkage component. The central joint 324 can interconnect the first and second sections 320, 322 of the linkage component 300 to each other in a side-to-side manner.

In accordance with another embodiment, the section of the linkage component can include a flexible portion and a rail portion interconnected with the flexible portion. For example, as shown in FIG. 22, each of the first and second sections 320, 322 can be configured to include pairs of flexible portions 330, 332, respectively. In addition, the first and second sections 330, 332 can also be configured to include respective elongate rail portions 338, 340, which are interconnected with the respective ones of the flexible portions 330, 332.

It is contemplated that embodiments of the stent can be formed using only linkage components, slide-and-lock elements, and interconnector blocks that are each fabricated as individual integral components. However, embodiments discussed herein may be constructed using, for example, linkage components that are formed by combining various other components to form a composite linkage component. Likewise, the slide-and-lock elements and the interconnector blocks can be formed as a combination of other individual components.

Furthermore, in some embodiments it is contemplated that the linkage component and the interconnector block can be integrally formed as an individual component. For example, as shown in FIG. 22, the interconnector block 306 can be disposed along the flexible portions 330, 332 of the section of the linkage component. In particular, FIG. 22 shows that interconnector blocks 306 can each be dispose at approximately a midpoint of the flexible portions 330, 332 with the interconnector block 306 being oriented substantially perpendicularly relative to the pairs of rail portions 338, 340.

FIGS. 21A-22 illustrate an embodiment of the linkage component 300 wherein the flexible portions 330, 332 are configured to deflect upon application of a bending, compressive, or tensile force to the tubular member. In order to do so, the flexible portions 330, 332 can be variously configured. The illustrated embodiments illustrate that the flexible portions 330, 332 can be arcuate in shape and in order to reduce and/or eliminate sharp corners at which stress concentrations may develop and result in linkage component and/or stent failure.

As illustrated in FIG. 21A, the pairs of elongate rail portions 338, 340 can be coupled to the respective ones of the flexible portions 330, 332 along the lengths thereof. In particular, the pairs of elongate rail portions 338, 340 can each define proximal ends 342, 344, respectively, and distal ends 346, 348, respectively. In the illustrated embodiment, the proximal ends 342, 344 are coupled to opposing ends of the flexible portions 330, 332. In addition, it is contemplated that the pairs of elongate rail portions 338, 340 can be attached to the flexible portions 330, 332 such that the elongate rail portions 338, 340 are oriented generally parallel relative to each other.

In addition, the pairs of elongate rail portions 338, 340 can be configured to include a plurality of engagement teeth 350 disposed along at least one side thereof. These engagement teeth 350 can be used to facilitate one-way circumferential expansion of the stent. However, in other embodiments, the pairs of elongate rail portions 338, 340 can be configured in order to frictionally engage the slide-and-lock element 304 for providing one-way circumferential expansion of the stent. Such engagement can be achieved as described herein with respect to other embodiments.

Referring now to FIGS. 23A and 23B, the slide-and-lock element 304 can be configured to include a head portion 360 and an elongate neck portion 362. The head portion 360 and the neck portion 362 can be integrally formed from a continuous piece of material. In some embodiments, the slide-and-lock element 304 can be configured to interconnect pairs of linkage components 300, 302 as well as to interconnect the linkage components 300, 302 with an adjacent pair of linkage components, as illustrated in FIG. 21A. As such, the slide-and-lock element 304 preferably extends generally in the circumferential direction intermediate pairs of linkage components. In various embodiments, the slide-and-lock element 304 facilitates the one-way circumferential expansion of the tubular member.

In some embodiments, the head portion 360 of the slide-and-lock element 304 can include a pair of apertures 364, 366 that can be sized and configured to receive the rail portions of an adjacent linkage component. The apertures 364, 366 can be configured as other apertures described above, with geometric or frictional elements to facilitate one-way movement of the slide-and-lock element 304 relative to the linkage component 300 In this regard, the rail portions received within the respective ones of the apertures 364, 366 can be longitudinally spaced in order to allow interposition of the neck portion 362 therebetween. Therefore, as shown in FIGS. 21A-B, the head portion 360 can be operatively coupled to an adjacent linkage component and be configured to provide one-way movement relative to the linkage components.

In accordance with another aspect, the neck portion 362 of slide-and-lock element 304 can be configured to interconnect with the interconnector block 306. In this regard, as illustrated in FIG. 24, the interconnector block 306 can have left and right ends 370, 372 and left and right connection points 374, 376 disposed at the respective ones of the left and right ends 370, 372. As best seen in FIG. 21A, the interconnector block 306 can be coupled to the flexible sections 330, 332 of the linkage component and to the distal ends 346, 348 of the elongate rail elements thereof. As mentioned above, in some embodiments, the interconnector block 306 can be integrally formed with the flexible sections 330, 332.

In some embodiments, the interconnector block 306 can further comprise a pair of central connection points 378, 380 disposed intermediate the left and right connection points 374, 376. The central connection points 378, 380 can be sized and configured to attachably receive the distal ends 346, 348 of the rail portions 338, 340 of the linkage component 300. With reference again to FIG. 22, the distal ends 346, 348 can be configured to define latch elements 368a, 368b, such as protrusions, widened sections, hooks, etc. Further, the central connection points 378, 380 can include interior retention recesses 369a, 369b that can matably engage the respective ones of the latch elements 368a, 368b of the distal ends 346, 348 of the rail portions 338, 340. Accordingly, the distal ends 346, 348 can be clipped or snapped into the central connection points 378, 380. The configuration and orientation of the left and right connection points 374, 376 and the central connection points 378, 380 can be varied according to design requirements and by one of skill in the art.

In accordance with another aspect shown in FIGS. 22 and 24, the interconnector block 306 can further comprise at least one engagement aperture 382 and preferably another engagement aperture 384. The engagement aperture 382 can be configured to receive the neck portion 362 of the slide-and-lock element 304 in order to facilitate one-way circumferential movement of the slide-and-lock element 304 relative to the interconnector block 306.

In some embodiments, wherein the interconnector block 306 includes a pair of engagement apertures 382, 384. In such embodiments, the elongate neck portion 362 of the slide-and-lock element 304 can be configured to include a pair of elongate rails 390, 392. It is contemplated that the elongate rails 390, 392 can include engagement means disposed thereon, such as a plurality of teeth disposed at least one side or surface of the rails 390, 392. In other embodiments, the elongate rails 390, 392 can be sized and configured to frictionally engage the interconnector block 306. The elongate rails 390, 392 can also each be configured to include stop elements 393a, 393b. The stop elements 393a, 393b can be configured to prevent the elongate rails 390, 392 from disengaging with the engagement apertures 382, 384 of the interconnector block 306. As shown, the stop elements 393a, 393b can be configured as lateral protrusions extending from the distal ends of the elongate rails 390, 392. However, the stop elements 393a, 393b can also be configured as wider portions of the elongate rails 390, 392, frictional elements, or otherwise to prevent the elongate rails 390, 392 from being fully withdrawn from the engagement apertures 382, 384.

In accordance with yet another embodiment, as illustrated in FIGS. 23B and 24 that show cross-sectional views of the embodiment illustrated in FIG. 21A, the linkage components 300, 302 can define a component radial thickness 394 and the interconnector block can define a block radial thickness 396. It is contemplated that the component radial thickness 394 can be less than the block radial thickness 396, such that the elongate rails 338, 340 of the linkage components 300, 302 can easily pass through the various engagement apertures of the interconnector block. Likewise, as shown in FIG. 23B, the head portion 360 of the slide-and-lock element 304 can define a head thickness 398 and the elongate neck portion 362 can define a neck thickness 399. Accordingly, the neck thickness 399 is preferably less than the head thickness 398, and these thicknesses 398, 399 can likewise correspond to the thicknesses 394, 396 of the linkage components 300, 302 and the interconnector block 306 in order to facilitate proper engagement of the various components.

As illustrated in FIGS. 21A-B, the head portion 360 of the slide-and-lock element 304 and the interconnector block 306 of the linkage component 300 can be oriented generally parallel relative to each other when the stent is assembled. In this regard, the longitudinal axes of the slide-and-lock element 304 and the interconnector block 306 can both be oriented substantially parallel relative to the longitudinal axes of the tubular member. Furthermore, the neck portion 362 of the slide-and-lock element 304 can be oriented in the circumferential direction in order to facilitate expansion of the stent in the circumferential direction.

In use, the stent of such embodiments can be formed by inserting the distal ends 346, 348 of the pairs of rail portions 338, 340 into the apertures 364, 366 of the slide-and-lock element, and then coupling the distal ends 346, 348 of the rail portions 338, 340 to the central connection points 378, 380 of the interconnection block 306. Further, the elongate rails 390, 392 of the neck portion 362 of the slide-and-lock element 304 can be inserted into the engagement apertures 382, 384 of an interconnection block 306 of an adjacent linkage section. The number of linkage sections used in the stent can determine the radius of the stent.

Modular Dual Expansion Stent Inventions

FIGS. 25-28 illustrate an embodiment of a modular dual expansion stent. As shown therein, the axially-radially nested stent can be expandable from an axially-radially nested unexpanded state (shown in FIGS. 25-26) to an expanded state (shown in FIG. 28). The stent comprises a tubular member having longitudinal and circumferential axes.

Figure 25:
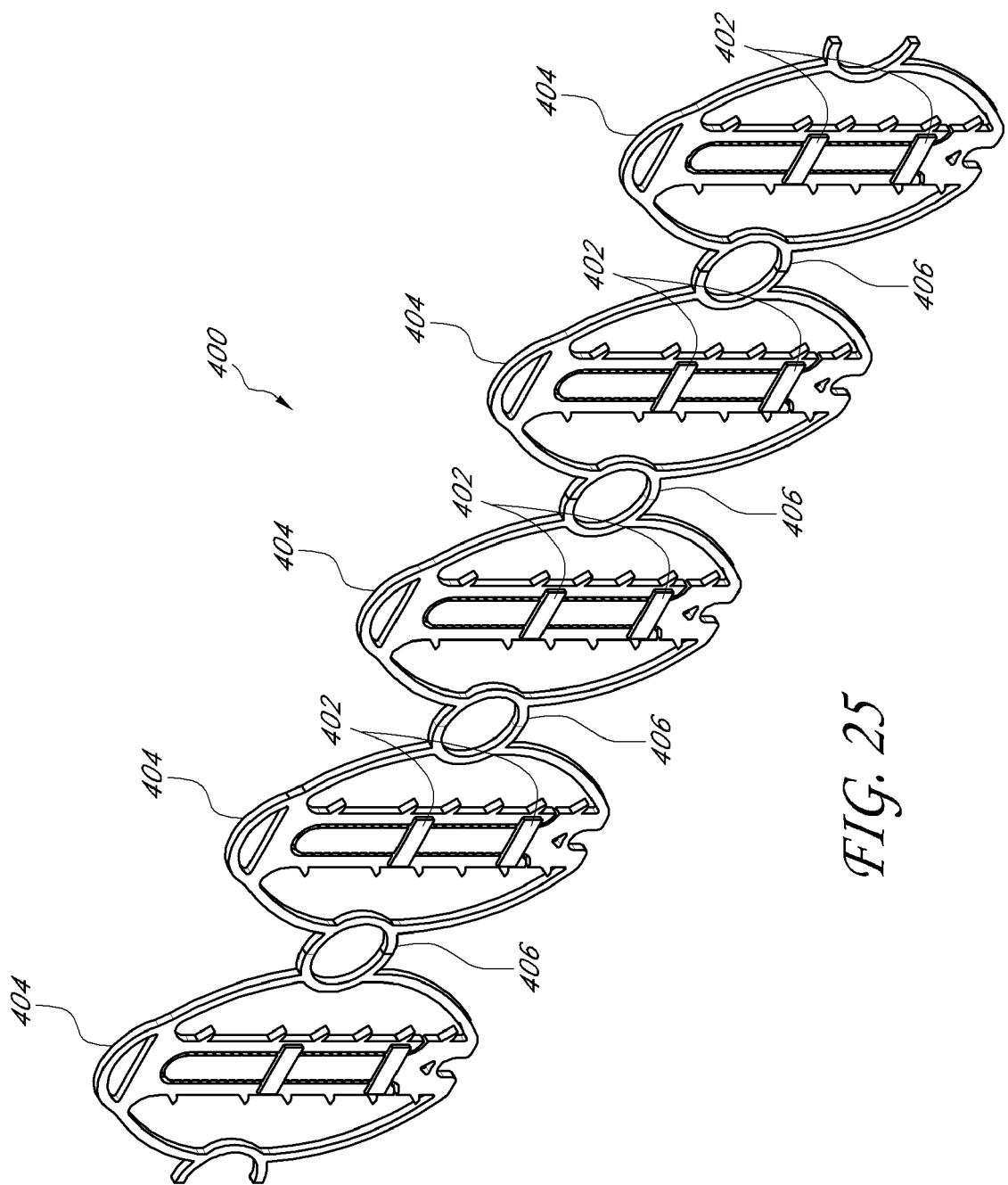
FIG. 25 is a perspective view of a portion of an axially-radially nested stent in a nested or unexpanded state, in accordance with yet another embodiment.

The tubular member of the stent can comprise a plurality of strands 400 and at least one stabilizer block 402. The strands 400 can each include a plurality of interconnected expandable modules 404, as shown in FIG. 25. The modules 404 can be interconnected in an end-to-end manner via joints 406 interposed between the modules 404. The joints 406 can be configured to provide a degree of flexibility and allow some movement between adjacent modules 404. The strands 400 can be disposed along the longitudinal axis of the tubular member, and in preferred embodiments, are disposed generally parallel relative to the longitudinal axis.

As discussed above with respect to FIGS. 14-24, that the strands 400 can also be formed to a desired axial or longitudinal length. Embodiments discussed with respect to FIGS. 25-28 can also be formed to a desired length and need only be interconnected with another strand in the circumferential direction. For example, individual strands 400 can be injection molded at a desired length and then circumferentially interconnected with other strands to form the stent.

In some embodiments, such as that shown in FIG. 26, each module 404 can be configured to provide an individual mode of circumferential expansion for the stent. For example, a center region of the module 404 can be configured to translate to cause a periphery of the module 404 to widen or elongate in the circumferential direction. As described further below, the interaction of adjacent strands can be used to provide a group mode of circumferential expansion to the stent. As will be appreciated, the dual expansion capabilities of the stent of the present embodiment provide for a significant advancement and improvement such that the stent can be more compact in the collapsed, axially-radially nested state.

Referring to FIG. 26, the module 404 can comprise first and second portions 410, 412. The first portion 410 can be disposed at a bottom end 408 of the module 404 and the second portion 412 can be disposed at an upper end 409 of the module 404. The first and second portions 410, 412 can be interconnected via opposing flexible portions 414, 416. The opposing flexible portions 414, 416 preferably extend intermediate the first and second portions 410, 412 and form an outer boundary for the module 404. Further, the opposing flexible portions 414, 416 can be configured to allow the module 404 to expand from an unexpanded state to an expanded state. As described below, the expansion of the module 404, as shown from FIG. 26 (unexpanded) to FIG. 28 (expanded) can require the flexible portions 410, 412 to be deflected or stretched from a resting position. As such, the illustrated embodiment shows that the module 404 can be generally ovular in shape.

The first portion 410 can comprise a belt component 420 extending therefrom in the circumferential direction. The second portion 412 can have a guide rail component 422 and a buckle component 424. The guide rail component 422 can be configured to extend in the circumferential direction adjacent and generally parallel to the belt component 420. The guide rail component 422 can have at least one lateral protrusion 426, such as a tooth. The buckle component 424 can be sized and configured to receiving therethrough a belt component and a guide rail component from another module of another circumferentially adjacent strand for interconnecting the strands about the circumferential axis of the tubular member. In this regard, the buckle component 424 can be operative to slide along the guide rail component of the adjacent module and engage the at least one lateral protrusion for facilitating one-way circumferential movement of the buckle component of the module relative to the guide rail component of the other module for facilitating one-way circumferential expansion of the stent In addition, the stabilizer block 402 is preferable sized and configured to be attachable to the guide rail component 422. The stabilizer block 402 can be sized and configured to engage the belt component 420 such that relative movement between the guide rail component 422 and the belt component 420 produces one-way circumferential expansion of the module 404 to provide a second means of circumferential expansion of the stent.

The stabilizer block 402, as shown in FIG. 27, can include a central aperture 430 wherethrough the belt component 420 can be passed. The central aperture 430 can be configured to engage the belt component 420. For example, in some embodiments, the belt component 420 can include a plurality of engaging teeth 432, as shown in FIGS. 26 and 24. The engaging teeth 432 can be configured such that they are allowed one-way movement relative to the stabilizer block 402. Thus, in an embodiment, the belt component 420 can be retracted from the stabilizer block 402, but cannot reenter. In other embodiments, the teeth 432 could be replaced by detents. The detents could mate with corresponding structures of the stabilizer block 402. Accordingly, the detents could facilitate one-way movement of the belt component 420 relative to the stabilizer block 402. It is contemplated that the force required to cause expansion would be far less than the force required to cause collapse of the stent.

In the embodiment shown in FIG. 26, a central portion of the stent can be configured such that the guide rail component 422 includes a pair of circumferentially extending side rails 434 defining a cavity 436 therebetween. In the illustrated embodiments, the cavity 436 is sized and configured to receive the belt component 420 therein. The individual mode of expansion can occur where during expansion of the stent, the belt component 420 is drawn out of the cavity 436, moving relative to the side rails 434 of the guide component 422. This movement can be one-way in some embodiments, such as where the engaging teeth 432 engage the stabilizer block 402. Further, an engaging mechanism, similar to the engaging teeth 432, can be disposed on the guide rail component 422 and/or the stabilizer block 402 and configured to engage the belt component 420 to facilitate one-way movement thereof. However, it is also contemplated that alternative configurations can also be devised wherein the belt component 420 and the guide rail component 422 are operative to achieve a one-way relative movement without use of cavity 436 in a manner distinct from the illustrated embodiment.

Figure 28:
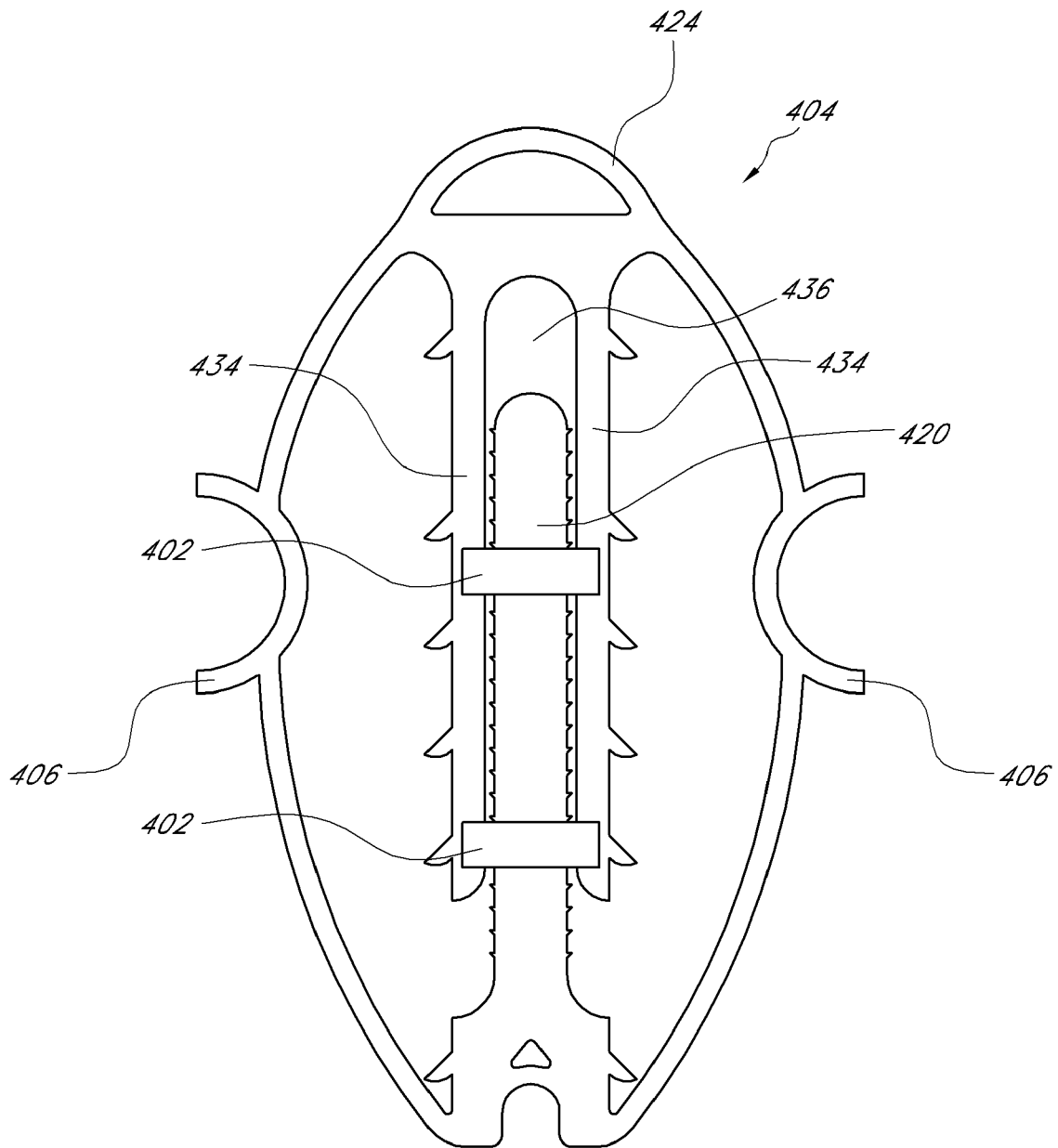
FIG. 28 is a top view of the module of the stent of FIG. 25 in an expanded state.

In accordance with another aspect, the stabilizer block 402 can be interposed between the side rails 434 of the guide rail component 422. The stabilizer block 402 can be mechanically, adhesively, or otherwise attached thereto. Further, as illustrated in FIGS. 25, 26, and 28, each module 404 can use a pair of stabilizer blocks 402 in order to ensure that the belt component 420 and the guide rail component 422 are properly engaged and positioned relative to one another. Further, the central aperture 430 of each of the stabilizer blocks 402 can be configured to engage the belt component 420 disposed therethrough for providing the one-way movement of the belt component 420 relative to the guide rail component 422.

The group mode of expansion can be realized as a result of the relative movement of interconnected, adjacent strands 400 in the circumferential direction. The buckle component 424 can be configured to slidably engage the guide rail component 422 such that the buckle component can allow circumferential displacement of a strand 400 relative to an adjacent strand. As the buckle component 424 slides down the guide rail component 422, the buckle component 424 can cause the lateral protrusions 426 to deflect, allowing the buckle component 424 to move further toward the bottom end of the module. As shown in FIG. 26, the first portion 410 can also include lateral protrusions 450 that can be configured to lock the stent, and particularly the buckle component 424, into an expanded configuration.

In accordance with some embodiments, the stent of such embodiments can be assembled by threading the buckle component 424 onto the belt component 420. In this regard, the guide rail component 422 can be separated from the side rails 434 and the buckle component 424 can be initially threaded onto either of the guide rail component 422 or the side rails 434, with the remaining component being threaded into the buckle component 424 until the entire belt component 420 is threaded into the buckle component 424.

Alternatively, as shown in FIG. 26, the buckle component 424 can have a split loop 460 that allows the buckle component 424 to be opened in order to thread the belt component 422 thereinto. The split loop 460 can later be sealed or rejoined through bonding, such as laser, solvent, ultrasonic, adhesive, heat, or otherwise. Once the belt component 422 is threaded into the buckle component 424, the buckle component 424 can ratchet along the length of the belt component 422, using the as the stent moves from an unexpanded to an expanded state.

In this regard, some embodiments are configured such that the stent initially begins expanding through the group mode of expansion due to relative movement of the buckle components and belt components of adjacent strands. Once the buckle components of adjacent strands have ratcheted all of the way to the end of the belt component (or where no further expansion therebetween is possible), the individual mode of expansion can begin, i.e., the center regions of each expandable module can begin their expansion process. As detailed above, the expansion of the center regions can occur when the guide rail component 422 and the side rails 434 of the belt component 420 move relative to each other.

Therefore, some embodiments of the stent can expand first due to the relative movement of adjacent strands (group mode of expansion), and second, due to the relative movement of portions of the expandable modules (individual mode of expansion). However, various embodiments are also contemplated wherein multiple modes of expansion can be created and manipulated to occur in varying orders and/or simultaneously.

Lamination Manufacturing Process Embodiments

Stents in accordance with embodiments can be fabricated or created using a wide variety of manufacturing methods, techniques and procedures. These include, but are not limited to, laser processing, milling, stamping, forming, casting, molding, bonding, welding, adhesively fixing, and the like, among others.

In some embodiments, stent features and mechanisms can be created in a generally two dimensional geometry and further processed, for example by utilizing, but not limited to, bonding, lamination and the like, into three dimensional designs and features. In other embodiments, stent features and mechanisms can be directly created into three dimensional shapes, for example by utilizing, but not limited to, processes such as injection molding and the like.

In certain embodiments, stents can be fabricated by using an injection molding process, technique or method. For example, an injection molding process or the like, among others, can be used to form stent rows as integral units. The axially extending rows can then be connected and rolled into a tubular form in the collapsed state.

In some embodiments, a lamination stack can used to fabricate the stent rows by a lamination process in accordance with one embodiment. The axially extending rows can then be connected and rolled into a tubular form in the collapsed state.

The lamination stack, in some embodiments, generally can comprise three sheets or pallets which can have the desired features formed thereon, for example, by laser cutting, etching and the like. The pallets can be aligned and joined, for example, by bonding, welding and the like to form a unit. The excess material (e.g., side and end rails) can be removed to form the stent rows. The pallets can include various circumferentially nesting features such as male and female articulating and/or ratcheting designs to control and limit the diameter in collapsed and fully deployed states.

Combination Circumferentially and Axially Nesting Embodiments

Some stent embodiments provide at least one stent structural element that efficaciously can comprise a combination of radially and axially nesting features of a stent, as required or desired. Certain embodiments of axially nested stents are disclosed in co-pending U.S. patent application Ser. No. 11/196,800, filed Aug. 2, 2005, the disclosure of which is hereby incorporated by reference herein.

Metal Stents and Methods of Manufacturing

Preferred materials for making the stents in accordance with some embodiments include cobalt chrome, 316 stainless steel, tantalum, titanium, tungsten, gold, platinum, iridium, rhodium and alloys thereof or pyrolytic carbon. In still other alternative embodiments, the stents can be formed of a corrodible material, for instance, a magnesium alloy. Although preferred stent embodiments have been described as being conventional balloon expandable stents, those skilled in the art will appreciate that stent constructions according to embodiments can also be formed from a variety of other materials to make a stent crush-recoverable. For example, in alternative embodiments, such as self expandable stents, shape memory alloys that allow for such, such as Nitinol and Elastinite®, can be used in accordance with embodiments.

Preferred methods of forming the individual elements from metal sheets can be laser cutting, laser ablation, die-cutting, chemical etching, plasma etching and stamping and water jet cutting of either tube or flat sheet material or other methods known in the art which are capable of producing high-resolution components. The method of manufacture, in some embodiments, depends on the material used to form the stent. Chemical etching provides high-resolution components at relatively low price, particularly in comparison to high cost of competitive product laser cutting. Some methods allow for different front and back etch artwork, which could result in chamfered edges, which can be desirable to help improve engagements of lockouts. Further one can use plasma etching or other methods known in the art which are capable of producing high-resolution and polished components. The embodiments disclosed herein are not limited to the means by which stent or stent elements can be fabricated.

Once the base geometry is achieved, the elements can be assembled numerous ways. Tack-welding, adhesives, mechanical attachment (snap-together and/or weave together), and other art-recognized methods of attachment, can be used to fasten the individual elements. Some methods allow for different front and back etch artwork, which could result in chamfered edges, which can be desirable to help improve engagements of lockouts. In one preferred method of manufacture, the components of the stent can be heat set at various desired curvatures. For example, the stent can be set to have a diameter equal to that of the deflated balloon, as deployed, at a maximum diameter, or greater than the maximum diameter. In yet another example, elements can be electropolished and then assembled, or electropolished, coated, and then assembled, or assembled and then electropolished.

Polymeric Stents

While metal stents possess certain desirable characteristics, the useful lifespan of a stent is estimated to be in the range of about 6 to 9 months, the time at which in-stent restenosis stabilizes and healing plateaus. In contrast to a metal stent, a bioresorbable stent cannot outlive its usefulness within the vessel. Moreover, a bioresorbable stent could potentially be used to deliver a greater dose of a therapeutic agent, deliver multiple therapeutic agents at the same time or at various times of its life cycle, to treat specific aspects or events of vascular disease. Additionally, a bioresorbable stent can also allow for repeat treatment of the same approximate region of the blood vessel. Accordingly, there remains an important unmet need to develop temporary (i.e., bioresorbable and/or radiopaque) stents, wherein the polymeric materials used to fabricate these stents can have the desirable qualities of metal (e.g., sufficient radial strength and radiopacity, etc.), while circumventing or alleviating the many disadvantages or limitations associated with the use of permanent metal stents.

In one preferred embodiment, the stent can be formed from biocompatible polymers that are bio-resorbable (e.g., bio-erodible or biodegradable). Bio-resorbable materials can be preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof. For additional information, see U.S. Pat. Nos. 4,980,449, 5,140,094, and 5,264,537, the disclosures of each of which are incorporated by reference herein.

In one mode, the degradable materials can be selected from the group consisting of poly(glycolide-trimethylene carbonate), poly(alkylene oxalates), polyaspartimic acid, polyglutarunic acid polymer, poly-p-dioxanone, poly-.beta.-dioxanone, asymmetrically 3,6-substituted poly-1,4-dioxane-2,5-diones, polyalkyl-2-cyanoacrylates, polydepsipeptides (glycine-DL-lactide copolymer), polydihydropyranes, poly-alkyl-2-cyanoacrylates, poly-.beta.-maleic acid (PMLA), polyalkanotes and poly-.beta.-alkanoic acids. There are many other degradable materials known in the art. (See e.g., Biomaterials Science: An Introduction to Materials in Medicine (29 Jul. 2004) Ratner, Hoffman, Schoen, and Lemons; and Atala, A., Mooney, D. Synthetic Biodegradable Polymer Scaffolds. 1997 Birkhauser, Boston; each of which are incorporated herein by reference).

Further still, in a more preferred embodiment, the stents can be formed of a polycarbonate material, such as, for example, tyrosine-derived polycarbonates, tyrosine-derived polyarylates, tyrosine-derived diphenol monomers, iodinated and/or brominated tyrosine-derived polycarbonates, iodinated and/or brominated tyrosine-derived polyarylates. For additional information, see U.S. Pat. Nos. 5,099,060, 5,198,507, 5,587,507, which was reissued in RE37,160, U.S. Pat. No. 5,670,602, which was reissued in RE37,795, U.S. Pat. Nos. 5,658,995, 6,048,521, 6,120,491, 6,319,492, 6,475,477, 5,317,077, and 5,216,115, and U.S. application Ser. No. 09/350,423, the disclosures of each of which are incorporated by reference herein. In another preferred embodiment, the polymer can be any of the biocompatible, bioabsorbable, radiopaque polymers disclosed in: U.S. Patent Application Nos. 60/852,513, 60/852,471, 60/601,526, 60/586,796, 60/866,281, 60/885,600, U.S. Ser. Nos. 10/952,202, 11/176,638, 11/335,771, 11/200,656, 11/024,355, 10/691,749, 11/418,943, and 11/873,362; U.S. Patent Publication No. US26115449A1; U.S. Pat. Nos. 6,852,308 and 7,056,493; and PCT Application Nos. PCT/US2005/024289, PCT/US2005/028228, PCT/US07/01011, and PCT/US07/81571, the disclosures of each of which are incorporated herein by reference thereto.

Natural polymers (biopolymers) include any protein or peptide. Preferred biopolymers can be selected from the group consisting of alginate, cellulose and ester, chitosan, collagen, dextran, elastin, fibrin, gelatin, hyaluronic acid, hydroxyapatite, spider silk, cotton, other polypeptides and proteins, and any combinations thereof.

In yet another alternative embodiment, shape-shifting polymers can be used to fabricate stents constructed according to embodiments. Suitable shape-shifting polymers can be selected from the group consisting of polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof. For addition disclosure on bio-degradable shape-shifting polymers, see U.S. Pat. Nos. 6,160,084 and 6,284,862, the disclosures of each of which are incorporated by reference herein. For additional disclosure on shape memory polymers, see U.S. Pat. Nos. 6,388,043 and 6,720,402, the disclosures of each of which are incorporated by reference herein. Further the transition temperature can be set such that the stent can be in a collapsed condition at a normal body temperature. However, with the application of heat during stent placement and delivery, such as via a hot balloon catheter or a hot liquid (e.g., saline) perfusion system, the stent can expand to assume its final diameter in the body lumen. When a thermal memory material is used, it can provide a crush-recoverable structure.

Further still, stents can be formed from biocompatible polymers that are biostable (e.g., non-degrading and non-erodible). Examples of suitable non-degrading materials include, but are not limited to, polyurethane, Delrin, high density polyethylene, polypropylene, and poly(dimethyl siloxane).

In some embodiments, the layers can comprise or contain any example of thermoplastics, such as the following, among others: fluorinated ethylene-propylene, poly(2-hydroxyethyl methacrylate) (aka pHEMA), poly(ethylene terephthalate) fiber (aka Dacron®) or film (Mylar®), poly(methyl methacrylate) (aka PMMA), Poly(tetraflouroethylene) (aka PTFE and ePTFE and Gore-Tex®), poly(vinyl chloride), polyacrylates and polyacrylonitrile (PAN), polyamides (aka Nylon), polycarbonates and polycarbonate urethanes, polyethylene and poly(ethylene-co-vinyl acetate), polypropylene, polystyrene, polysulphone, polyurethane and polyetherurethane elastomers such as Pellethane® and Estane®, Silicone rubbers, Siloxane, polydimethylsiloxane (aka PDMS), Silastic®, Siliconized Polyurethane.

Finally, the polymer(s) utilized in embodiments of the stent can be fabricated according to any variety of processes, such as those discussed in U.S. Patent Application Nos. 60/852,471 and 60/852,513, and U.S. Pat. Nos. 5,194,570, 5,242,997, 6,359,102, 6,620,356, and 6,916,868, the disclosures of each of which are incorporated by reference herein.

Methods of Manufacturing and Assembling Polymeric Stents

Where plastic and/or degradable materials are used, the elements can be made using laser ablation with a screen, stencil or mask; solvent casting; forming by stamping, embossing, compression molding, centripetal spin casting and molding; extrusion and cutting, three-dimensional rapid prototyping using solid free-form fabrication technology, stereolithography, selective laser sintering, or the like; etching techniques comprising plasma etching; textile manufacturing methods comprising felting, knitting, or weaving; molding techniques comprising fused deposition modeling, injection molding, room temperature vulcanized molding, or silicone rubber molding; casting techniques comprising casting with solvents, direct shell production casting, investment casting, pressure die casting, resin injection, resin processing electroforming, or injection molding or reaction injection molding. Certain preferred embodiments with the disclosed polymers can be shaped into stents via combinations of two or more thereof, and the like.

Such processes can further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. For additional information, see U.S. patent application Ser. No. 10/655,338, the disclosure of which is incorporated by reference herein.

Stents of the preferred embodiment can be manufactured with elements prepared in full stent lengths or in partial lengths of which two or more are then connected or attached. If using partial lengths, two or more can be connected or attached to comprise a full length stent. In this arrangement the parts can be assembled to give rise to a central opening. The assembled full or partial length parts and/or modules can be assembled by inter-weaving them in various states, from a collapsed state, to a partially expanded state, to an expanded state.

Further, elements can be connected or attached by solvent or thermal bonding, or by mechanical attachment. If bonding, preferred methods of bonding comprise the use of ultrasonic radiofrequency or other thermal methods, and by solvents or adhesives or ultraviolet curing processes or photoreactive processes. The elements can be rolled by thermal forming, cold forming, solvent weakening forming and evaporation, or by preforming parts before linking.

Another method of manufacture allows for assembly of the stent components that have been cut out and assembled into flat series of radial elements. The linkage elements, flexible portions, etc. between longitudinally adjacent series of radial elements can be connected (e.g., by welding, inter-weaving frame elements, etc.), and the flat sheets of material can be rolled to form a tubular member. Coupling arms from floating coupling elements and end portions can be joined (e.g., by welding) to maintain the tubular shape. In embodiments that do not include coupling elements, the end portions of the top and bottom radial elements in a series can be joined. Alternatively, where sliding is desired throughout the entire circumference, a sliding and locking articulation can be made between the end portion of the top radial element and the rib(s)/rails of the bottom radial element (e.g., by tack-welding, heat-staking or snap-together). Similarly, a corresponding articulation can be made between the end portion of the bottom radial element and the rib(s)/rails of the top radial element.

Rolling of the flat series of module(s) to form a tubular member can be accomplished by any means known in the art, including rolling between two plates, which can be each padded on the side in contact with the stent elements. One plate can be held immobile and the other can move laterally with respect to the other. Thus, the stent elements sandwiched between the plates can be rolled about a mandrel by the movement of the plates relative to one another. Alternatively, 3-way spindle methods known in the art can also be used to roll the tubular member. Other rolling methods that can be used in accordance with certain embodiments include those used for "jelly-roll" designs, as disclosed for example, in U.S. Pat. Nos. 5,421,955, 5,441,515, 5,618,299, 5,443,500, 5,649,977, 5,643,314 and 5,735,872, the disclosures of each of which are incorporated herein in their entireties by reference thereto.

The construction of the slide-and-lock stents in these fashions can provide a great deal of benefit over the prior art. The construction of the locking mechanism can be largely material-independent. This allows the structure of the stent to comprise high strength materials, not possible with designs that require deformation of the material to complete the locking mechanism. The incorporation of these materials will allow the thickness required of the material to decrease, while retaining the strength characteristics of thicker stents. In preferred embodiments, the frequency of catches, stops or teeth present on selected circumferential elements can prevent unnecessary recoil of the stent subsequent to expansion.

Radiopacity

Traditional methods for adding radiopacity to a medical product include the use of metal bands, inserts and/or markers, electrochemical deposition (i.e., electroplating), or coatings. The addition of radiopacifiers (i.e., radiopaque materials) to facilitate tracking and positioning of the stent could be accommodated by adding such an element in any fabrication method, by absorbing into or spraying onto the surface of part or all of the device. The degree of radiopacity contrast can be altered by element content.

For plastics and coatings, radiopacity can be imparted by use of monomers or polymers comprising iodine or other radiopaque elements, i.e., inherently radiopaque materials. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, a halogen such as iodine and/or bromine can be employed for its radiopacity and antimicrobial properties.

Multi-Material Vascular Prosthesis

In still other alternative embodiments, various materials (e.g., metals, polymers, ceramics, and therapeutic agents) can be used to fabricate stent embodiments. The embodiments can comprise: 1) differentially layered materials (through stacking in the vertical or radial axis) to create a stack of materials (materials can be stacked in any configuration, e.g., parallel, staggered, etc.); 2) spatially localized materials which can vary along the long axis and/or thickness of the stent body; 3) materials that are mixed or fused to create a composite stent body (e.g., whereby a therapeutic agent(s) is within the stent body with a polymer); 4) embodiments whereby a material can be laminated (or coated) on the surface of the stent body (see Stent Surface Coatings with Functional Properties as well as see Therapeutic Agents Delivered by Stents); and, 5) stents comprised of 2 or more parts where at least one part can be materially distinct from a second part, or any combination thereof.

The fashioning of a slide-and-lock multi-material stent can have between two or more materials. Thickness of each material can vary relative to other materials. This approach as needed or desired allows an overall structural member to be built with each material having one or more functions contributing towards enabling prosthesis function which can include, but is not limited to: 1) enabling mechanical properties for stent performance as defined by ultimate tensile strength, yield strength, Young's modulus, elongation at yield, elongation at break, and Poisson's ratio; 2) enabling the thickness of the substrate, geometrical shape (e.g., bifurcated, variable surface coverage); 3) enabling chemical properties of the material that bear relevance to the materials performance and physical state such as rate of degradation and resorption (which can impact therapeutic delivery), glass transition temperature, melting temperature, molecular weight; 4) enabling radiopacity or other forms of visibility and detection; 5) enabling radiation emission; 6) enabling delivery of a therapeutic agent (see Therapeutic Agents Delivered by Stents); and 7) enabling stent retention and/or other functional properties (see Stent Surface Coatings with Functional Properties).

In some embodiments, the materials can comprise load-bearing properties, elastomeric properties, mechanical strength that can be specific to a direction or orientation e.g., parallel to another material and/or to the long axis of the stent, or perpendicular or uniform strength to another material and/or stent. The materials can comprise stiffeners, such as the following, boron or carbon fibers, pyrolytic carbon. Further, stents can be comprised of at least one re-enforcement such a fibers, nanoparticles or the like.

In another preferred mode of some embodiments, the stent can be made, at least in part, from a polymeric material, which can be degradable. The motivation for using a degradable stent can be that the mechanical support of a stent can only be necessary for several weeks. In some embodiments, bioresorbable materials with varying rates of resorption can be employed. For additional information, see U.S. patent application Ser. No. 10/952,202 and 60/601,526, the disclosures of each of which are incorporated by reference herein. Degradable polymeric stent materials can be particularly useful if it also controls restenosis and thrombosis by delivering pharmacologic agents. Degradable materials can be well suited for therapeutic delivery (see Therapeutic Agents Delivered by Stents).

In some embodiments, the materials can comprise or contain any class of degradable polymer as previously defined. Along with variation in the time of degradation and/or resorption the degradable polymer can have other qualities that are desirable. For example, in some embodiments the materials can comprise or contain any example of natural polymers (biopolymers) and/or those that degrade by hydrolytic and/or enzymatic action. In some embodiments, the material can comprise or contain any example of hydrogels that can or cannot be thermally reversible hydrogels, or any example of a light or energy curable material, or magnetically stimulateable (responding) material. Each of these responses can provide for a specific functionality.

In some embodiments, the materials can comprise or be made from or with constituents which can have some radiopaque material alternatively, a clinically visible material which can be visible by x-ray, fluoroscopy, ultrasound, MRI, or Imatron Electron Beam Tomography (EBT).

In some embodiments, one or more of the materials can emit predetermined or prescribed levels of therapeutic radiation. In one embodiment, the material can be charged with beta radiation. In another embodiment, the material can be charged with Gamma radiation. In yet another embodiment, the material can be charged with a combination of both Beta and Gamma radiation. Stent radioisotopes that can be used include, but are not limited to, 103Pd and 32P (phosphorus-32) and two neutron-activated examples, 65Cu and 87Rb2O, (90)Sr, tungsten-188 (188).

In some embodiments, one or more of the materials can comprise or contain a therapeutic agent. The therapeutic agents can have unique, delivery kinetics, mode of action, dose, half-life, purpose, et cetera. In some embodiments, one or more of the materials comprise an agent which provides a mode and site of action for therapy for example by a mode of action in the extracellular space, cell membrane, cytoplasm, nucleus and/or other intracellular organelle. Additionally an agent that serves as a chemoattractant for specific cell types to influence tissue formation and cellular responses for example host-biomaterial interactions, including anti-cancer effects. In some embodiments, one or more of the materials deliver cells in any form or state of development or origin. These could for example be encapsulated in a degradable microsphere, or mixed directly with polymer, or hydrogel and serve as vehicle for pharmaceutical delivery. Living cells could be used to continuously deliver pharmaceutical type molecules, for instance, cytokines and growth factors. Nonliving cells can serve as a limited release system. For additional concepts of therapeutic delivery, see the section entitled: Therapeutic Agents Delivered by Stents.

Therapeutic Agents Delivered by Stents

In another preferred variation, the stent further can comprise an amount of a therapeutic agent (as previously defined for a pharmaceutical agent and/or a biologic agent) sufficient to exert a selected therapeutic effect. The material of at least a portion of the stent itself can comprise at least one therapeutic agent, or at least one therapeutic agent can be added to the stent in a subsequent forming process or step. In some preferred embodiments of the stent (e.g., polymer stents and multi-material stents), the therapeutic agent can be contained within the stent as the agent is blended with the polymer or admixed by other means known to those skilled in the art.

For example, one or more therapeutic agents can be delivered through a multi-material vascular prosthesis. In some embodiments, the entire stent can be formed from materials comprising one or more therapeutic agents. In other embodiments, portions of the stent, such as individual components thereof, can comprise materials comprising one or more therapeutic agents. In such embodiments, it is contemplated that the therapeutic agent(s) can be released as the stent material degrades.

For example, the therapeutic agent can be embedded or impregnated into the film by means of a combination of solvent casting and thermal pressing. In such a method, the film can be formed from a mixture of the polymer and the therapeutic agent (20% solids polymer, for example poly (90% DTE-co-10% DT carbonate), which can be made with 1% rapamycin in dichloromethane). Once this mixture is prepared, the film can be cast using a doctor blade. Alternatively, the film can be formed by using a mechanical reverse roll coater or other solvent-based film caster. Once the film is cast, the solvent can be evaporated off using a vacuum oven, e.g., for a period of time and at a temperature suitable for the polymer and drug, such as at 40° C. for at least 20 hours. Once the film is dried, it can be thermally pressed, e.g., at a temperature of 100° C. between two heated platens of a hydraulic press. This allows the potency of the drug to be retained.

In addition, the therapeutic agent can be embedded or impregnated into the film using only a solvent or by spin casting. Once a therapeutic agent is selected, one needs to determine if the solvent is compatible with the agent and the polymer chosen. The objective is to prepare a suitable sprayable suspension. Additionally, the stability of the drug can be measured such that the therapeutic agent can remain active while in the coating as well under physiological conditions once released from the film. This can be determined by those skilled in the art who conduct standard in vitro elution studies (see Dhanikula et al., *Development and Characterization of Biodegradable Chitosan Films for Local Delivery of Paclitaxel*, The AAPS Journal, 6 (3) Article 27 (2004), http://www.aapsj.org/view.asp?art=aapsj060327; and Kothwala et al., *Paclitaxel Drug Delivery from Cardiovascular Stent*, Trends in Biomaterials & Artificial Organs, Vol. 19(2), 88-92 (2006), http://medind.nic.in/taa/t06/i1/taat06i1p88.pdf) of agent embedded films and through the use of analytical methods such as HPLC methods (see Dhanikula et al., *Development and Characterization of Biodegradable Chitosan Films for Local Delivery of Paclitaxel*; and Kothwala et al., *Paclitaxel Drug Delivery from Cardiovascular Stent*) to detect the purity of the drug.

In other embodiments, at least one therapeutic agent can be added to the stent and/or its components after the formation of the stent and/or its components. For example, at least one therapeutic agent can be added to individual stent components, through a coating process or otherwise. The addition of at least one therapeutic agent can occur before or after cutting or lasing of the stent components. In another example, at least one therapeutic agent can also be added to at least a portion of the stent after partial or full assembly thereof, through a coating process or otherwise. In some embodiments of the stent, the therapeutic agent can be delivered from a polymer coating on the stent surface. In other preferred embodiments of the stent, a therapeutic agent can be localized in or around a specific structural aspect of the device.

For example, the therapeutic agent can be delivered from a polymer coating on the stent surface. Thus, the stent can be made by applying the therapeutic agent to a stent component before the stent is assembled or formed. In this regard, the stent component can be created from a polymer sheet, such as a flat polymer film. Thus, at least one stent component can be separated from a remainder or excess portion of the film either before or after the therapeutic agent has been applied to the stent component and/or film. After the therapeutic agent is applied and the stent component is separated from the film, the stent component can be assembled (and in some embodiments, with other stent components) to form a stent therefrom.

In an exemplary embodiment, the stent can be prepared with the following preparation method. The stent can be initially prepared by creating a pattern of a stent component on a flat polymer film. The creation of the pattern on the film can occur before or after application of a therapeutic agent thereto, as discussed below. The pattern of the stent component can be created on the film such that the stent component can be detached from the film when desired. In some embodiments, the pattern can be created using a laser to lase the pattern onto the film. Additionally, the lased pattern can be of any given stent component design, such as that used in a slide and lock stent design. After the pattern is created on the film, the entire film can be cleaned. For example, if the therapeutic agent has not yet been applied to the film, the entire lased film can be immersed into a cleaning solution that is compatible with the specific type of polymer from which the film is made. The cleaned film can then be dried, for example, by being blown and oven dried.

A coating formulation can be prepared by dissolving or dispersing the polymer and the therapeutic agent(s) of choice and solvent(s) or other compatible excipient(s) using a calculated amount of each component to achieve the desired concentration. The coating formulation can then be applied to the lased polymer film using one or more coating methods. For example, the film may be coated by means of spraying, dipping, or other coating methods. Additionally cross-linking reagents may also be used to prepare a coating.

In a spraying coating method, the lased polymer films can be coated with the coating formulation by first mounting the cleaned dried films into a spray apparatus. The coating formulation can then be sprayed onto the film, and the film can be rotated 180 degrees such that the other side can be coated if desired. This method can allow for coating of one or both sides of the stent component(s). This method can also allow one to apply different therapeutic agents per side of the lased film and/or stent component and to selectively coat regions thereof. The method can further allow one to coat multiple drugs per film and/or stent component. Alternative coating methods can allow for other similar benefits.

For example, a therapeutic agent can be coated onto a film or stent component as in the following illustration. First, the therapeutic agent in this example is a Polymer-Paclitaxel Formulation, such as a 0.5% [25% Paclitaxel/75% Poly (86.75% I2DTE-co-10% I2DT-co-3.25% PEG2000 carbonate)] in tetrahydrofuran (THF), which can be prepared using an analytical balance. In order to do so, one must first weigh 0.0150 g of Paclitaxel into a tared vial. Then weigh 0.0450 g of polymer into another vial. Next, weigh 11.940 g of THF into each vial. Shake the vials on a laboratory shaker, such as a Roto-genie, for at least one hour. In this example, coating can be achieved using a spray gun apparatus, such as an air brush (see Westedt, U., *Biodegradable Paclitaxel-loaded Nanoparticles and Stent Coatings as Local Delivery Systems for the Prevention of Restenosis—Dissertation*, Marburg/Lahn (2004), http://deposit.ddb.de/cgi-bin/dokserv?idn= 972868100&dokvar=d1&dokext=pdf&filename= 972868100.pdf; and Berger, H. L. *Using Ultrasonic Spray Nozzles to Coat Drug-Eluting Stents*, Medical Device Technology (2006), http://www.devicelink.com/mdt/archive/06/ 11/004.html). Typically, the spray gun apparatus should first be cleaned with THF. In order to do so, a syringe can be filled with at least 10 ml of THF. The syringe can then be attached to a spray line attached to the spray gun. Gradually, the 10 ml of THF can be pushed from the syringe into the spray gun without N2 pressure. This can be repeated as necessary to ensure that the line is washed clean. The syringe pump can then be set up with the syringe containing the Polymer-Paclitaxel Formulation.

Next, a film, which can be either lased or unlased, can be placed into a hooded environment and mounted or clipped into a holder. If necessary, the surfaces of the film can be cleaned of lint and dust using a pure air or gas source or equivalent. For consistent coating quality, the film can be programmed to move at a set rate (distance and speed) relative to a spray stream by integrating the film holder apparatus with a motion control system. Manual coating without the motion control can also be used to achieve a coating. The spray gun can also be set to direct the spray to only a given location to control coating distribution.

In some embodiments, to coat both sides of the film uniformly, the spray cycle can start with the spray hitting at the bottom corner of the film, and the motion control should move the film incrementally as it traverses back and forth in front of the spray nozzle. The system can then move the film back to the start position so the spray is directed at the bottom. The film holder can be turned 180 degrees and the cycle can be repeated to coat the second side. After coating, the film holder can be removed with the film and the film can be dried in a vacuum oven at a temperature suitable for the drug and polymer, e.g., 25°±5° C. for at least 20 hours.

Other methods and teachings related to impregnation or coating processes are found in the following references, the entirety of each of which is hereby incorporated by reference herein: Westedt, U., *Biodegradable Paclitaxel-loaded Nanoparticles and Stent Coatings as Local Delivery Systems for the Prevention of Restenosis—Dissertation*, Marburg/Lahn (2004), http://deposit.ddb.de/cgi-bin/dokserv?idn= 972868100&dokvar=d1&dokext=pdf&filename= 972868100.pdf; Berger, H. L. *Using Ultrasonic Spray Nozzles to Coat Drug-Eluting Stents*, Medical Device Technology (2006), http://www.devicelink.com/mdt/archive/06/ 11/004.html; Dhanikula et al., *Development and Characterization of Biodegradable Chitosan Films for Local Delivery of Paclitaxel*, The AAPS Journal, 6 (3) Article 27 (2004), http://www.aapsj.org/view.asp?art=aapsj060327; and Kothwala et al., *Paclitaxel Drug Delivery from Cardiovascular Stent*, Trends in Biomaterials & Artificial Organs, Vol. 19(2), 88-92 (2006), http://medind.nic.in/taa/t06/i1/ taat06i1p88.pdf.

After the film is coated using a given coating method, the film can be given time to dry. Once dried, the lased, coated stent component(s) can be separated from the remainder of the film. Care should be taken to not disturb the surfaces of the coated stent component(s) when being detached from the film and assembled or knitted together to form a three-dimensional cylindrical stent.

In another preferred variation the therapeutic agent can be delivered by means of a non-polymer coating. In other preferred embodiments of the stent, the therapeutic agent can be delivered from at least one region or one surface of the stent. The therapeutic agent can be chemically bonded to the polymer or carrier used for delivery of the therapeutic from at least one portion of the stent and/or the therapeutic can be chemically bonded to the polymer that can comprise at least one portion of the stent body. In some embodiments, a polymer can be used as a component of the coating formulation. Accordingly, the coating can essentially bond directly to a clean lased film and/or stent component, which can also be comprised of a polymer. Such an embodiment of the method can provide for a seamless interface between the coating and the lased film and/or stent component. Further, in another embodiment, more than one therapeutic agent can be delivered.

The amount of the therapeutic agent can be preferably sufficient to inhibit restenosis or thrombosis or to affect some other state of the stented tissue, for instance, heal a vulnerable plaque, and/or prevent rupture or stimulate endothelialization or limit other cell types from proliferating and from producing and depositing extracellular matrix molecules. The agent(s) can be selected from the group consisting of antiproliferative agents, anti-inflammatory, anti-matrix metalloproteinase, and lipid lowering, cholesterol modifying, antithrombotic and antiplatelet agents, in accordance with preferred embodiments. For vascular stent applications, some of these preferred anti-proliferative agents that improve vascular patency include without limitation paclitaxel, Rapamycin, ABT-578, Biolimus A9, everolimus, dexamethasone, nitric oxide modulating molecules for endothelial function, tacrolimus, estradiol, mycophenolic acid, C6-ceramide, actinomycin-D and epothilones, and derivatives and analogs of each.

Some of these preferred agents act as an antiplatelet agent, antithrombin agent, compounds to address other pathologic events and/or vascular diseases. Various therapeutic agents can be classified in terms of their sites of action in the host: agents that exert their actions extracellularly or at specific membrane receptor sites, those that act on the plasma membrane, within the cytoplasm, and/or the nucleus.

In addition to the aforementioned, therapeutic agents can include other pharmaceutical and/or biologic agents intended for purposes of treating body lumens other than arteries and/or veins). Therapeutic agents can be specific for treating nonvascular body lumens such as digestive lumens (e.g., gastrointestinal, duodenum and esophagus, biliary ducts), respiratory lumens (e.g., tracheal and bronchial), and urinary lumens (e.g., urethra). Additionally such embodiments can be useful in lumens of other body systems such as the reproductive, endocrine, hematopoietic and/or the integumentary, musculoskeletal/orthopedic and nervous systems (including auditory and ophthalmic applications); and finally, stent embodiments with therapeutic agents can be useful for expanding an obstructed lumen and for inducing an obstruction (e.g., as in the case of aneurysms).

Therapeutic release can occur by controlled release mechanisms, diffusion, interaction with another agent(s) delivered by intravenous injection, aerosolization, or orally. Release can also occur by application of a magnetic field, an electrical field, or use of ultrasound.

Stent Surface Coatings with Functional Properties

In addition to stents that can deliver a therapeutic agent, for instance delivery of a biological polymer on the stent such as a repellant phosphorylcholine, the stent can be coated with other bioresorbable polymers predetermined to promote biological responses in the body lumen desired for certain clinical effectiveness. Further the coating can be used to mask (temporarily or permanently) the surface properties of the polymer used to comprise the stent embodiment. The coating can be selected from the broad class of any biocompatible bioresorbable polymer which can include any one or combination of halogenated and/or non-halogenated which can or cannot comprise any poly(alkylene glycol). These polymers can include compositional variations including homopolymers and heteropolymers, stereoisomers and/or a blend of such polymers. These polymers can include for example, but are not limited to, polycarbonates, polyarylates, poly(ester amides), poly(amide carbonates), trimethylene carbonate, polycaprolactone, polydioxane, polyhydroxybutyrate, polyhydroxyvalerate, polyglycolide, polylactides and stereoisomers and copolymers thereof, such as glycolide/lactide copolymers. In a preferred embodiment, the stent can be coated with a polymer that exhibits a negative charge that repels the negatively charged red blood cells' outer membranes thereby reducing the risk of clot formation. In another preferred embodiment, the stent can be coated with a polymer that exhibits an affinity for cells, (e.g., endothelial cells) to promote healing. In yet another preferred embodiment, the stent can be coated with a polymer that repels the attachment and/or proliferation of specific cells, for instance arterial fibroblasts and/or smooth muscle cells in order to lessen restenosis and/or inflammatory cells such as macrophages.

Described above are embodiments that can be modified with a coating to achieve functional properties that support biological responses. Such coatings or compositions of material with a therapeutic agent can be formed on stents or applied in the process of making a stent body via techniques such as dipping, spray coating, cross-linking combinations thereof, and the like, as mentioned and described above. Such coatings or compositions of material can also serve purpose other than delivering a therapeutic, such as to enhance stent retention on a balloon when the coating is placed intraluminally on the stent body and/or placed over the entire device after the stent is mounted on the balloon system to keep the stent in a collapsed formation. Other purposes can be envisioned by those skilled in the art when using any polymer material.

In one aspect of certain embodiments, a stent would have a coating applied that can alter the physical characteristics of the stent, such as to provide specific mechanical properties to the stent. The properties can include inter alia thickness, tensile strength, glass transition temperature, and surface finish. The coating can be preferably applied prior to final crimping or application of the stent to the catheter. The stent can then be applied to the catheter and the system can have either heat or pressure or both applied in a compressive manner. In the process, the coating can form frangible bonds with both the catheter and the other stent surfaces. The bonds would enable a reliable method of creating stent retention and of holding the stent crossing profile over time. The bonds would break upon the balloon deployment pressures. The coating would be a lower Tg than the substrate to ensure no changes in the substrate.

Stent Deployment

First, a catheter is provided wherein an expandable member, preferably an inflatable balloon, such as an angioplasty balloon, is provided along a distal end portion. One example of a balloon catheter for use with a stent is described in U.S. Pat. No. 4,733,665 to Palmaz, the disclosure of which is incorporated by reference herein. A stent on a catheter can be commonly collectively referred to as a stent system. Catheters include but are not limited to over-the-wire catheters, coaxial rapid-exchange designs and the Medtronic Zipper Technology that is a new delivery platform. Such catheters can include for instance those described in Bonzel U.S. Pat. Nos. 4,762,129 and 5,232,445 and by Yock U.S. Pat. Nos. 4,748,982, 5,496,346, 5,626,600, 5,040,548, 5,061,273, 5,350,395, 5,451,233 and 5,749,888. Additionally, catheters can include for instance those as described in U.S. Pat. Nos. 4,762,129, 5,092,877, 5,108,416, 5,197,978, 5,232,445, 5,300,085, 5,445,646, 5,496,275, 5,545,135, 5,545,138, 5,549,556, 5,755,708, 5,769,868, 5,800,393, 5,836,965, 5,989,280, 6,019,785, 6,036,715, 5,242,399, 5,158,548, and 6,007,545. The disclosures of each of the above-cited patents are incorporated herein in their entirety by reference thereto.

Catheters can be specialized with highly compliant polymers and for various purposes such as to produce an ultrasound effect, electric field, magnetic field, light and/or temperature effect. Heating catheters can include for example those described in U.S. Pat. Nos. 5,151,100, 5,230,349, 6,447,508, and 6,562,021 as well as WO9014046A1. Infrared light emitting catheters can include for example those described in U.S. Pat. Nos. 5,910,816 and 5,423,321. The disclosures of each of the above-cited patents and patent publications are incorporated herein in their entirety by reference thereto.

An expandable member, such as an inflatable balloon, can be preferably used to deploy the stent at the treatment site. As the balloon is expanded, the radial force of the balloon overcomes the initial resistance of the constraining mechanism, thereby allowing the stent to expand.

The stent of embodiments described herein can be adapted for deployment using conventional methods known in the art and employing percutaneous transluminal catheter devices.

This can include deployment in a body lumen by means of a balloon expandable design whereby expansion can be driven by the balloon expanding. Alternatively, the stent can be mounted onto a catheter that holds the stent as it is delivered through the body lumen and then releases the stent and allows it to self-expand into contact with the body lumen. The restraining means can comprise a removable/retractable sheath, a sheath that remains with the stent, and/or a mechanical aspect of the stent design.

The use of a sheath can be beneficial for several reasons. The sheath can be used to control delivery and deployment of the stent. For example, the sheath can be used to reduce and/or eliminate "negative aspects" of certain configurations of the stent, such as certain "slide-and-lock" designs; however, the sheath can also be used to make other designs possible.

The invention is composed of a polymeric sheath, most likely made out of a biodegradable material, which has sufficient elasticity to stretch during deployment of the stent and not break. The polymer also may include radiopaque, biodegradable polymers. The sheath is tubular in nature, and may include cutouts patterns to provide lower deployment pressures, increase flexibility and allow access to side branches of the artery. Ideally the sheath is very thin, such as less than 0.002", and ideality 0.0005" thick. The material need not have a high yield strength, but should have an elongation at break of greater than 150%, and possibly as much as 300%.

The sheath can be made from a variety of materials, such as polymers, natural materials, etc., which can include biodegradable materials. Further, the polymer can be radiopaque, biocompatible, and/or biodegradable, as discussed herein. In some embodiments, the sheath can be made from a resorbable material, and the sheath and stent can degrade together, thus leaving a healed, unencumbered vessel. The sheath material can be selected such that during stent expansion, the sheath can deform and expand plastically with the stent. In some embodiments, the sheath can have sufficient elasticity to stretch during deployment of the stent without breaking. Although high yield strength may not be required, the material preferably provides the sheath with an elongation at break of greater than 150%, and possibly as much as 300%.

Further, the sheath can be very thin, such as less than about 0.002 inches thick, but can preferably be about 0.0005 inches thick; other thicknesses can also be used in accordance with the teachings herein. Thus, the sheath can be beneficially used to eliminate or reduce negative aspects of certain stent designs, such as may be encountered during stent deployment, as well as to make other stent designs possible.

Figure 29B:
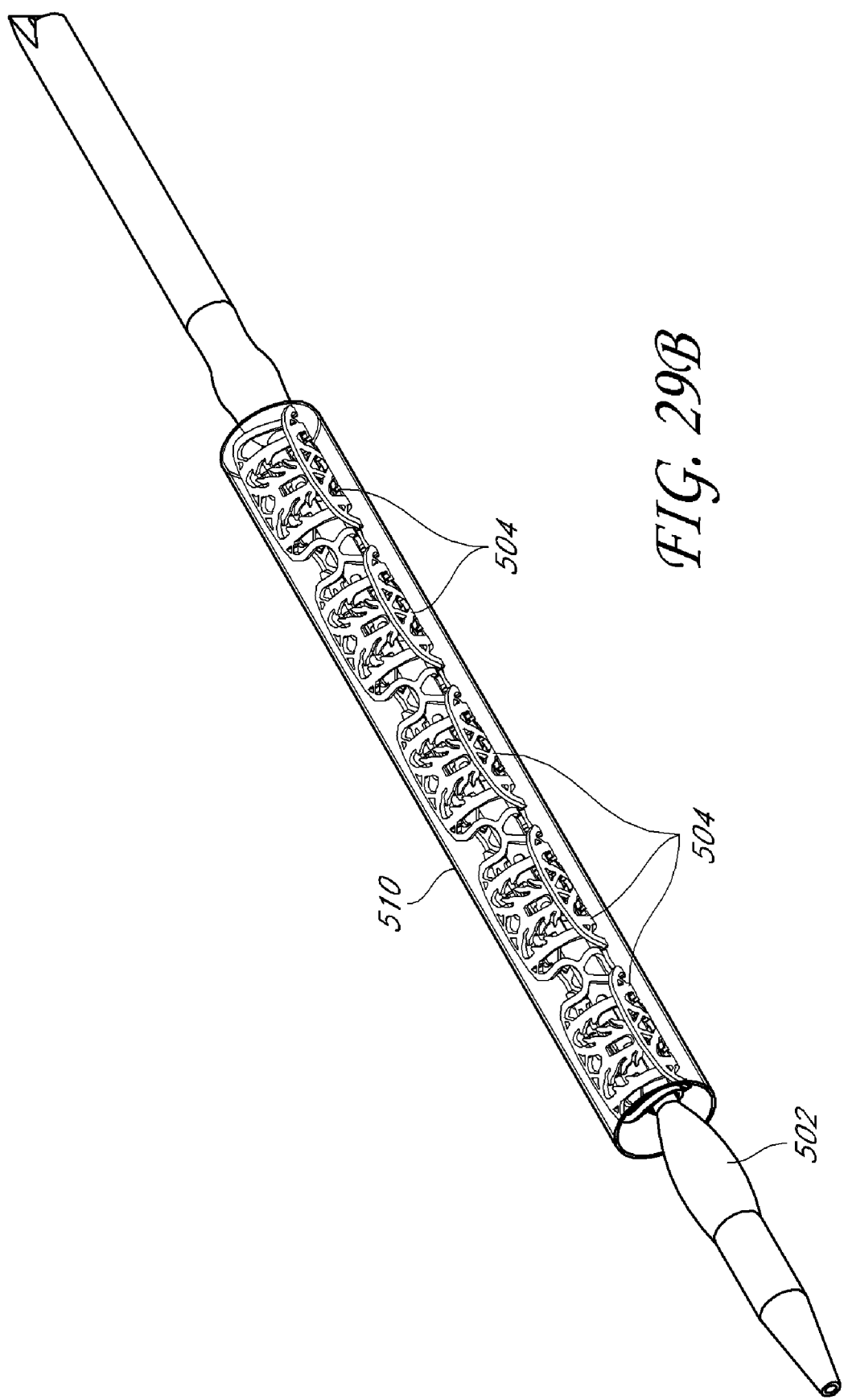
FIG. 29B is a perspective view of the stent and balloon catheter shown in FIG. 29A with a sheath disposed on the stent, in accordance with another embodiment.

In a first embodiment, illustrated in FIGS. 29A-B, the sheath can be used to control and protect "loose geometry" of the stent. In FIG. 29A, a stent 500 is placed onto a balloon catheter 502 in preparation for insertion and deployment of the stent 500 in a vessel. As shown, the stent 500 can include various components 504 that can slide relative to each other during expansion of the stent 500. However, in its unexpanded state, these components 504 can at least partially overlap each other and can protrude from the stent 500. The protruding geometry of the components 504 of the stent 500 are often referred to as "tails." The tails in such embodiments of the stent 500 are typically unconstrained when the stent is mounted on the balloon (shown in FIG. 29A). In such embodiments, these features tend to create an undulating surface which has the potential to snag when the stent 500 is passing within a vessel or traversing a constriction of the vessel. If the stent 500 were to snag, the geometry and components 504 of the stent 500 could possibly become bent or damaged, which might result in deployment problems or reduced stent performance. Therefore, a polymeric sheath 510 can be utilized to provide a thin protective covering to the geometry of the stent 500. Thus, the sheath 510 can smooth over the undulations and prevent stent geometry from being displaced.

The sheath can also be formed to include structural patterns. Such patterns can be formed by altering the characteristics of the sheath, such as by removing material from, providing additional material for, or using different types of materials for a given portion of the sheath. For example, the sheath can include cutout patterns that can be used to provide lower deployment pressures, increase flexibility and allow access to side branches of the artery, as described in copending U.S. patent application Ser. Nos. 10/897,235 and 11/016,269, the disclosure of each of which is incorporated herein by reference.

Figure 30:
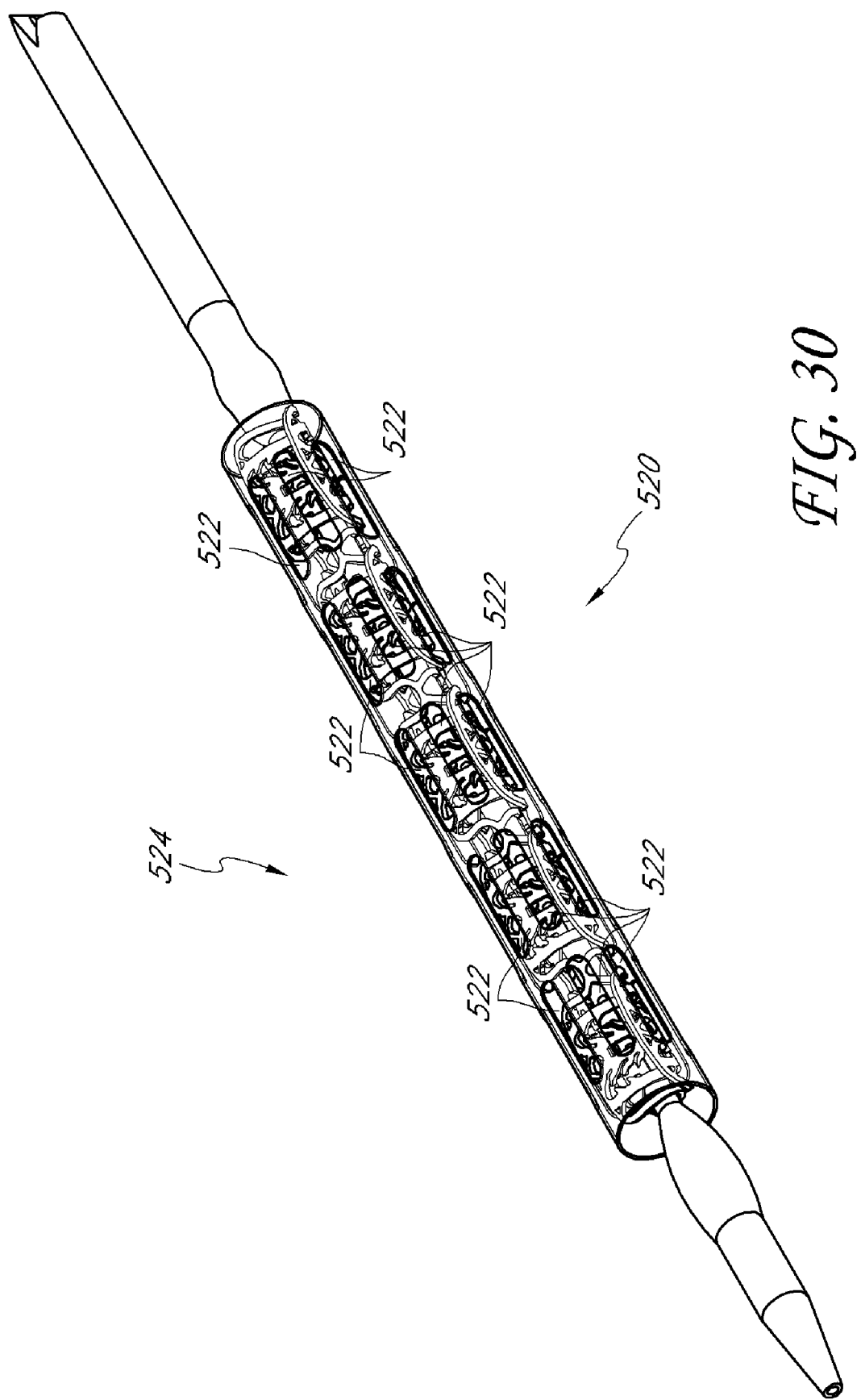
FIG. 30 is a perspective view of yet another embodiment of a sheath having a structural pattern and being disposed on another stent.

In some embodiments, such as that illustrated in FIG. 30, a sheath 520 can include a plurality of apertures 522 disposed in a radial pattern through the sheath 520. The apertures 522 can allow the sheath 520 to elongate, thus still providing a minimal surface coverage, and access to side branches. The illustrated pattern 524 shown in FIG. 30 is a representative pattern that can be varied as desired to include more or less apertures, to vary the size or shape of the apertures, to vary the axial and/or circumferential spacing of the apertures, etc. Further, many other patterns can be utilized, including, but not limited to ellipses, triangles, complicated patterns, non-uniform patterns, different module and spring areas, varying thicknesses, etc.

For example, the stent can be formed to include a solid wall region, and in such embodiments, the solid wall region can be formed to have an opening that allows fluid communication with a side branch vessel. Accordingly, the sheath utilized with such a stent can include a structural pattern that corresponds to the configuration of the solid wall region and openings of the stent. Such features and configurations can be used with sheaths that remain on the stent, and are not retracted. Further, the patterns can be lased into the sheath or formed by other means.

In addition, embodiments of the sheath can be configured to deform plastically along with the stent and balloon during deployment and expansion of the stent. During deployment of some embodiments, the patterns on the sheath can elongate, thus maintaining a minimal surface coverage and access to side branches. FIG. 30 is only a representative pattern, and many other patterns can be used to promote certain deformation modes, structural characteristics, and interactions between the sheath and the stent.

As described above, embodiments of the sheath can be configured to remain on the stent during expansion. Thus, once the stent is fully expanded, the sheath can be coincident with the vessel wall. In some embodiments, the sheath can be made from a resorbable material, and the sheath and stent can degrade together, thus leaving a healed. unencumbered vessel. In other embodiments, the sheath can be configured to fail or be removed during expansion of the stent. Thus, the sheath can also be made from non-resorbable materials, which can be selected to provide certain material properties for example, to facilitate deployment of the stent.

Some sheath embodiments can be useful in coronary arteries, carotid arteries, vascular aneurysms (when covered with a sheath), and peripheral arteries and veins (e.g., renal, iliac, femoral, popliteal, subclavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may or may not require a sheath covering the stent. Various other used and applications can be devised using the present disclosure.

Stent Surface Features with Functional Properties

In addition to the features and aspects of embodiments described above, other embodiments can be configured to include functional surface textures, surface finishes, and features. Such features can contribute to the strength and/or rigidity of the stent. Additionally, such features can tend to ensure that the placement of the stent is maintained.

Figure 31:
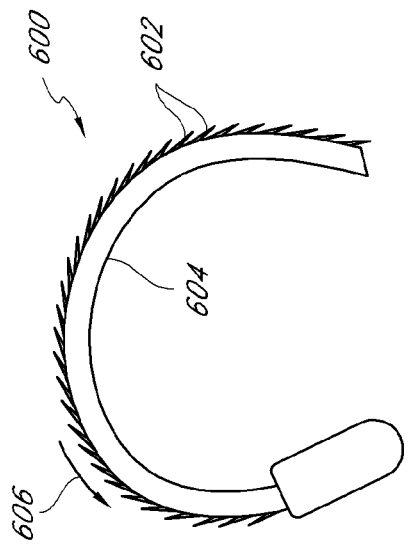
FIG. 31 is a side view of a linkage component of a stent having fish scales, according to an embodiment.
Figure 32B:
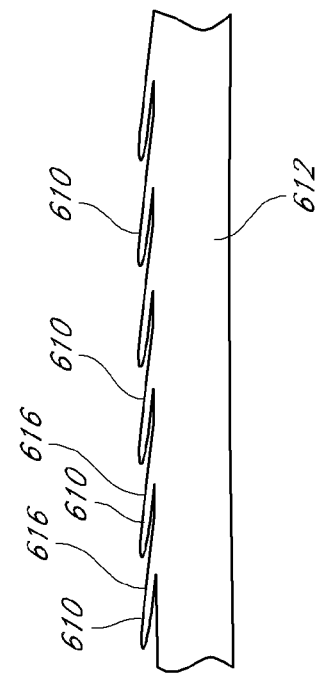
FIG. 32B is a side view of the stent component of FIG. 31 illustrating the fish scale pattern.

In accordance with such an embodiment, the stent can be formed to include scales on the surface thereof. FIGS. 31-32B illustrate embodiments of a scaled surface structure of a stent. The scales can extend from the surface of the tubular member or structural members of which the stent can be comprised. For example, the scales can be disposed on exterior portions of struts, structural elements and sections of the stent. The scales can be variously sized and shaped as known by one of skill in the art. The scales can be rigidly attached to the stent, such that the scales are non-elastically moveable relative to the stent. However, the scales can also be substantially flexible and move relative to the stent.

In FIG. 31, a linkage section 600 is shown having a plurality of scale-like features 602 extending from an interconnection member 604 of the linkage section 600. In some embodiments, the scales 602 can extend at a generally oblique angle relative to the interconnection member 604. Accordingly, during expansion of the stent, the interconnection member 604 can move in the direction of arrow 606 relative to an adjacent linkage section. As discussed herein, in some embodiments, the interconnection member 604 can be disposed through an engagement aperture of the adjacent linkage section. As such, the scales 602 can pass through the engagement aperture and be deflected downwardly towards the surface of interconnection member 604, allowing the interconnection member 604 to move in a direction of expansion 606.

However, as a given scale 602 exits the engagement aperture of the adjacent linkage section during expansion, the given scale 602 can rebound to its original angular orientation relative to the interconnection member 604. In this orientation, any collapsing movement in a direction reverse to arrow 606 will be opposed because the given scale 602 will not be able to pass back through the engagement aperture because it will catch and not be downwardly deflected so as to allow passage of the interconnection member 604 through the engagement aperture. Thus, while expansion is possible in one direction, the scales 602 can impede collapsing of the stent in the other direction. Accordingly, one-way movement of the interconnection member 604 can be accomplished using the scale 602 in embodiments disclosed herein.

In this regard, the scales 602 are preferable formed on an exterior surface of the interconnection member 604. Nevertheless, for purposes of allowing one-way movement of the interconnection members of a linkage section relative to an adjacent linkage section, the scales can be disposed on any of the surfaces of the interconnection member. For example, the scales can be disposed on side or interior surfaces thereof.

Furthermore, the scale 602 can also be useful to assist the stent in maintaining the position of the stent within a vessel or lumen. For example, in an embodiment wherein the scales 602 are formed on an exterior surface of the interconnection member, as shown in FIG. 31, the scales 602 can tend to engage the inner wall of the vessel or lumen in order to impede rotation of the stent within the vessel or lumen. As such, the engagement of the scale 602 with the sidewalls of the vessel or lumen can also tend to maintain the stability and rigidity of the stent within the vessel or lumen.

Figure 32A:
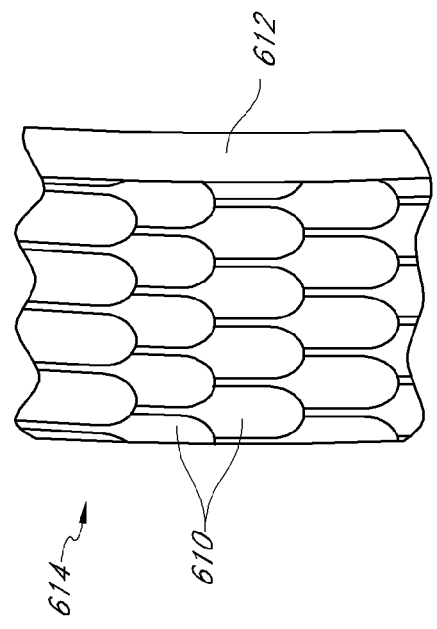
FIG. 32A is a perspective view of a portion of a stent component having a fish scale pattern, in accordance with an embodiment.

FIGS. 32A-B represent another embodiment of scales 610 that can be employed with an interconnection member 612 of a linkage section 614. In the perspective view of FIG. 32A, the scales 610 can be axially offset from each other. Accordingly, the scales 610 can provide greater surface coverage and provide enhanced engagement capabilities with the wall of the vessel or lumen. FIG. 32B is an enlarged side view of the embodiment shown in FIG. 32A. As illustrated therein, the scales 610 can be oriented at a small angle relative to an exterior surface 616 of the interconnection member 612. In at least one of the embodiments described herein, the scales can be oriented at an acute angle relative to an exterior surface of the stent. In some embodiments, the scale can be oriented at an angle between 10° to 30°.

As also shown in FIG. 32B, the distal end of the scales 610 can be tapered, and can be configured to have a non-blunted edge or tip. In contrast to sharpened tips or hooks, some embodiments can be configured such that the scales 610 are configured to prevent or minimize damage to the interior wall of the vessel. In this manner, the distal end of the scales 610 can allow the scale to removably engage an interior wall of a vessel to at least create friction between the scale 610 and the interior wall. Thus, the scales 610 can allow the stent to move in one direction, but engage the interior wall to inhibit movement of the stent in the opposite direction.

Accordingly, the cross-sectional profile of the stent can be reduced as well as the potential for catching or snagging portions of the stent and scales that may extend away from the interconnection member. Thus, the embodiment illustrated in FIGS. 32A-B can allow a smooth introduction and deployment of the stent while providing the one-way movement and antirotational features that can be achieved by using scales 610 in connection with the interconnection member 612.

In use, after the stent has been axially located within a vessel, the scales can become implanted into a wall thereof to increase friction between the stent and the vessel wall to prevent stent motion in one direction while enhancing it in the other. Such an embodiment can be used to ensure stent placement and/or increase the radial strength of the stent in one direction while reducing it in the opposite direction. Therefore, the scales can be oriented on the stent to restrict rotational and/or longitudinal movement of the stent.

For example, a coil stent with scales could deploy smoothly in one rotational direction and resist motion when the artery wall pushes back over time. In another example, a filter or valve with scaled struts could better resist forces created by filtered/clotted unidirectional blood flow without the use of sharp tips or hooks. Further, radially-oriented scales can also be used to prevent stent collapse from an expanded state.

It can be desirable to have the stent radially expand in a uniform manner. Alternatively, the expanded diameter can be variable and determined by the internal diameter and anatomy of the body passageway to be treated. Accordingly, uniform and variable expansion of the stent that is controlled during deployment is not likely to cause a rupture of the body passageway. Furthermore, the stent will resist recoil because the locking means resist movement of the mating elements. Thus, the expanded intraluminal stent will continue to exert radial pressure outward against the wall of the body passageway and will therefore, not migrate away from the desired location.

It is to be understood that any range of values disclosed, taught or suggested herein can comprise all values and subranges therebetween. For example, a range from 5 to 10 will comprise all numerical values between 5 and 10 and all subranges between 5 and 10.

From the foregoing description, it will be appreciated that a novel approach for expanding a lumen has been disclosed. While several components, techniques and aspects have been described with a certain degree of particularity, it is manifest that many changes can be made in the specific designs, constructions and methodology herein above described without departing from the spirit and scope of this disclosure.

The methods which are described and illustrated herein are not limited to the sequence of acts described, nor are they necessarily limited to the practice of all of the acts set forth. Other sequences of acts, or less than all of the acts, or simultaneous occurrence of the acts, can be utilized in practicing embodiments.

While a number of preferred embodiments and variations thereof have been described in detail, other modifications and methods of using and medical applications for the same will be apparent to those of skill in the art. Accordingly, it should be understood that various applications, modifications, materials, and substitutions can be made of equivalents without departing from the spirit of the inventions or the scope of the claims.

Various modifications and applications of the embodiments can occur to those who are skilled in the art, without departing from the true spirit or scope of the inventions. It should be understood that the present inventions are not limited to the embodiments set forth herein for purposes of exemplification, but is to be defined only by a fair reading of the claims, including the full range of equivalency to which each element thereof is entitled.

REFERENCES

Some of the references cited herein are listed below, the entirety of each one of which is hereby incorporated by reference herein:

Charles R, Sandirasegarane L, Yun J, Bourbon N, Wilson R, Rothstein R P, et al., *Ceramide-Coated Balloon Catheters Limit Neointimal Hyperplasia after Stretch Injury in Carotid Arteries*, Circulation Research 2000; 87(4): 282-288.

Coroneos E, Martinez M, McKenna S, Kester M., *Differential regulation of sphingomyelinase and ceramidase activities by growth factors and cytokines. Implications for cellular proliferation and differentiation*, J Biol. Chem. 1995; 270 (40): 23305-9.

Coroneos E, Wang Y, Panuska J R, Templeton D J, Kester M., *Sphingolipid metabolites differentially regulate extracellular signal-regulated kinase and stress-activated protein kinase cascades*, Biochem J. 1996; 316 (Pt 1): 13-7.

Jacobs L S, Kester M., *Sphingolipids as mediators of effects of platelet-derived growth factor in vascular smooth muscle cells*, Am. J. Physiology 1993; 265 (3 Pt 1): C740-7.

Tanguay J F, Zidar J P, Phillips H R, 3rd, Stack R S, *Current status of biodegradable stents*, Cardiol. Clin. 1994; 12(4): 699-713.

Nikol S, Huehns T Y, Hofling B., *Molecular biology and post-angioplasty restenosis*, Atherosclerosis 1996; 123 (1-2): 17-31.

BUDDY D. RATNER, ALLAN S. HOFFMAN, FREDERICK J. SCHOEN, AND JACK E. LEMONS, Biomaterials Science: An Introduction to Materials in Medicine (Elsevier Academic Press 2004).

What is claimed is:

1. An offset rail stent being expandable from an axially-radially nested unexpanded state to an expanded state, the stent comprising a tubular member having a longitudinal axis, the tubular member comprising:

a plurality of linkage strands extending in generally parallel directions along the longitudinal axis, each linkage strand having a plurality of frame elements being interconnected in an end-to-end fashion via at least one interconnection element, each frame element comprising at least one rail member having a free end separate from the free ends of rail members on other frame members, each rail member extending from the frame element in a circumferential direction, each frame element further comprising at least one engagement aperture, at least one rail member extending through an engagement aperture of an adjacent linkage strand, wherein each engagement aperture and each rail member are sized such that the at least one rail member can freely pass through a respective engagement aperture; and a plurality of coupling elements each attached to a free end of a respective rail member extending through the engagement aperture;

a plurality of engagement mechanisms, each comprising at least one of the coupling elements engaged with at least one of the engagement apertures providing one-way movement of the coupling element engaged with a rail member in an expanding direction through the engagement aperture of the stent from an axially-radially nested unexpanded state to an expanded state and resisting movement of the coupling element engaged with the rail member in a contracting direction, opposite to the expanding direction, through the engagement aperture, thereby preventing contraction of the stent toward an axially-radially nested unexpanded state.

2. The offset rail stent of claim 1, wherein each frame element has two rail members extending therefrom.

3. The offset rail stent of claim 2, wherein the coupling elements are formed in pairs.

4. The offset rail stent of claim 3, wherein the coupling elements are formed in a U-shape.

5. The offset rail stent of claim 1, wherein a given coupling element is bonded to a given rail member.

6. The offset rail stent of claim 1, wherein each linkage strand is configured with adjacent frame elements being circumferentially offset relative to each other.

7. The offset rail stent of claim 1, wherein the engagement mechanisms comprise coupling element includes a connecting means disposed thereon being configured to engage an engagement aperture of a frame element of an adjacent linkage strand.

8. The offset rail stent of claim 7, wherein the connecting means comprises a plurality of teeth disposed along a side of the coupling element.

9. The offset rail stent of claim 7, wherein the connecting means comprises a plurality of teeth disposed along a top portion of the coupling element.

10. The offset rail stent of claim 1, further comprising a plurality of scales extending from an exterior surface of at least one of the linkage strands of the tubular member to at least engage a sidewall of a body lumen.

11. The offset rail stent of claim 1, further comprising a therapeutic agent.

12. The offset rail stent of claim 11, wherein the therapeutic agent is selected from the group consisting of an antiproliferative agent, an anti-inflammatory agent, an anti-matrix metalloproteinase agent, a lipid lowering agent, a cholesterol modifying agent, an anti-thrombotic agent and an antiplatelet agent.

13. The offset rail stent of claim 12, wherein the therapeutic agent is an antiproliferative agent selected from the group consisting of Paclitaxel, Rapamycin, ABT-578, Biolimus A9, Everolimus, tacrolimus, and derivatives and analogs thereof.

14. The offset rail stent of claim 1, wherein at least one coupling element comprises a securing point and at least one rail member comprises a protrusion, wherein the protrusion is receivable by the securing point to secure the at least one coupling element to the at least one rail member.

15. The offset rail stent of claim 14, wherein the securing point comprises an aperture that extends through the coupling element.

16. The offset rail stent of claim 14, wherein the securing point comprises a cavity.

17. The offset rail stent of claim 1, wherein at least one coupling element comprises an alignment element and at least one rail member further comprises a protrusion, wherein the protrusion can be received by the alignment element.

18. The offset rail stent of claim 1, wherein at least one engagement aperture comprises a locking mechanism.

19. A radially expandable stent comprising a tubular member having a longitudinal axis, wherein the tubular member comprises:
   a plurality of interwoven strands extending along the longitudinal axis, each strand having at least one frame element, each frame element comprising at least one rail member and at least one engagement aperture, the at least one rail member having a free end separate from the free ends of rail members on other frame members and extending circumferentially about the tubular member and through an engagement aperture of an adjacent strand, the at least one engagement aperture and the rail member being sized such that in a first condition the rail member can pass through the engagement aperture in both an expansion direction and a contraction direction, the contraction directing being opposite the expansion direction; and
   a plurality of coupling elements each connected to a free end of respective ones of the rail members in a second condition, the coupling elements each comprising at least one securing structure and a motion-limiting structure, wherein the securing structure receives at least a portion of a respective rail member and secures the coupling element relative to the respective rail member in at least a circumferential direction, the motion-limiting structure of the coupling element engaging the engagement aperture of a respective frame element to allow one-way movement of the coupling element relative to the respective frame element in only the expansion direction of the interwoven strands with respect to each other and to resist movement of the coupling element relative to the respective frame element in the contraction direction.

20. The stent of claim 19, wherein the at least one rail member comprises a protrusion, the securing structure receiving the protrusion and thereby securing the coupling element relative to the respective rail member in at least the circumferential direction.

21. The stent of claim 20, wherein the protrusion is configured to be snap fitted into the securing structure.

22. The stent of claim 20, wherein the protrusion is configured to be press fitted into the securing structure.

23. The stent of claim 20, further comprising an adhesive that secures the protrusion to the securing structure.

24. The stent of claim 20, wherein the securing structure comprises an aperture that extends through the coupling element.

25. The stent of claim 20, wherein the securing structure comprises a cavity.

26. The stent of claim 19, wherein at least one coupling element comprises an alignment element and the at least one rail member further comprises a protrusion, wherein the protrusion is received by the alignment element and thereby interconnects the at least one coupling element with the at least one rail member.

27. The stent of claim 19, wherein each frame element comprises two rail members extending therefrom.

28. The stent of claim 19, wherein the coupling elements are formed in pairs.

29. The stent of claim 28, wherein the coupling elements are formed in a U-shape.

30. The stent of claim 19, wherein the motion-limiting structure of the coupling element comprises a plurality of teeth.

31. The stent of claim 19, wherein the interwoven strands extend generally parallel relative to each other along the longitudinal axis.

32. The stent of claim 1, further comprising a sheath.

33. The stent of claim 32, wherein the sheath comprises at least one structural pattern.

34. The stent of claim 19, further comprising a sheath.

35. The stent of claim 34, wherein the sheath comprises at least one structural pattern.

* * * * *